(12) United States Patent
Grozinger et al.

(10) Patent No.: US 8,895,284 B2
(45) Date of Patent: Nov. 25, 2014

(54) CLASS II HUMAN HISTONE DEACETYLASES, AND USES RELATED THERETO

(71) Applicant: President and Fellows of Harvard College, Cambridge, MA (US)

(72) Inventors: Christina M. Grozinger, Urbana, IL (US); Christian A. Hassig, Somerville, MA (US); Stuart L. Schreiber, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/888,937

(22) Filed: May 7, 2013

(65) Prior Publication Data

US 2013/0338024 A1   Dec. 19, 2013

Related U.S. Application Data

(60) Division of application No. 13/324,036, filed on Dec. 13, 2011, now Pat. No. 8,435,780, which is a division of application No. 12/370,390, filed on Feb. 12, 2009, now Pat. No. 8,076,116, which is a continuation of application No. 11/831,303, filed on Jul. 31, 2007, now abandoned, which is a continuation of application No. 10/964,313, filed on Oct. 13, 2004, now Pat. No. 7,250,504, which is a continuation of application No. 09/800,187, filed on Mar. 5, 2001, now abandoned.

(60) Provisional application No. 60/186,802, filed on Mar. 3, 2000.

(51) Int. Cl.

| C12N 9/78 | (2006.01) |
|---|---|
| C07K 14/00 | (2006.01) |
| C12Q 1/34 | (2006.01) |
| G01N 33/68 | (2006.01) |
| C12N 9/16 | (2006.01) |
| C12N 9/80 | (2006.01) |
| C12P 21/00 | (2006.01) |

(52) U.S. Cl.
CPC ............. *C12N 9/80* (2013.01); *G01N 33/6875* (2013.01); *A01K 2217/05* (2013.01); *C12Q 1/34* (2013.01); *C12N 9/16* (2013.01)
USPC ........... 435/227; 435/18; 435/69.1; 435/69.7; 530/350

(58) Field of Classification Search
USPC ............................ 435/227, 69.1, 18; 530/350
See application file for complete search history.

(56) References Cited

U.S. PATENT DOCUMENTS

| 4,160,866 A | 7/1979 | Brooks et al. |
|---|---|---|
| 4,608,390 A | 8/1986 | Summers, Jr. |
| 4,631,211 A | 12/1986 | Houghten |
| 4,639,462 A | 1/1987 | Kramer et al. |
| 4,683,195 A | 7/1987 | Mullis et al. |
| 4,683,202 A | 7/1987 | Mullis |
| 4,820,828 A | 4/1989 | Demers et al. |
| 4,833,080 A | 5/1989 | Brent et al. |
| 4,861,798 A | 8/1989 | Tramposch et al. |
| 5,045,538 A | 9/1991 | Schneider et al. |
| 5,059,698 A | 10/1991 | Schulthess et al. |
| 5,096,815 A | 3/1992 | Ladner et al. |
| 5,143,854 A | 9/1992 | Pirrung et al. |
| 5,175,191 A | 12/1992 | Marks et al. |
| 5,176,996 A | 1/1993 | Hogan et al. |
| 5,198,346 A | 3/1993 | Ladner et al. |
| 5,223,409 A | 6/1993 | Ladner et al. |
| 5,225,173 A | 7/1993 | Wai |
| 5,238,781 A | 8/1993 | Schadeli |
| 5,256,775 A | 10/1993 | Froehler |
| 5,264,564 A | 11/1993 | Matteucci |
| 5,283,317 A | 2/1994 | Saifer et al. |
| 5,288,514 A | 2/1994 | Ellman |
| 5,304,121 A | 4/1994 | Sahatjian |
| 5,328,470 A | 7/1994 | Nabel et al. |
| 5,359,115 A | 10/1994 | Campbell et al. |
| 5,362,899 A | 11/1994 | Campbell |
| 5,393,741 A | 2/1995 | Pettersen et al. |
| 5,440,016 A | 8/1995 | Blondelle et al. |
| 5,480,971 A | 1/1996 | Houghten et al. |
| 5,534,654 A | 7/1996 | Ohtani et al. |
| 5,659,016 A | 8/1997 | Nakamura et al. |
| 5,700,811 A | 12/1997 | Breslow et al. |
| 5,763,182 A | 6/1998 | Nakamura et al. |
| 5,837,313 A | 11/1998 | Ding et al. |

(Continued)

FOREIGN PATENT DOCUMENTS

| DE | 32 42 252 | 5/1984 |
|---|---|---|
| EP | 0 259 149 A2 | 3/1988 |

(Continued)

OTHER PUBLICATIONS

Scanlan et al. , GenBank accession No. AAC18040 GI: 3170182; Feb. 9, 1998.*
Scanlan et al., GenBank accession No. AF039691 GI:3170181; Feb. 9, 1998.*
McKinsey et al., Nature 408:106-11, 2000.*
International Search Report and Written Opinion for PCT/US2010/002220, mailed Apr. 27, 2011.
International Preliminary Report on Patentability for PCT/US2010/002220, mailed Feb. 23, 2012.

(Continued)

*Primary Examiner* — Delia Ramirez
(74) *Attorney, Agent, or Firm* — Wolf, Greenfield & Sacks, P.C.; C. Hunter Baker; Daniel W. Young

(57) ABSTRACT

The invention provides histone deacetylase class II nucleic acids and polypeptides, methods and reagents for their use, and related compounds including small molecule libraries containing class II histone deacetylase inhibitors.

23 Claims, 23 Drawing Sheets

(56) References Cited

U.S. PATENT DOCUMENTS

| | | |
|---|---|---|
| 5,886,026 A | 3/1999 | Hunter et al. |
| 5,891,507 A | 4/1999 | Jayaraman |
| 6,030,945 A | 2/2000 | Ashkenazi |
| 6,037,361 A | 3/2000 | Roth et al. |
| 6,068,987 A | 5/2000 | Dulski et al. |
| 6,071,305 A | 6/2000 | Brown et al. |
| 6,099,562 A | 8/2000 | Ding et al. |
| 6,153,252 A | 11/2000 | Hossainy et al. |
| 6,190,619 B1 | 2/2001 | Kilcoin et al. |
| 6,195,612 B1 | 2/2001 | Pack-Harris |
| 6,203,551 B1 | 3/2001 | Wu |
| 6,231,600 B1 | 5/2001 | Zhong |
| 6,248,127 B1 | 6/2001 | Shah et al. |
| 6,251,136 B1 | 6/2001 | Guruwaiya et al. |
| 6,258,121 B1 | 7/2001 | Yang et al. |
| 6,273,913 B1 | 8/2001 | Wright et al. |
| 6,428,960 B1 | 8/2002 | Clark et al. |
| 6,495,719 B2 | 12/2002 | Lan-Hargest et al. |
| 6,503,708 B1 | 1/2003 | Lal et al. |
| 6,512,123 B2 | 1/2003 | Grossmann et al. |
| 6,517,889 B1 | 2/2003 | Jayaraman |
| 6,541,661 B1 | 4/2003 | Delorme et al. |
| 6,777,217 B1 | 8/2004 | Schreiber et al. |
| 6,797,820 B2 | 9/2004 | Patel et al. |
| 6,897,220 B2 | 5/2005 | Delorme et al. |
| 6,960,685 B2 | 11/2005 | Watkins et al. |
| 7,244,853 B2 | 7/2007 | Schreiber et al. |
| 7,250,504 B2 | 7/2007 | Grozinger et al. |
| 7,335,753 B2 | 2/2008 | Wang et al. |
| 7,514,406 B2 | 4/2009 | Bedalov et al. |
| 7,737,172 B2 | 6/2010 | Halperin et al. |
| 7,994,362 B2 | 8/2011 | Schreiber et al. |
| 8,076,116 B2 | 12/2011 | Grozinger et al. |
| 8,178,579 B2 | 5/2012 | Schreiber et al. |
| 8,222,423 B2 | 7/2012 | Bradner et al. |
| 8,304,451 B2 | 11/2012 | Mazitschek et al. |
| 8,329,945 B2 | 12/2012 | Schreiber et al. |
| 8,329,946 B2 | 12/2012 | Schreiber et al. |
| 8,362,084 B2 | 1/2013 | Schreiber et al. |
| 8,383,855 B2 | 2/2013 | Bradner et al. |
| 8,399,233 B2 | 3/2013 | Schreiber et al. |
| 8,426,592 B2 | 4/2013 | Schreiber et al. |
| 8,435,780 B2 | 5/2013 | Grozinger et al. |
| 8,440,716 B2 | 5/2013 | Tang et al. |
| 8,716,344 B2 | 5/2014 | Mazitschek et al. |
| 8,754,237 B2 | 6/2014 | Bradner et al. |
| 2001/0027340 A1 | 10/2001 | Wright et al. |
| 2003/0004209 A1 | 1/2003 | Hunter et al. |
| 2003/0129724 A1 | 7/2003 | Grozinger et al. |
| 2003/0187027 A1 | 10/2003 | Schreiber et al. |
| 2003/0216345 A1 | 11/2003 | Nakanishi et al. |
| 2004/0072849 A1 | 4/2004 | Schreiber et al. |
| 2004/0087631 A1 | 5/2004 | Bacopoulos et al. |
| 2004/0092598 A1 | 5/2004 | Watkins et al. |
| 2004/0127522 A1 | 7/2004 | Chiao et al. |
| 2004/0138153 A1 | 7/2004 | Ramesh et al. |
| 2005/0014839 A1 | 1/2005 | Kozikowski et al. |
| 2005/0267037 A1 | 12/2005 | Anderson et al. |
| 2005/0287629 A1 | 12/2005 | Grozinger et al. |
| 2006/0020131 A1 | 1/2006 | Raeppel et al. |
| 2006/0079528 A1 | 4/2006 | Finn et al. |
| 2006/0239909 A1 | 10/2006 | Anderson et al. |
| 2007/0093413 A1 | 4/2007 | Schreiber et al. |
| 2007/0148185 A1 | 6/2007 | Rathore et al. |
| 2008/0207590 A1 | 8/2008 | Deziel et al. |
| 2008/0269245 A1 | 10/2008 | Schreiber et al. |
| 2008/0300205 A1 | 12/2008 | Tsai et al. |
| 2009/0036318 A1 | 2/2009 | Grozinger et al. |
| 2009/0209590 A1 | 8/2009 | Mazitschek et al. |
| 2009/0305384 A1 | 12/2009 | Grozinger et al. |
| 2009/0312363 A1 | 12/2009 | Bradner et al. |
| 2010/0041653 A1 | 2/2010 | Pellecchia et al. |
| 2010/0056588 A1 | 3/2010 | Bradner et al. |
| 2010/0137196 A1 | 6/2010 | Schreiber et al. |
| 2011/0172303 A1 | 7/2011 | Tang et al. |
| 2011/0218154 A1 | 9/2011 | Schreiber et al. |
| 2011/0313045 A1 | 12/2011 | Schreiber et al. |
| 2011/0319493 A1 | 12/2011 | Schreiber et al. |
| 2012/0094862 A1 | 4/2012 | Grozinger et al. |
| 2012/0208889 A1 | 8/2012 | Mazitschek et al. |
| 2012/0302510 A1 | 11/2012 | Schreiber et al. |
| 2013/0018103 A1 | 1/2013 | Bradner et al. |
| 2013/0040998 A1 | 2/2013 | Bradner et al. |
| 2013/0331455 A1 | 12/2013 | Tang et al. |

FOREIGN PATENT DOCUMENTS

| | | |
|---|---|---|
| EP | 0 322 335 A1 | 6/1989 |
| EP | 0 323 590 A2 | 7/1989 |
| EP | 0 331 524 A2 | 9/1989 |
| EP | 0 458 131 A1 | 11/1991 |
| EP | 0 708 112 A1 | 4/1996 |
| GB | 1 394 170 A | 5/1975 |
| GB | 2 169 599 A | 7/1986 |
| JP | 59-139390 A | 8/1984 |
| JP | 04-022948 A | 1/1992 |
| JP | 04-217929 A | 8/1992 |
| JP | 06-001720 A | 1/1994 |
| JP | 8-311321 A | 11/1996 |
| JP | 9-124918 A | 5/1997 |
| JP | 2003-221398 A | 8/2003 |
| JP | 2004-043446 A | 2/2004 |
| WO | WO 91/00257 A1 | 1/1991 |
| WO | WO 91/07087 A1 | 5/1991 |
| WO | WO 92/09690 A2 | 6/1992 |
| WO | WO 92/10092 A1 | 6/1992 |
| WO | WO 92/15694 A1 | 9/1992 |
| WO | WO 93/05807 A2 | 4/1993 |
| WO | WO 93/07148 A1 | 4/1993 |
| WO | WO 93/07867 A1 | 4/1993 |
| WO | WO 93/09668 A1 | 5/1993 |
| WO | WO 93/19778 A1 | 10/1993 |
| WO | WO 93/20242 A1 | 10/1993 |
| WO | WO 94/08051 A1 | 4/1994 |
| WO | WO 94/10300 A1 | 5/1994 |
| WO | WO 97/11366 A1 | 3/1997 |
| WO | WO 97/35990 A2 | 10/1997 |
| WO | WO 98/16830 A2 | 4/1998 |
| WO | WO 98/47869 A1 | 10/1998 |
| WO | WO 98/55449 A1 | 12/1998 |
| WO | WO 00/20415 A1 | 4/2000 |
| WO | WO 00/34313 A1 | 6/2000 |
| WO | WO 00/35911 A1 | 6/2000 |
| WO | WO 00/36132 A1 | 6/2000 |
| WO | WO 00/44709 A2 | 8/2000 |
| WO | WO 02/22577 A2 | 3/2002 |
| WO | WO 02/089782 A2 | 11/2002 |
| WO | WO 04/001059 A2 | 12/2003 |
| WO | WO 2004/046104 A2 | 6/2004 |
| WO | WO 2004/062601 A2 | 7/2004 |
| WO | WO 2004/103369 A1 | 12/2004 |
| WO | WO 2005/007091 A2 | 1/2005 |
| WO | WO 2005/012247 A1 | 2/2005 |
| WO | WO 2005/018578 A2 | 3/2005 |
| WO | WO 2005/058803 A1 | 6/2005 |
| WO | WO 2005/066151 A2 | 7/2005 |
| WO | WO 2005/080335 A1 | 9/2005 |
| WO | WO 2006/060676 A1 | 6/2006 |
| WO | WO 2006/060809 A2 | 6/2006 |
| WO | WO 2007/111948 A2 | 10/2007 |
| WO | WO 2008/040934 A1 | 4/2008 |
| WO | WO 2008/091349 A1 | 7/2008 |
| WO | WO 2009/063054 A1 | 5/2009 |
| WO | WO 2011/019393 A2 | 2/2011 |

OTHER PUBLICATIONS

Extended European Search Report for EP 07872648.6, mailed Apr. 13, 2011.
Invitation to Pay Additional Fees for PCT/US2007/062145, mailed Oct. 29, 2007.
International Search Report and Written Opinion for PCT/US2007/062145, mailed Jun. 24, 2008.
International Preliminary Report on Patentability for PCT/US2007/062145, mailed Aug. 28, 2008.

(56) References Cited

OTHER PUBLICATIONS

Extended European Search Report for EP 07757000.0, mailed May 3, 2011.
Invitation to Pay Additional Fees for PCT/US2007/062152, mailed Dec. 7, 2007.
International Search Report and Written Opinion for PCT/US2007/062152, mailed Oct. 7, 2008.
International Search Report and Written Opinion for PCT/US2007/062152, mailed Oct. 14, 2008.
International Preliminary Report on Patentability for PCT/US2007/062152, mailed Mar. 19, 2009.
Extended European Search Report for EP 09800666.1, mailed Aug. 24, 2011.
International Search Report and Written Opinion for PCT/US2009/004235, mailed Mar. 4, 2010.
International Preliminary Report on Patentability for PCT/US2009/004235, mailed Feb. 3, 2011.
Supplementary European Search Report for EP 06748614.2, mailed Oct. 16, 2009.
Extended European Search Report for EP 12150229.8, mailed Jul. 31, 2012.
International Search Report and Written Opinion for PCT/US2006/010676, mailed Jul. 14, 2008.
International Preliminary Report on Patentability for PCT/US2006/010676, mailed Mar. 19, 2009.
Extended European Search Report for EP 07776589.9, mailed Jun. 1, 2012.
International Search Report and Written Opinion for PCT/US2007/010587, mailed Jan. 29, 2008.
International Preliminary Report on Patentability for PCT/US2007/010587, mailed Nov. 13, 2008.
International Search Report for PCT/US2002/014835, mailed Dec. 20, 2002.
Written Opinion for PCT/US2002/014835, mailed Aug. 8, 2003.
International Preliminary Exam Report for PCT/US2002/014835, mailed Jun. 4, 2004.
International Search Report and Written Opinion for PCT/US2011/020206, mailed Jul. 9, 2013.
International Preliminary Report on Patentability for PCT/US2011/020206, mailed Aug. 1, 2013.
Invitation to Pay Additional Fees for PCT/US1997/005275, mailed Nov. 21, 1997.
International Search Report for PCT/US1997/005275, mailed Feb. 16, 1998.
Written Opinion for PCT/US1997/005275, mailed Mar. 5, 1998.
International Preliminary Examination Report for PCT/US1997/005275, mailed Jul. 3, 1998.
Office Communication, mailed Jul. 29, 2013, for U.S. Appl. No. 13/389,814.
Office Communication, mailed Jun. 20, 2011, for U.S. Appl. No. 12/279,440.
Office Communication, mailed Sep. 29, 2011, for U.S. Appl. No. 12/279,440.
Notice of Allowance, mailed Mar. 13, 2012, for U.S. Appl. No. 12/279,440.
Office Communication, mailed Feb. 13, 2013, for U.S. Appl. No. 13/550,110.
Office Communication, mailed Jul. 8, 2013, for U.S. Appl. No. 13/550,110.
Office Communication, mailed Dec. 21, 2011, for U.S. Appl. No. 12/279,398.
Notice of Allowance, mailed Jan. 22, 2013, for U.S. Appl. No. 13/055,241.
Office Communication, mailed Oct. 15, 2008, for U.S. Appl. No. 11/386,959.
Office Communication, mailed Jul. 21, 2009, for U.S. Appl. No. 11/386,959.
Advisory Action, mailed Nov. 17, 2009, for U.S. Appl. No. 11/386,959.
Office Communication, mailed Dec. 18, 2012, for U.S. Appl. No. 11/386,959.
Office Communication, mailed Aug. 6, 2013, for U.S. Appl. No. 11/386,959.
Office Communication, mailed Nov. 29, 2011, for U.S. Appl. No. 12/299,430.
Office Communication, mailed Mar. 21, 2012, for U.S. Appl. No. 12/299,430.
Notice of Allowance, mailed Jul. 2, 2012, for U.S. Appl. No. 12/299,430.
Office Communication, mailed Nov. 28, 2005, for U.S. Appl. No. 10/621,276.
Office Communication, mailed Aug. 8, 2006, for U.S. Appl. No. 10/621,276.
Notice of Allowance, mailed Mar. 6, 2007, for U.S. Appl. No. 10/621,276.
Office Communication, mailed Sep. 16, 2009, for U.S. Appl. No. 11/879,466.
Notice of Allowance, mailed Feb. 4, 2010, for U.S. Appl. No. 11/879,466.
Notice of Allowance, mailed Jan. 17, 2012, for U.S. Appl. No. 11/879,466.
Office Communication, mailed Aug. 16, 2013, for U.S. Appl. No. 13/520,650.
Office Communication, mailed Jan. 21, 1998, for U.S. Appl. No. 08/624,735.
Office Communication, mailed Jan. 17, 2001, for U.S. Appl. No. 08/624,735.
Office Communication, mailed Oct. 10, 2001, for U.S. Appl. No. 08/624,735.
Office Communication, mailed Oct. 16, 2002, for U.S. Appl. No. 08/624,735.
Office Communication, mailed Aug. 12, 2003, for U.S. Appl. No. 08/624,735.
Notice of Allowance, mailed Apr. 13, 2004, for U.S. Appl. No. 08/624,735.
Office Communication, mailed May 6, 2009, for U.S. Appl. No. 10/919,217.
Office Communication, mailed Mar. 4, 2010, for U.S. Appl. No. 10/919,217.
Office Communication, mailed Oct. 14, 2010, for U.S. Appl. No. 10/919,217.
Office Communication, mailed Nov. 23, 2011, for U.S. Appl. No. 10/919,217.
Notice of Allowance, mailed Nov. 30, 2012, for U.S. Appl. No. 10/919,217.
Office Communication, mailed Apr. 8, 2010, for U.S. Appl. No. 12/196,878.
Office Communication, mailed Aug. 10, 2010, for U.S. Appl. No. 12/196,878.
Office Communication, mailed Jan. 18, 2011, for U.S. Appl. No. 12/196,878.
Notice of Allowance, mailed Jun. 8, 2011, for U.S. Appl. No. 12/196,878.
Office Communication, mailed Aug. 5, 2010, for U.S. Appl. No. 12/196,946.
Office Communication, mailed Dec. 28, 2010, for U.S. Appl. No. 12/196,946.
Advisory Action, mailed Apr. 14, 2011, for U.S. Appl. No. 12/196,946.
Office Communication, mailed May 6, 2013, for U.S. Appl. No. 12/196,946.
Office Communication, mailed Sep. 23, 2011, for U.S. Appl. No. 13/030,086.
Office Communication, mailed Feb. 24, 2012, for U.S. Appl. No. 13/030,086.
Notice of Allowance, mailed Sep. 21, 2012, for U.S. Appl. No. 13/030,086.
Office Communication, mailed May 1, 2012, for U.S. Appl. No. 13/221,602.
Notice of Allowance, mailed Aug. 13, 2012, for U.S. Appl. No. 13/221,602.

(56) References Cited

OTHER PUBLICATIONS

Office Communication, mailed May 1, 2012, for U.S. Appl. No. 13/221,561.
Notice of Allowance, mailed Aug. 13, 2012, for U.S. Appl. No. 13/221,561.
Office Communication, mailed Oct. 16, 2012, for U.S. Appl. No. 13/566,803.
Notice of Allowance, mailed Jan. 30, 2013, for U.S. Appl. No. 13/566,803.
Office Communication, mailed Jun. 30, 2003, for U.S. Appl. No. 09/800,187.
Office Communication, mailed Apr. 13, 2004, for U.S. Appl. No. 09/800,187.
Notice of Allowance, mailed Apr. 13, 2007, for U.S. Appl. No. 10/964,313.
Office Communication, mailed Sep. 17, 2009, for U.S. Appl. No. 11/831,303.
Office Communication, mailed Apr. 2, 2010, for U.S. Appl. No. 12/370,390.
Office Communication, mailed Oct. 8, 2010, for U.S. Appl. No. 12/370,390.
Office Communication, mailed Apr. 28, 2011, for U.S. Appl. No. 12/370,390.
Notice of Allowance, mailed Aug. 17, 2011, for U.S. Appl. No. 12/370,390.
Office Communication, mailed Apr. 24, 2012, for U.S. Appl. No. 13/324,036.
Office Communication, mailed Sep. 27, 2012, for U.S. Appl. No. 13/324,036.
Notice of Allowance, mailed Jan. 9, 2013, for U.S. Appl. No. 13/324,036.
[No Author Listed] Inhibitor. Available at http://www.biology-online.org/dictionary/inhibitor. Last accessed Apr. 6, 2011. 1 page.
[No Author Listed] Targeting the aggresome with an HDAC6 inhibitor in combination with velcade for myeloma therapy. Cancer Biology and Therapy. 2005;4(7):i-iv.
[No Author Listed] TopoTarget. Executive Informational Overview. Jan. 26, 2005. 52 pages.
Abremski et al., Bacteriophage P1 site-specific recombination. Purification and properties of the Cre recombinase protein. J Biol Chem. Feb. 10, 1984;259(3):1509-14.
Adams et al., Initial assessment of human gene diversity and expression patterns based upon 83 million nucleotides of cDNA sequence. Nature. Sep. 28, 1995;377(6547 Suppl):3-174.
Adams, The proteasome: a suitable antineoplastic target. Nat Rev Cancer. May 2004;4(5):349-60.
Afshar et al., Characterization of a human gene with sequence homology to *Saccharomyces cerevisiae* SIR2. Gene. Jun. 24, 1999;234(1):161-8.
Aggarwal et al., Trifluoromethanesulfonic Acid, an Efficient Catalyst for the Hetero Diels-Alder Reaction and an Improved Synthesis of Mefrosol. Tetrahedron Letters. 1997;38:2569-72.
Ahringer, NuRD and SIN3 histone deacetylase complexes in development. Trends Genet. Aug. 2000;16(8):351-6.
Alonso et al., A novel yeast histone deacetylase: partial characterization and development of an activity assay. Biochim Biophys Acta. Mar. 26, 1986;866(2-3):161-9.
Anderson et al., Analytical Techniques in Combinatorial Chemistry: MAS CH Correlation in Solvent-Swollen Resin. J Org Chem. 1995;60:2650-51.
Andrews et al., Anti-malarial effect of histone deacetylation inhibitors and mammalian tumour cytodifferentiating agents. Int J Parasitol. May 2000;30(6):761-8.
Anklesaria et al., Engraftment of a clonal bone marrow stromal cell line in vivo stimulates hematopoietic recovery from total body irradiation. Proc Natl Acad Sci U S A. Nov. 1987;84(21):7681-5.
Antón et al., Intracellular localization of proteasomal degradation of a viral antigen. J Cell Biol. Jul. 12, 1999;146(1):113-24.
Antonjuk et al., Asymmetric Induction in the Additions of Anions of Allylic Sulfoxides to Benzaldehyde. Aust J Chem. 1980;33:2635-51.
Aparicio et al., Modifiers of position effect are shared between telomeric and silent mating-type loci in *S. cerevisiae*. Cell. Sep. 20, 1991;66(6):1279-87.
Arkin et al., An algorithm for protein engineering: simulations of recursive ensemble mutagenesis. Proc Natl Acad Sci U S A. Aug. 15, 1992;89(16):7811-5.
Attal et al., Single versus double autologous stem-cell transplantation for multiple myeloma. N. Engl J Med. Dec. 25, 2003;349(26):2495-502.
Auffray et al., [Image: molecular integration of the analysis of the human genome and its expression.] C R Acad Sci III. Feb. 1995;318(2):263-72. French.
Baer et al., Eukaryotic RNA polymerase II binds to nucleosome cores from transcribed genes. Nature. Feb. 10, 1983;301(5900):482-8.
Baldwin et al., Total Synthesis of Antitumor Agent At-125-(Aphas, 5S)-Alpha-Amino-3-Chloro-4,5-Isoxazoleacetic Acid. Tetrahedron. 1985;41(22):5241-60.
Ballestar et al., Methyl-CpG-binding proteins. Targeting specific gene repression. Eur J Biochem. Jan. 2001;268(1):1-6.
Barbas et al., Semisynthetic combinatorial antibody libraries: a chemical solution to the diversity problem. Proc Natl Acad Sci U S A. May 15, 1992;89(10):4457-61.
Bartel et al., Elimination of false positives that arise in using the two-hybrid system. Biotechniques. Jun. 1993;14(6):920-4.
Beck-Sickinger et al., Neuropeptide Y: identification of the binding site. Int J Pept Protein Res. Dec. 1990;36(6):522-30.
Beck-Sickinger et al., Semiautomated T-bag peptide synthesis using 9-fluorenyl-methoxycarbonyl strategy and benzotriazol-1-yl-tetramethyl-uronium tetrafluoroborate activation. Pept Res. Mar.-Apr. 1991;4(2):88-94.
Beck-Sickinger et al., Structure/activity relationships of C-terminal neuropeptide Y peptide segments and analogues composed of sequence 1-4 linked to 25-36. Eur J Biochem. Dec. 12, 1990;194(2):449-56.
Ben-Bassat et al., Processing of the initiation methionine from proteins: properties of the *Escherichia coli* methionine aminopeptidase and its gene structure. J Bacteriol. Feb. 1987;169(2):751-7.
Bennett et al., Global impairment of the ubiquitin-proteasome system by nuclear or cytoplasmic protein aggregates precedes inclusion body formation. Mol Cell. Feb. 4, 2005;17(3):351-65.
Berenbaum et al., What is synergy? Pharmacol Rev. Jun. 1989;41(2):93-141.
Berg et al., Long-Chain Polystyrene-Grafted Polyethylene Film Matrix: A New Support for Solid-Phase Peptide Synthesis. J Am Chem Soc. 1989;111:8024-26.
Berge et al., Pharmaceutical salts. J Pharm Sci. Jan. 1977;66(1):1-19.
Bernstein et al., Genomewide studies of histone deacetylase function in yeast. Proc Natl Acad Sci U S A. Dec. 5, 2000;97(25):13708-13.
Blackwell et al., A one-bead, one-stock solution approach to chemical genetics: part 1. Chem Biol. Dec. 2001;8(12):1167-82.
Blankemeyer-Menge et al., Simultaneous Multiple Synthesis of Protected Peptide Fragments on "Allyl"-Functionalized Cellulose Disc Supports. Tetrahedron Lett. 1988;29:5871-74.
Blondelle et al., Soluble combinatorial libraries of organic, peptidomimetic and peptide diversities. Trends Anal Chem. 1995;14:83-92.
Bolden et al., Anticancer activities of histone deacetylase inhibitorsNat Rev Drug Discov. Sep. 2006;5(9):769-84.
Bolger et al., Intracellular trafficking of histone deacetylase 4 regulates neuronal cell death. J Neurosci. Oct. 12, 2005;25(41):9544-53.
Borchardt et al., Synthetic Receptor Binding Elucidated with an Encoded Combinatorial Library. J Am Chem Soc. 1994;116:373-74.
Bottomley et al., Structural and functional analysis of the human HDAC4 catalytic domain reveals a regulatory structural zinc-binding domain. J Biol Chem. Sep. 26, 2008;283(39):26694-704. Epub Jul. 8, 2008.
Bowdish et al., Analysis of RIM11, a yeast protein kinase that phosphorylates the meiotic activator IME1. Mol Cell Biol. Dec. 1994;14(12):7909-19.
Bowdish et al., Bipartite structure of an early meiotic upstream activation sequence from *Saccharomyces cerevisiae*. Mol Cell Biol. Apr. 1993;13(4):2172-81.

(56) References Cited

OTHER PUBLICATIONS

Bowers et al., Synthesis and Conformation—Activity Relationships of the Peptide Isosteres of FK228 and Largazole. J Am Chem Soc. 2009;131:2900-05.
Bowers et al., Total synthesis and biological mode of action of largazole: a potent class I histone deacetylase inhibitor. J Am Chem Soc. Aug. 20, 2008;130(33):11219-22. Epub Jul. 19, 2008.
Brachman et al., The SIR2 gene family, conserved from bacteria to humans, functions in silencing, cell cycle progression, and chromosome stability. Genes Dev. Dec. 1, 1995;9(23):2888-902.
Bradley et al., Formation of germ-line chimaeras from embryo-derived teratocarcinoma cell lines. Nature. May 17-23, 1984;309(5965):255-6.
Bradner et al., Chemical phylogenetics of histone deacetylases. Nat Chem Biol. Mar. 2010;6(3):238-243. Epub Feb. 7, 2010.
Branden et al., Chapter 16. Prediction, Engineering, and Design of Protein Structures. In: Introduction to Protein Structure. Garland Publishing Inc., New York. 1991:247.
Braunstein et al., Efficient transcriptional silencing in *Saccharomyces cerevisiae* requires a heterochromatin histone acetylation pattern. Mol Cell Biol. Aug. 1996;16(8):4349-56.
Braunstein et al., Transcriptional silencing in yeast is associated with reduced nucleosome acetylation. Genes Dev. Apr. 1993;7(4):592-604.
Bray et al., Gas Phase Cleavage of Peptides from a Solid Support with Ammonia Vapour. Application in Simultaneous Multiple Peptide Synthesis. Tetrahedron Lett. 1991;32:6163-66.
Bray et al., The Simultaneous Multiple Production of Solution Phase Peptides; Assessment of the Geysen Method of Simultaneous Peptide Synthesis. Tetrahedron Lett. 1990;31:5811-14.
Brenner et al., Encoded combinatorial chemistry. Proc Natl Acad Sci U S A. Jun. 15, 1992;89(12):5381-3.
Breslow et al., Potent cytodifferentiating agents related to hexamethylenebisacetamide. Proc Natl Acad Sci U S A. Jul. 1, 1991;88(13):5542-6.
Brinster et al., Factors affecting the efficiency of introducing foreign DNA into mice by microinjecting eggs. Proc Natl Acad Sci U S A. Jul. 1985;82(13):4438-42.
Brownell et al., Tetrahymena histone acetyltransferase A: a homolog to yeast Gcn5p linking histone acetylation to gene activation. Cell. Mar. 22, 1996;84(6):843-51.
Brummel et al., A mass spectrometric solution to the address problem of combinatorial libraries. Science. Apr. 15, 1994;264(5157):399-402.
Brunet et al., Nuclear translocation of p42/p44 mitogen-activated protein kinase is required for growth factor-induced gene expression and cell cycle entry. EMBO J. Feb. 1, 1999;18(3):664-74.
Butting et al., Detection of aberrant DNA methylation in unique Prader-Willi syndrome patients and its diagnostic implications. Hum Mol Genet. Jun. 1994;3(6):893-5.
Bundgaard, Chapter 1. Design of prodrugs: Bioreversible derivatives for various functional groups and chemical entities. In: Design of Prodrugs. Elsevier. 1985:1-3.
Burbaum et al., A paradigm for drug discovery employing encoded combinatorial libraries. Proc Natl Acad Sci U S A. Jun. 20, 1995;92(13):6027-31.
Burbelo et al., 14-3-3 proteins. Hot numbers in signal transduction. Curr Biol. Feb. 1, 1995;5(2):95-6.
Byrd et al., Depsipeptide (FR901228): a novel therapeutic agent with selective, in vitro activity against human B-cell chronic lymphocytic leukemia cells. Blood. Aug. 15, 1999;94(4):1401-8.
Calí et al., Nucleotide sequence of a cDNA encoding the human muscle-specific enolase (MSE). Nucleic Acids Res. Apr. 11, 1990;18(7):1893.
Cameron, Recent advances in transgenic technology. Mol Biotechnol. Jun. 1997;7(3):253-65.
Carmen et al., HDA1 and HDA3 are components of a yeast histone deacetylase (HDA) complex. J Biol Chem. Jun. 28, 1996;271(26):15837-44.
Carter et al., Chemotherapy of Cancer. 2nd ed. John Wiley & Sons, N.Y., N.Y., 1981:362-65.
CAS Registry File RN 456-07-05, STN Entry Date: Nov. 16, 1984.
CAS Registry File RN 505-22-6, STN Entry Date: Nov. 16, 1984.
Catley et al., NVP-LAQ824 is a potent novel histone deacetylase inhibitor with significant activity against multiple myeloma. Blood. Oct. 1, 2003;102(7):2615-22. Epub Jun. 19, 2003.
Cavenee et al., Expression of recessive alleles by chromosomal mechanisms in retinoblastoma. Nature. Oct. 27-Nov. 2, 1983;305(5937):779-84.
Chauhan et al., Blockade of Hsp27 overcomes Bortezomib/proteasome inhibitor PS-341 resistance in lymphoma cells. Cancer Res. Oct. 1, 2003;63(19):6174-7.
Chauhan et al., Hsp27 inhibits release of mitochondrial protein Smac in multiple myeloma cells and confers dexamethasone resistance. Blood. Nov. 1, 2003;102(9):3379-86. Epub Jul. 10, 2003.
Chen et al., "Analogous" Organic Synthesis of Small-Compound Libraries: Validation of Combinatorial Chemistry in Small-Molecule Synthesis. JACS. 1994;116:2661-62.
Chen et al., Gene therapy for brain tumors: regression of experimental gliomas by adenovirus-mediated gene transfer in vivo. Proc Natl Acad Sci U S A. Apr. 12, 1994;91(8):3054-7.
Chu et al., Free Solution Identification of Candidate Peptides from Combinatorial Libraries by Affinity Capillary Electrophoresis/Mass Spectrometry. J Am Chem Soc. 1995;117:5419-20.
Clackson et al., Making antibody fragments using phage display libraries. Nature. Aug. 15, 1991;352(6336):624-8.
Clemons et al., A one-bead, one-stock solution approach to chemical genetics: part 2. Chem Biol. Dec. 2001;8(12):1183-95.
Clipstone et al., Identification of calcineurin as a key signalling enzyme in T-lymphocyte activation. Nature. Jun. 25, 1992;357(6380):695-7.
Cockell et al., Nuclear compartments and gene regulation. Curr Opin Genet Dev. Apr. 1999;9(2):199-205.
Cohen et al., The histone deacetylase HDAC4 connects neural activity to muscle transcriptional reprogramming. J Biol Chem. Nov. 16, 2007;282(46):33752-9. Epub Sep. 16, 2007.
Corcoran et al., A novel action of histone deacetylase inhibitors in a protein aggresome disease model. Curr Biol. Mar. 23, 2004;14(6):488-92.
Cress et al., Histone deacetylases, transcriptional control, and cancer. J Cell Physiol. Jul. 2000;184(1):1-16.
Csordas, On the biological role of histone acetylation. Biochem J. Jan. 1, 1990;265(1):23-38.
Cuperus et al., Locus specificity determinants in the multifunctional yeast silencing protein Sir2. EMBO J. Jun. 1, 2000;19(11):2641-51.
Curtin et al., Succinimide hydroxamic acids as potent inhibitors of histone deacetylase (HDAC). Bioorg Med Chem Lett. Oct. 21, 2002;12(20):2919-23.
Cwirla et al., Peptides on phage: a vast library of peptides for identifying ligands. Proc Natl Acad Sci U S A. Aug. 1990;87(16):6378-82.
Dancey et al., Strategies for optimizing combinations of molecularly targeted anticancer agents. Nat Rev Drug Discov. Aug. 2006;5(8):649-59.
Dangond et al., Differential display cloning of a novel human histone deacetylase (HDAC3) cDNA from PHA-activated immune cells. Biochem Biophys Res Commun. Jan. 26, 1998;242(3):648-52.
Dankwardt et al., Solid-phase synthesis of di- and tripeptidic hydroxamic acids as inhibitors of procollagen C-proteinase. Bioorg Med Chem Lett. Nov. 20, 2000;10(22):2513-6.
Dann et al., Human renin: a new class of inhibitors. Biochem Biophys Res Commun. Jan. 14, 1986;134(1):71-7.
David et al., Histone deacetylase associated with mSin3A mediates repression by the acute promyelocytic leukemia-associated PLZF protein. Oncogene. May 14, 1998;16(19):2549-56.
Davie et al., Multiple functions of dynamic histone acetylation. J Cell Biochem. May 1994;55(1):98-105.
De Ruijter et al., Histone deacetylases (HDACs): characterization of the classical HDAC family. Biochem J. Mar. 15, 2003;370(Pt 3):737-49.
Delgrave et al., Recursive ensemble mutagenesis. Protein Engineer. 1993;6(3):327-31.

(56) References Cited

OTHER PUBLICATIONS

Denlinger et al., Proteasome inhibition sensitizes non-small cell lung cancer to histone deacetylase inhibitor-induced apoptosis through the generation of reactive oxygen species. J Thorac Cardiovasc Surg. Nov. 2004;128(5):740-8.

Dessolin et al., No. 454. Réactivité des acides hydroxamiques vis-à-vis d'esters activés. Étude cinétique. Bull Soc Chim Fr. 1970;7:2573-80.

Dev et al., Electrochemotherapy—a novel method of cancer treatment. Cancer Treat Rev. Jan. 1994;20(1):105-15.

Devlin et al., Random peptide libraries: a source of specific protein binding molecules. Science. Jul. 27, 1990;249(4967):404-6.

Dower et al., Chapter 28. The Search for Molecular Diversity (II): Recombinant and Synthetic Randomized Peptide Libraries. Annu Rep Med Chem. 1991;26:271-80.

Dul et al., Hsp70 and antifibrillogenic peptides promote degradation and inhibit intracellular aggregation of amyloidogenic light chains. J Cell Biol. Feb. 19, 2001;152(4):705-15.

Egner et al., Solid Phase Chemistry: Direct Monitoring by Matrix-Assisted Laser Desorption/Ionization Time of Flight Mass Spectrometry. A Tool for Combinatorial Chemistry. J Org Chem. 1995;60:2652-53.

Eichler et al., Application of Cellulose Paper as Support Material in Simultaneous Solid Phase Peptide Synthesis. Collect Czech Chem Commun. 1989;54:1746-52.

Eichler et al., Evaluation of cotton as a carrier for solid-phase peptide synthesis. Pept Res. Sep.-Oct. 1991;4(5):296-307.

Eliel et al., Conformational analysis. XX. Stereochemistry of reaction of Grignard reagents with ortho esters. Synthesis of 1,3-dioxanes with axial substituents at C-2. J Am Chem Soc. 1970;92(3):584-590.

Ellison et al., Epitope-tagged ubiquitin. A new probe for analyzing ubiquitin function. J Biol Chem. Nov. 5, 1991;266(31):21150-7.

Emiliani et al., Characterization of a human RPD3 ortholog, HDAC3. Proc Natl Acad Sci U S A. Mar. 17, 1998;95(6):2795-800.

Evans et al., An engineered poliovirus Chimaera elicits broadly reactive HIV-1 neutralizing antibodies. Nature. Jun. 1, 1989;339(6223):385-8.

Evans et al., Establishment in culture of pluripotential cells from mouse embryos. Nature. Jul. 9, 1981;292(5819):154-6.

Ewenson et al., Ketomethylene pseudopeptide analogues of substance P: synthesis and biological activity. J Med Chem. Feb. 1986;29(2):295-9.

Fabian et al., A small molecule-kinase interaction map for clinical kinase inhibitors. Nat Biotechnol. Mar. 2005;23(3):329-36. Epub Feb. 13, 2005.

Fabunmi et al., Activity and regulation of the centrosome-associated proteasome. J Biol Chem. Jan. 7, 2000;275(1):409-13.

Farkas et al., A comparison between the chelating properties of some dihydroxamic acids, desferrrioxamine B and acetohydroxamic acid. Polyhedron. 1999;18(1999):2391-98.

Feling et al., Salinosporamide A: a highly cytotoxic proteasome inhibitor from a novel microbial source, a marine bacterium of the new genus Salinospora. Angew Chem Int Ed Engl. Jan. 20, 2003;42(3):355-7.

Felsenfeld, Chromatin as an essential part of the transcriptional mechanism. Nature. Jan. 16, 1992;355(6357):219-24.

Feng et al., Progressive sequence alignment as a prerequisite to correct phylogenetic trees. J Mol Evol. 1987;25(4):351-60.

Finnin et al., Structures of a histone deacetylase homologue bound to the TSA and SAHA inhibitors. Nature. Sep. 9, 1999;401(6749):188-93.

Fischle et al., A new family of human histone deacetylases related to Saccharomyces cerevisiae HDA1p. J Biol Chem. Apr. 23, 1999;274(17):11713-20.

Fitch et al., High-Resolution 1H NMR in Solid-Phase Organic Synthesis. J Org Chem. 1994;59:7955-56.

Fitch, Distinguishing Homologous from Analogous Proteins. Syst Zool. 1970;19:99-113.

Fleming et al., The total synthesis of ( )-trichostatin A: Some observations on the acylation and alkylation of silyl enol ethers, silyl dienol ethers and a silyl trienol ether. Tetrahedron. 1983;39:841-46.

Fodor et al., Light-directed, spatially addressable parallel chemical synthesis. Science. Feb. 15, 1991;251(4995):767-73.

Frank et al., Simultaneous Multiple Peptide Synthesis Under Continuous Flow Conditions on Cellulose Paper Discs as Segmental Solid Supports. Tetrahedron. 1988;44:6031-40.

Frank, Spot-Synthesis: An Easy Technique for the Positionally Addressable, Parallel Chemical Synthesis on a Membrane Support. Tetrahedron. 1992;48:9217-32.

Frank, Strategies and Techniques in Simultaneous Solid Phase Synthesis Based on the Segmentation of Membrane Type Supports. Bioorg Med Chem Lett. 1993;3:425-30.

Friend et al., Deletions of a DNA sequence in retinoblastomas and mesenchymal tumors: organization of the sequence and its encoded protein. Proc Natl Acad Sci U S A. Dec. 1987;84(24):9059-63.

Frye et al., Characterization of Five Human cDNAs with Homology to the Yeast SIR2 Gene: Sir2-like Proteins (Sirtuins) Metabolize NAD and May Have Protein ADP-Ribosyltransferase Activity. Biochem Biophys Res Commun 1999;260:273-79.

Frye, Phylogenetic classification of prokaryotic and eukaryotic Sir2-like proteins. Biochem Biophys Res Commun. Jul. 5, 2000;273(2):793-8.

Furukawa et al., Isolation and mapping of a human gene (RPD3L1) that is homologous to RPD3, a transcription factor in Saccharomyces cerevisiae. Cytogenet Cell Genet. 1996;73(1-2):130-3.

Furumai et al., Potent histone deacetylase inhibitors built from trichostatin A and cyclic tetrapeptide antibiotics including trapoxin. Proc Natl Acad Sci U S A. Jan. 2, 2001;98(1):87-92.

Gallop et al., Applications of combinatorial technologies to drug discovery. 1. Background and peptide combinatorial libraries. J Med Chem. Apr. 29, 1994;37(9):1233-51.

Gammon et al., T cell determinant structure: cores and determinant envelopes in three mouse major histocompatibility complex haplotypes. J Exp Med. Mar. 1, 1991;173(3):609-17.

García-Mata et al., Characterization and dynamics of aggresome formation by a cytosolic GFP-chimera. J Cell Biol. Sep. 20, 1999;146(6):1239-54.

Garcia-Mata et al., Hassles with taking out the garbage: aggravating aggresomes. Traffic. Jun. 2002;3(6):388-96.

Garcia-Ramirez et al., Role of the histone "tails" in the folding of oligonucleosomes depleted of histone H1. J Biol Chem. Sep. 25, 1992;267(27):19587-95.

Gardlik et al., Vectors and delivery systems in gene therapy. Med Sci Monit. Apr. 2005;11(4):RA110-21. Epub Mar. 24, 2005.

Gartenberg, The Sir proteins of Saccharomyces cerevisiae: mediators of transcriptional silencing and much more. Curr Opin Microbiol. Apr. 2000;3(2):132-7.

Gelmetti et al., Aberrant recruitment of the nuclear receptor corepressor-histone deacetylase complex by the acute myeloid leukemia fusion partner ETO. Mol Cell Biol. Dec. 1998;18(12):7185-91.

Genbank Submission: NIH/NCBI, Accession No. AAA68286; GI: 348052, Henkin et al., Jun. 14, 1995.

GenBank Submission: NIH/NCBI, Accession No. AAD29046, Grozinger et al.; May 6, 1999.

GenBank Submission: NIH/NCBI, Accession No. AAD29048, Grozinger et al.; May 6, 1999.

GenBank Submission: NIH/NCBI, Accession No. AAF73428, Buggy et al.; Jun. 1, 2000.

GenBank Submission: NIH/NCBI, Accession No. AAP63491; Kieliszewski; Jun. 12, 2003.

GenBank Submission: NIH/NCBI, Accession No. AC_000143, Levy et al.; Jul. 29, 2011.

GenBank Submission: NIH/NCBI, Accession No. AC_000144, Levy et al.; Jul. 29, 2011.

GenBank Submission: NIH/NCBI, Accession No. AC_000149, Levy et al.; Jul. 29, 2011.

GenBank Submission: NIH/NCBI, Accession No. AC_000151, Levy et al.; Jul. 29, 2011.

GenBank Submission: NIH/NCBI, Accession No. AC000054, Burian et al.; Jul. 29, 2009.

(56) References Cited

OTHER PUBLICATIONS

GenBank Submission: NIH/NCBI, Accession No. AK290716, Wakamatsu et al.; Jan. 9, 2008.
GenBank Submission: NIH/NCBI, Accession No. AM270988, Pel et al.; Jun. 30, 2009.
GenBank Submission: NIH/NCBI, Accession No. AM270990, Pel et al.; Jun. 30, 2009.
GenBank Submission: NIH/NCBI, Accession No. BAA22957; GI:2564324; Ohara et al., Mar. 18, 1998.
GenBank Submission: NIH/NCBI, Accession No. BAA22957; GI:6635127; Ohara et al., Dec. 25, 1999.
GenBank Submission: NIH/NCBI, Accession No. BAA25526; GI: 3043724, Ohara et al., Apr. 10, 1998.
GenBank Submission: NIH/NCBI, Accession No. BC009676, Strausberg et al.; Jul. 15, 2006.
GenBank Submission: NIH/NCBI, Accession No. BC012499, Strausberg et al.; Oct. 7, 2003.
GenBank Submission: NIH/NCBI, Accession No. BC111735, Strausberg et al.; Jan. 17, 2006.
GenBank Submission: NIH/NCBI, Accession No. CM000257, Venter et al.; Jun. 29, 2009.
GenBank Submission: NIH/NCBI, Accession No. CM000261, Venter et al.; Jun. 29, 2009.
GenBank Submission: NIH/NCBI, Accession No. CM000262, Venter et al.; Jun. 29, 2009.
GenBank Submission: NIH/NCBI, Accession No. CM000263, Venter et al.; Jun. 29, 2009.
GenBank Submission: NIH/NCBI, Accession No. CM000270, Venter et al.; Jun. 29, 2009.
GenBank Submission: NIH/NCBI, Accession No. CM000663, Lander et al.; Jun. 29, 2009.
GenBank Submission: NIH/NCBI, Accession No. CU678487, Rual et al.; Feb. 19, 2008.
GenBank Submission: NIH/NCBI, Accession No. GL000006, Lander et al.; Jun. 29, 2009.
GenBank Submission: NIH/NCBI, Accession No. GL000052, Lander et al.; Jun. 29, 2009.
GenBank Submission: NIH/NCBI, Accession No. GL000099, Lander et al.; Jun. 29, 2009.
GenBank Submission: NIH/NCBI, Accession No. NC_000011, Taylor et al.; Jul. 29, 2011.
GenBank Submission: NIH/NCBI, Accession No. NC_000012, Scherer et al.; Jul. 29, 2011.
GenBank Submission: NIH/NCBI, Accession No. NC_000017, Zody et al.; Jul. 29, 2011.
GenBank Submission: NIH/NCBI, Accession No. NC_000019, Grimwood et al.; Jul. 29, 2011.
GenBank Submission: NIH/NCBI, Accession No. NM_001098202, Boulay et al.; Apr. 22, 2012.
GenBank Submission: NIH/NCBI, Accession No. NM_003173, Syreeni et al.; Apr. 28, 2012.
GenBank Submission: NIH/NCBI, Accession No. NM_006497, Boulay et al.; Apr. 22, 2012.
GenBank Submission: NIH/NCBI, Accession No. NM_012237, Krishnan et al.; Apr. 29, 2012.
GenBank Submission: NIH/NCBI, Accession No. NM_030593, Krishnan et al.; Apr. 29, 2012.
GenBank Submission: NIH/NCBI, Accession No. NM_033331, Peddibhotla et al.; Apr. 22, 2012.
GenBank Submission: NIH/NCBI, Accession No. NT_009775, Scherer et al.; Jul. 29, 2011.
GenBank Submission: NIH/NCBI, Accession No. NT_010663, Zody et al.; Jul. 29, 2011.
GenBank Submission: NIH/NCBI, Accession No. NT_166525, Pel; Jun. 1, 2011.
GenBank Submission: NIH/NCBI, Accession No. NW_001838015, Levy et al.; Jul. 29, 2011.
GenBank Submission: NIH/NCBI, Accession No. NW_001838459, Levy et al.; Jul. 29, 2011.
GenBank Submission: NIH/NCBI, Accession No. NW_001838477, Levy et al.; Jul. 29, 2011.
GenBank Submission: NIH/NCBI, Accession No. P56524; GI: 3024889, Ohara et al., Dec. 15, 1998.
GenBank Submission: NIH/NCBI, Accession No. Q48935; GI: 3023317, Sakurada et al., Apr. 20, 2010.
GenBank Submission; NIH/NCBI, Accession No. AB006626; GI:2564323, Ohara et al.; Mar. 18, 1998.
GenBank Submission; NIH/NCBI, Accession No. AB006626; GI:6635126, Ohara et al.; Dec. 25, 1999.
GenBank Submission; NIH/NCBI, Accession No. AF039241, Swensen.; Mar. 11, 2009.
GenBank Submission; NIH/NCBI, Accession No. AF132607, Grozinger et al.; May 6, 1999.
GenBank Submission; NIH/NCBI, Accession No. AF132608, Grozinger et al.; May 6, 1999.
GenBank Submission; NIH/NCBI, Accession No. AF132609, Grozinger et al.; May 6, 1999.
GenBank Submission; NIH/NCBI, Accession No. AF230097, Hu et al., May 31, 2000.
GenBank Submission; NIH/NCBI, Accession No. AF245664, Buggy et al.; Jun. 1, 2000.
GenBank Submission; NIH/NCBI, Accession No. AJ011972, Strom et al.; Oct. 19, 1998.
GenBank Submission; NIH/NCBI, Accession No. CAA09893.1, Strom et al.; Oct. 7, 2008.
GenBank Submission; NIH/NCBI, Accession No. NM_001015053.1, Seo et al.; Mar. 15, 2009.
GenBank Submission; NIH/NCBI, Accession No. NM_006037.3, Chabane et al.; Mar. 29, 2009.
GenBank Submission; NIH/NCBI, Accession No. NM_006044.2, Dhakal et al.; Mar. 15, 2009.
GenBank Submission; NIH/NCBI, Accession No. NM_014707, Muralidhar et al.; Mar. 11, 2011.
GenBank Submission; NIH/NCBI, Accession No. NM_018486, Bailey et al.; Mar. 11, 2011.
GenBank Submission; NIH/NCBI, Accession No. NM_032019, Bailey et al.; Mar. 12, 2011.
GenBank Submission; NIH/NCBI, Accession No. NM_058176, Muralidhar et al.; Feb. 27, 2011.
GenBank Submission; NIH/NCBI, Accession No. NM_058177, Tam et al.; May 7, 2010.
GenBank Submission; NIH/NCBI, Accession No. NM_178423, Muralidhar et al.; Mar. 13, 2011.
GenBank Submission; NIH/NCBI, Accession No. NM_178425, Muralidhar et al.; Feb. 27, 2011.
GenBank Submission; NIH/NCBI, Accession No. NP_001518, Campos et al.; Mar. 13, 2011.
GenBank Submission; NIH/NCBI, Accession No. NP_004955, Dong et al; Mar. 27, 2011.
GenBank Submission; NIH/NCBI, Accession No. NP_005465, Huynh; Mar. 11, 2011.
GenBank Submission; NIH/NCBI, Accession No. NP_006035; Aldana-Masangkay et al.; Mar. 13, 2011.
GenBank Submission; NIH/NCBI, Accession No. O15739, Loomis et al.; Oct. 31, 2006.
GenBank Submission; NIH/NCBI, Accession No. Q9Z2V5, Verdel et al.; Mar. 2, 2010.
GenBank Submission; NIH/NCBI, Accession No. Q9Z2V6, Verdel et al.; Mar. 2, 2010.
GenBank Submission; NIH/NCBI, Accession No. R64669, Wilson; May 26, 1995.
GenBank Submission; NIH/NCBI, Accession No. U31814, Yang et al.; Nov. 13, 1996.
GenBank Submission; NIH/NCBI, Accession No. U31814, Yang et al.; Nov. 14, 1996.
Geysen et al., Use of peptide synthesis to probe viral antigens for epitopes to a resolution of a single amino acid. Proc Natl Acad Sci U S A. Jul. 1984;81(13):3998-4002.
Giacomelli et al., Simple one-flask method for the preparation of hydroxamic acids. Org Lett. Jul. 24, 2003;5(15):2715-7.

(56) References Cited

OTHER PUBLICATIONS

Gordon et al., Applications of combinatorial technologies to drug discovery. 2. Combinatorial organic synthesis, library screening strategies, and future directions. J Med Chem. May 13, 1994;37(10):1385-401.

Gordon et al., Design of peptide derived amino alcohols as transition-state analog inhibitors of angiotensin converting enzyme. Biochem Biophys Res Commun. Jan. 16, 1985;126(1):419-26.

Görlich, Nuclear protein import. Curr Opin Cell Biol. Jun. 1997;9(3):412-9.

Gossler et al., Transgenesis by means of blastocyst-derived embryonic stem cell lines. Proc Natl Acad Sci U S A. Dec. 1986;83(23):9065-9.

Goy et al., Phase II study of proteasome inhibitor bortezomib in relapsed or refractory B-cell non-Hodgkin's lymphoma. J Clin Oncol. Feb. 1, 2005;23(4):667-75. Epub Dec. 21, 2004.

Gravemann et al., Hydroxamic acid and fluorinated derivatives of valproic acid: anticonvulsant activity, neurotoxicity and teratogenicity. Neurotoxicol Teratol. Sep.-Oct. 2008;30(5):390-4. doi: 10.1016/j.ntt.2008.03.060. Epub Mar. 19, 2008.

Gray et al., The human histone deacetylase family. Exp Cell Res. Jan. 15, 2001;262(2):75-83.

Green, When the products of oncogenes and anti-oncogenes meet. Cell. Jan. 13, 1989;56(1):1-3.

Gregoretti et al., Molecular evolution of the histone deacetylase family: functional implications of phylogenetic analysisJ Mol Biol. Apr. 16, 2004;338(1):17-31.

Gregory et al., Combination chemotherapy versus melphalan and prednisolone in the treatment of multiple myeloma: an overview of published trials. J Clin Oncol. Feb. 1992;10(2):334-42.

Griffiths et al., Human anti-self antibodies with high specificity from phage display libraries. EMBO J. Feb. 1993;12(2):725-34.

Grignani et al., Fusion proteins of the retinoic acid receptor-alpha recruit histone deacetylase in promyelocytic leukaemia. Nature. Feb. 19, 1998;391(6669):815-8.

Grozinger et al., Deacetylase enzymes: biological functions and the use of small-molecule inhibitors. Chem Biol. Jan. 2002;9(1):3-16.

Grozinger et al., Regulation of histone deacetylase 4 and 5 and transcriptional activity by 14-3-3-dependent cellular localization. Proc Natl Acad Sci U S A. Jul. 5, 2000;97(14):7835-40.

Grozinger et al., Three proteins define a class of human histone deacetylases related to yeast Had1p. Proc Natl Acad Sci U S A. Apr. 27, 1999;96(9):4868-73.

Grunstein, Histone acetylation in chromatin structure and transcription. Nature. Sep. 25, 1997;389(6649):349-52.

Grunstein, Molecular model for telomeric heterochromatin in yeast. Curr Opin Cell Biol. Jun. 1997;9(3):383-7.

Gu et al., Activation of p53 sequence-specific DNA binding by acetylation of the p53 C-terminal domain. Cell. Aug. 22, 1997;90(4):595-606.

Guarente, Sir2 links chromatin silencing, metabolism, and aging. Genes Dev. May 1, 2000;14(9):1021-6.

Guo et al., Protein tolerance to random amino acid change. Proc Natl Acad Sci U S A. Jun. 22, 2004;101(25):9205-10. Epub Jun. 14, 2004.

Habig et al., Glutathione S-transferases. The first enzymatic step in mercapturic acid formation. J Biol Chem. Nov. 25, 1974;249(22):7130-9.

Haggarty et al., Dissecting cellular processes using small molecules: identification of colchicine-like, taxol-like and other small molecules that perturb mitosis. Chem Biol. Apr. 2000;7(4):275-86.

Haggarty et al., Domain-selective small-molecule inhibitor of histone deacetylase 6 (HDAC6)-mediated tubulin deacetylation. Proc Natl Acad Sci U S A. Apr. 15, 2003;100(8):4389-94. Epub Apr. 3, 2003.

Haggarty et al., Mapping chemical space using molecular descriptors and chemical genetics: deacetylase inhibitors. Comb Chem High Throughput Screen. Nov. 2004;7(7):669-76.

Haggarty et al., Multidimensional chemical genetic analysis of diversity-oriented synthesis-derived deacetylase inhibitors using cell-based assays. Chem Biol. May 2003;10(5):383-96.

Hansen et al., Retinoblastoma and the progression of tumor genetics. Trends Genet. May 1988;4(5):125-8.

Hardwick et al., Rapamycin-modulated transcription defines the subset of nutrient-sensitive signaling pathways directly controlled by the Tor proteins. Proc Natl Acad Sci U S A. Dec. 21, 1999;96(26):14866-70.

Hassig et al., A role for histone deacetylase activity in HDAC1-mediated transcriptional repression. Proc Natl Acad Sci U S A. Mar. 31, 1998;95(7):3519-24.

Hassig et al., Histone deacetylase activity is required for full transcriptional repression by mSin3A. Cell. May 2, 1997;89(3):341-7.

Hassig et al., Nuclear histone acetylases and deacetylases and transcriptional regulation: HATs off to HDACs. Curr Opin Chem Biol. Oct. 1997;1(3):300-8.

Hathaway et al., Dissecting cell biology with chemical scalpels. Curr Opin Cell Biol. Feb. 2005;17(1):12-9.

Hay et al., Histone deacetylase. Association with a nuclease resistant, high molecular weight fraction of HeLa cell chromatin. J Biol Chem. Mar. 25, 1983;258(6):3726-34.

Hayes et al., Histones H2A/H2B inhibit the interaction of transcription factor IIIA with the *Xenopus borealis* somatic 5S RNA gene in a nucleosome. Proc Natl Acad Sci U S A. Feb. 15, 1992;89(4):1229-33.

He et al., Distinct interactions of PML-RARalpha and PLZF-RARalpha with co-repressors determine differential responses to RA in APL. Nat Genet. Feb. 1998;18(2):126-35.

Hearn et al., Palindromic dihydrazones from N-aminophthalimide. J Chem Eng Data. 1986;31(2):255-6.

Hecht et al., Histone H3 and H4 N-termini interact with SIR3 and SIR4 proteins: a molecular model for the formation of heterochromatin in yeast. Cell. Feb. 24, 1995;80(4):583-92.

Hicks et al., Protein import into the nucleus: an integrated view. Annu Rev Cell Dev Biol. 1995;11:155-88.

Hideshima et al., Antitumor activity of lysophosphatidic acid acyltransferase-beta inhibitors, a novel class of agents, in multiple myeloma. Cancer Res. Dec. 1, 2003;63(23):8428-36.

Hideshima et al., Molecular mechanisms mediating antimyeloma activity of proteasome inhibitor PS-341. Blood. Feb. 15, 2003;101(4):1530-4. Epub Sep. 26, 2002.

Hideshima et al., Molecular mechanisms of novel therapeutic approaches for multiple myeloma. Nat Rev Cancer. Dec. 2002;2(12):927-37.

Hideshima et al., NF-κb as a therapeutic target in multiple myeloma. J Biol Chem. May 10, 2002;277(19):16639-47. Epub Feb. 28, 2002.

Hideshima et al., Novel therapeutic approaches for multiple myeloma. Immunol Rev. Aug. 2003;194:164-76.

Hideshima et al., p38 MAPK inhibition enhances PS-341 (bortezomib)-induced cytotoxicity against multiple myeloma cells. Oncogene. Nov. 18, 2004;23(54):8766-76.

Hideshima et al., Proteasome inhibitor PS-341 abrogates IL-6 triggered signaling cascades via caspase-dependent downregulation of gp130 in multiple myeloma. Oncogene. Nov. 20, 2003;22(52):8386-93.

Hideshima et al., Small-molecule inhibition of proteasome and aggresome function induces synergistic antitumor activity in multiple myeloma. Proc Natl Acad Sci U S A. Jun. 14, 2005;102(24):8567-72. Epub Jun. 3, 2005.

Hideshima et al., The proteasome inhibitor PS-341 inhibits growth, induces apoptosis, and overcomes drug resistance in human multiple myeloma cells. Cancer Res. Apr. 1, 2001;61(7):3071-6.

Hideshima et al., The role of tumor necrosis factor alpha in the pathophysiology of human multiple myeloma: therapeutic applications. Oncogene. Jul. 27, 2001;20(33):4519-27.

Hochuli et al., New metal chelate adsorbent selective for proteins and peptides containing neighbouring histidine residues. J Chromatogr. Dec. 18, 1987;411:177-84.

Hostein et al., Inhibition of signal transduction by the Hsp90 inhibitor 17-allylamino-17-demethoxygeldanamycin results in cytostasis and apoptosis. Cancer Res. May 15, 2001;61(10):4003-9.

Houdebine, The methods to generate transgenic animals and to control transgene expression. J Biotechnol. Sep. 25, 2002;98(2-3):145-60.

(56) References Cited

OTHER PUBLICATIONS

Houghten et al., Simplified procedure for carrying out simultaneous multiple hydrogen fluoride cleavages of protected peptide resins. Int J Pept Protein Res. Jun. 1986;27(6):673-8.

Houghten, General method for the rapid solid-phase synthesis of large numbers of peptides: specificity of antigen-antibody interaction at the level of individual amino acids. Proc Natl Acad Sci U S A. Aug. 1985;82(15):5131-5.

Hu et al., Cloning and characterization of a novel human class I histone deacetylase that functions as a transcription repressor. J Biol Chem. May 19, 2000;275(20):15254-64.

Huang et al., Nuclear receptor corepressors partner with class II histone deacetylases in a Sin3-independent repression pathway. Genes Dev. Jan. 1, 2000;14(1):45-54.

Huang et al., Vaccinia virus recombinants expressing an 11-kilodalton beta-galactosidase fusion protein incorporate active beta-galactosidase in virus particles. J Virol. Oct. 1988;62(10):3855-61.

Hubbert et al., HDAC6 is a microtubule-associated deacetylase. Nature. May 23, 2002;417(6887):455-8.

Hunter et al., An Enantioselective Synthesis of Benzylidene-Protected syn-3,5-Dihydroxy Carboxylate Esters via Osmium, Palladium, and Base Catalysis. Org Letter. 2001;3(7):1049-52.

Hynes, Hydroxylamine derivatives as potential antimalarial agents. 1. Hydroxamic acids. J Med Chem. Nov. 1970;13(6):1235-7.

Ike et al., Solid phase synthesis of polynucleotides. VIII. Synthesis of mixed oligodeoxyribonucleotides by the phosphotriester solid phase method. Nucleic Acids Res. Jan. 25, 1983;11(2):477-88.

Imai et al., Transcriptional silencing and longevity protein Sir2 is an NAD-dependent histone deacetylase. Nature. Feb. 17, 2000;403(6771):795-800.

Imamoto et al., Preparation and Synthetic Use of Trimethylsilyl Polyphosphate. A New Stereoselective Aldol-Type Reaction in the Presence of Trimethylsilyl Polyphosphate. J Org Chem. 1984;49:1105-10.

Imamoto et al., The Reaction of Aryl Methyl Ketones with Aromatic Aldehydes in Trimethylsilyl Polyphosphate (PPSE). Formation of MESO-2,4,6-Trisubstituted-5-ACYL-1,3-Dioxl. Tetrahedron Letters. 1982;23(14):1467-70.

Imhof et al., Acetylation of general transcription factors by histone acetyltransferases. Curr Biol. Sep. 1, 1997;7(9):689-92.

Itakura et al., Expression in *Escherichia coli* of a Chemically Synthesized Gene for the Hormone Somatostatin. Science. 1984;198:1056-63.

Itakura et al., Synthesis and use of synthetic oligonucleotides. Annu Rev Biochem. 1984;53:323-56.

Iwabuchi et al., Use of the two-hybrid system to identify the domain of p53 involved in oligomerization. Oncogene. Jun. 1993;8(6):1693-6.

Jacobs et al., Combinatorial chemistry—applications of light-directed chemical synthesis. Trends Biotechnol. Jan. 1994;12(1):19-26.

Jaenisch, Germ line integration and Mendelian transmission of the exogenous Moloney leukemia virus. Proc Natl Acad Sci U S A. Apr. 1976;73(4):1260-4.

Jaenisch, Transgenic animals. Science. Jun. 10, 1988;240(4858):1468-74.

Jähner et al., De novo methylation and expression of retroviral genomes during mouse embryogenesis. Nature. Aug. 12, 1982;298(5875):623-8.

Jähner et al., Insertion of the bacterial gpt gene into the germ line of mice by retroviral infection. Proc Natl Acad Sci U S A. Oct. 1985;82(20):6927-31.

Janknecht et al., Rapid and efficient purification of native histidine-tagged protein expressed by recombinant vaccinia virus. Proc Natl Acad Sci U S A. Oct. 15, 1991;88(20):8972-6.

Jin et al., Transcriptional regulation of the MDR1 gene by histone acetyltransferase and deacetylase is mediated by NF-Y. Mol Cell Biol. Jul. 1998;18(7):4377-84.

Johnson et al., Deacetylase activity associates with topoisomerase II and is necessary for etoposide-induced apoptosis. J Biol Chem. Feb. 16, 2001;276(7):4539-42. Epub Jan. 2, 2001.

Johnson et al., Genetic evidence for an interaction between SIR3 and histone H4 in the repression of the silent mating loci in *Saccharomyces cerevisiae*. Proc Natl Acad Sci U S A. Aug. 1990;87(16):6286-90.

Johnson et al., Molecular cloning of *Drosophila melanogaster* cDNAs that encode a novel histone deacetylase dHDAC3. Gene. Oct. 9, 1998;221(1):127-34.

Johnston et al., Aggresomes: a cellular response to misfolded proteins. J Cell Biol. Dec. 28, 1998;143(7):1883-98.

Johnstone, Histone-deacetylase inhibitors: novel drugs for the treatment of cancer. Nat Rev Drug Discov. Apr. 2002;1(4):287-99.

Jones et al., Probing the elusive catalytic activity of vertebrate class IIa histone deacetylases. Bioorg Med Chem Lett. Mar. 15, 2008;18(6):1814-9. Epub Feb. 14, 2008.

Jung et al., Amide analogues of trichostatin A as inhibitors of histone deacetylase and inducers of terminal cell differentiation. J Med Chem. Nov. 4, 1999;42(22):4669-79.

Junn et al., Parkin accumulation in aggresomes due to proteasome impairment. J Biol Chem. Dec. 6, 2002;277(49):47870-7. Epub Oct. 2, 2002.

Kao et al., Isolation of a novel histone deacetylase reveals that class I and class II deacetylases promote SMRT-mediated repression. Genes Dev. Jan. 1, 2000;14(1):55-66.

Kappel et al., Regulating gene expression in transgenic animals. Curr Opin Biotechnol. Oct. 1992;3(5):548-53.

Katoh et al., MAFFT: a novel method for rapid multiple sequence alignment based on fast Fourier transform. Nucleic Acids Res. Jul. 15, 2002;30(14):3059-66.

Kawaguchi et al., The deacetylase HDAC6 regulates aggresome formation and cell viability in response to misfolded protein stress. Cell. Dec. 12, 2003;115(6):727-38.

Kelly et al., Phase I clinical trial of histone deacetylase inhibitor: suberoylanilide hydroxamic acid administered intravenously. Clin Cancer Res. Sep. 1, 2003;9(10 Pt 1):3578-88.

Kennedy et al., Redistribution of silencing proteins from telomeres to the nucleolus is associated with extension of life span in *S. cerevisiae*. Cell. May 2, 1997;89(3):381-91.

Kerr et al., Encoded Combinatorial Peptide Libraries Containing Non-Natural Amino Acids. J Am Chem, Soc. 1993;115:2529-31.

Khockbin et al., Functional significance of histone deacetylase diversity. Curr Opin Genet Dev. Apr. 2011;11(2):162-6.

Khomutov et al., Directed synthesis of inhibitors of enzymic changes of glutamic acid. Doklady Akademii Nauk SSSR. 1965;161(5):1227-30. Russian.

Kijima et al., Trapoxin, an antitumor cyclic tetrapeptide, is an irreversible inhibitor of mammalian histone deacetylase. J Biol Chem. Oct. 25, 1993;268(30):22429-35.

Kikuchi et al., Multiplicity of histone deacetylase from calf thymus. FEBS Lett. Feb. 1, 1973;29(3):280-282.

Kleff et al., Identification of a gene encoding a yeast histone H4 acetyltransferase. J Biol Chem. Oct. 20, 1995;270(42):24674-7.

Koeller et al., Chemical genetic modifier screens: small molecule trichostatin suppressors as probes of intracellular histone and tubulin acetylation. Chem Biol. May 2003;10(5):397-410.

Kohler et al., Continuous cultures of fused cells secreting antibody of predefined specificity. Nature. Aug. 7, 1975;256(5517):495-7.

Kopito et al., Aggresomes and Russell bodies. Symptoms of cellular indigestion? EMBO Rep. Sep. 2000;1(3):225-31.

Kopito, Aggresomes, inclusion bodies and protein aggregation. Trends Cell Biol. Dec. 2000;10(12):524-30.

Kouzarides, Acetylation: a regulatory modification to rival phosphorylation? EMBO J. Mar. 15, 2000;19(6):1176-9.

Kozbar et al., The production of monoclonal antibodies from human lymphocytes. Immunology Today. 1983;4:72-79.

Krieger et al., Chemical studies of histone acetylation. Substrate specificity of a histone deacetylase from calf thymus nuclei. J Biol Chem. Jan. 10, 1974;249(1):332-4.

Kumar et al., MEGA: a biologist-centric software for evolutionary analysis of DNA and protein sequences. Brief Bioinform. Jul. 2008;9(4):299-306. Epub Apr. 16, 2008.

(56) References Cited

OTHER PUBLICATIONS

Kuruvilla et al., Dissecting glucose signaling with diversity-oriented synthesis and small-molecule microarrays. Nature. Apr. 11, 2002;416(6881):653-7.
Kwon et al., Depudecin induces morphological reversion of transformed fibroblasts via the inhibition of histone deacetylase. Proc Natl Acad Sci U S A. Mar. 31, 1998;95(7):3356-61.
Lahm et al., Unraveling the hidden catalytic activity of vertebrate class IIa histone deacetylases. Proc Natl Acad Sci U S A. Oct. 30, 2007;104(44):17335-40. Epub Oct. 23, 2007.
Lam et al., The "One-Bead-One-Compound" Combinatorial Library Method. Chem Rev. Apr. 1, 1997;97(2):411-48.
Landegren et al., A ligase-mediated gene detection technique. Science. Aug. 26, 1988;241(4869):1077-80.
Landry et al., the silencing protein SIR2 and its homologs are NAD-dependent protein deacetylases. Proc Natl Acad Sci U S A. May 23, 2000;97(11):5807-11.
Lasko et al., Targeted oncogene activation by site-specific recombination in transgenic mice. Proc Natl Acad Sci U S A. Jul. 15, 1992;89(14):6232-6.
Lee et al., A positive role for histone acetylation in transcription factor access to nucleosomal DNA. Cell. Jan. 15, 1993;72(1):73-84.
Lee et al., A Strategy for Macrocyclic Ring Closure and Functionalization Aimed toward Split-Pool Syntheses. J Am Chem Soc. 1999;121(45):10648-49.
Lee et al., Histone acetyltransferase complexes: one size doesn't fit all. Nat Rev Mol Cell Biol. Apr. 2007;8(4):284-95.
Lee et al., Proteasome inhibitors disrupt the unfolded protein response in myeloma cells. Proc Natl Acad Sci U S A. Aug. 19, 2003;100(17):9946-51. Epub Aug. 5, 2003.
Lin et al., Combination of proteasome and HDAC inhibitors for uterine cervical cancer treatment.Clin Cancer Res. Jan. 15, 2009;15(2):570-7.
Lin et al., Generation and Aldol Reaction of Endlate Anion Adjacnet to a η3-Allyl-Mo(Co)2Cp Moiety. A New Approach to the Stereoselctive Synthesis of 1,3,5-Triol and 2-Vinyl-3-Hydroxyl-Tetrahydrofuran. Tetrahedron Letters.1990;31(52):7645-48.
Lin et al., Role of the histone deacetylase complex in acute promyelocytic leukaemia. Nature. Feb. 19, 1998;391(6669):811-4.
Lizcano et al., Cell type-specific roles of histone deacetylase in TR ligand-independent transcriptional repression. Mol Cell Endocrinol. Feb. 14, 2001;172(1-2):13-20.
Look et al., Methods for Combinatorial Organic Synthesis: The Use of Fast 13C NMR Analysis for Gel Phase Reaction Monitoring. J Org Chem. 1994;59:7588-90.
Lopez-Girona et al., Nuclear localization of Cdc25 is regulated by DNA damage and a 14-3-3 protein. Nature. Jan. 14, 1999;397(6715):172-5.
Luger et al., Crystal structure of the nucleosome core particle at 2.8 A resolution. Nature. Sep. 18, 1997;389(6648):251-60.
Lutterbach et al., ETO, a target of t(8;21) in acute leukemia, interacts with the N-CoR and mSin3 corepressors. Mol Cell Biol. Dec. 1998;18(12):7176-84.
MacBeath et al., Printing proteins as microarrays for high-throughput function determination. Science. Sep. 8, 2000;289(5485):1760-3.
Macherla et al., Structure-activity relationship studies of salinosporamide A (NPI-0052), a novel marine derived proteasome inhibitor. J Med Chem. Jun. 2, 2005;48(11):3684-7.
Maddry et al., Inhibition of the Her2 Tyrosine Kinase and Characterization of a Hydrophobic Site Near the Nucleotide Binding Domain. Bioorganic Med Chem Letter. 1997;7(16):2109-14.
Madura et al., N-recognin/Ubc2 interactions in the N-end rule pathway. J Biol Chem. Jun. 5, 1993;268(16):12046-54.
Maeji et al., Multi-pin peptide synthesis strategy for T cell determinant analysis. J Immunol Methods. Nov. 6, 1990;134(1):23-33.
Magnaghi-Jaulin et al., Retinoblastoma protein represses transcription by recruiting a histone deacetylase. Nature. Feb. 5, 1998;391(6667):601-4.
Mahboobi et al., Design of chimeric histone deacetylase- and tyrosine kinase-inhibitors: a series of imatinib hybrides as potent inhibitors of wild-type and mutant BCR-ABL, PDGF-Rbeta, and histone deacetylases. J Med Chem. Apr. 23, 2009;52(8):2265-79.
Mai et al., Class II (IIa)-selective histone deacetylase inhibitors. 1. Synthesis and biological evaluation of novel (aryloxopropenyl)pyrrolyl hydroxyamides. J Med Chem. May 5, 2005;48(9):3344-53.
Manetto et al., Selective presence of ubiquitin in intracellular inclusions. Am J Pathol. Mar. 1989;134(3):505-13.
Marcand et al., Silencing of genes at nontelomeric sites in yeast is controlled by sequestration of silencing factors at telomeres by Rap1 protein. Genes Dev. Jun. 1, 1996;10(11):1297-309.
Marks et al., Histone deacetylases and cancer: causes and therapies. Nat Rev Cancer. Dec. 2001;1(3):194-202.
Marks et al., Histone deacetylases. Curr Opin Pharmacol. Aug. 2003;3(4):344-51.
Marks et al., Molecular evolution of proteins on filamentous phage. Mimicking the strategy of the immune system. J Biol Chem. Aug. 15, 1992;267(23):16007-10.
Marks et al., Polar/apolar chemical inducers of differentiation of transformed cells: strategies to improve therapeutic potential. Proc Natl Acad Sci U S A. Aug. 1989;86(16):6358-62.
Marmuse et al., "Click chemistry" en route to pseudo-starch. Org Biomol Chem. Jun. 21, 2005;3(12):2225-7. Epub May 11, 2005.
Martinelli et al., Molecular therapy for multiple myeloma. Haematologica. Sep. 2001;86(9):908-17.
Marushige et al., Template properties of liver chromatin. J Mol Biol. Jan. 1966;15(1):160-74.
Marx et al., Bench to bedside: the development of rapamycin and its application to stent restenosis. Circulation. Aug. 21, 2001;104(8):852-5.
Massa et al., Synthesis and antimicrobial and cytotoxic activities of pyrrole-containing analogues of trichostatin A. J Med Chem. Oct. 1990;33(10):2845-9.
McKenzie et al., The centromere and promoter factor, 1, CPF1, of *Saccharomyces cerevisiae* modulates gene activity through a family of factors including SPT21, RPD1 (SIN3), RPD3 and CCR4. Mol Gen Genet. Sep. 1993;240(3):374-86.
Megee et al., Genetic analysis of histone H4: essential role of lysines subject to reversible acetylation. Science. Feb. 16, 1990;247(4944):841-5.
Meinke et al., Histone deacetylase: a target for antiproliferative and antiprotozoal agents. Curr Med Chem. Feb. 2001;8(2):211-35.
Meinke et al., Synthesis of apicidin-derived quinolone derivatives: parasite-selective histone deacetylase inhibitors and antiproliferative agents. J Med Chem. Dec. 14, 2000;43(25):4919-22.
Menger et al., Chemical Reaction between Colliding Vesicles. Angew Chem Int Ed Engl. Oct. 15, 2001;40(20):3905-3907.
Merrifield, Solid Phase Peptide Syntheses. I. The Synthesis of a Tetrapeptide. J Am Chem Soc. 1963;85:2149-54.
Metzger et al., Ion-Spray Mass Spectrometry and High-Performance Liquid Chromatography—Mass Spectrometry of Synthetic Peptide Libraries. Angew Chem Int Ed Engl. 1993;32:894-96.
Miano et al., HDAC7 supports vascular integrity. Nat Med. Sep. 2006;12(9):997-8.
Miller et al., Histone deacetylase inhibitors. J Med Chem. Nov. 20, 2003;46(24):5097-116.
Miller et al., N-terminal methionine-specific peptidase in *Salmonella typhimurium*. Proc Natl Acad Sci U S A. May 1987;84(9):2718-22.
Minucci et al., Histone deacetylase inhibitors and the promise of epigenetic (and more) treatments for cancer. Nat Rev Cancer. Jan. 2006;6(1):38-51.
Miska et al., HDAC4 deacetylase associates with and represses the MEF2 transcription factor. EMBO J. Sep. 15, 1999;18(18):5099-107.
Mitchison, Towards a pharmacological genetics. Chem Biol. Sep. 1994;1(1):3-6.
Mitsiades et al., Inhibition of the insulin-like growth factor receptor-1 tyrosine kinase activity as a therapeutic strategy for multiple myeloma, other hematologic malignancies, and solid tumors. Cancer Cell. Mar. 2004;5(3):221-30.
Mitsiades et al., Molecular sequelae of histone deacetylase inhibition in human malignant B cells. Blood. May 15, 2003;101(10):4055-62. Epub Jan. 16, 2003.

(56) References Cited

OTHER PUBLICATIONS

Mitsiades et al., Molecular sequelae of proteasome inhibition in human multiple myeloma cells. Proc Natl Acad Sci U S A. Oct. 29, 2002;99(22):14374-9. Epub Oct. 21, 2002.
Mitsiades et al., Novel biologically based therapies for Waldenstrom's macroglobulinemia. Semin Oncol. Apr. 2003;30(2):309-12.
Mitsiades et al., The proteasome inhibitor PS-341 potentiates sensitivity of multiple myeloma cells to conventional chemotherapeutic agents: therapeutic applications. Blood. Mar. 15, 2003;101(6):2377-80. Epub Nov. 7, 2002.
Mitsiades et al., Transcriptional signature of histone deacetylase inhibition in multiple myeloma: biological and clinical implications. Proc Natl Acad Sci U S A. Jan. 13, 2004;101(2):540-5. Epub Dec. 26, 2003.
Moazed, Enzymatic activities of Sir2 and chromatin silencing. Curr Opin Cell Biol. Apr. 2001;13(2):232-8.
Mori et al., Synthesis of trichostatin A, a potent differentiation inducer of friend leukemic cells, and its antipode. Tetrahedron. 1988;44:6013-20.
Mottet et al., Histone deacetylase 7 silencing alters endothelial cell migration, a key step in angiogenesis. Circ Res. Dec. 7, 2007;101(12):1237-46. Epub Oct. 18, 2007.
Mowat et al., Rearrangements of the cellular p53 gene in erythroleukaemic cells transformed by Friend virus. Nature. Apr. 18-24, 1985;314(6012):633-6.
Mullins et al., Transgenesis in nonmurine species. Hypertension. Oct. 1993;22(4):630-3.
Munegumi et al., Amidation of carboxyl group involved in N-protected amino acids using O-benzylhydroxylamine. Peptide Chemistry. 1993;31:49-52.
Munshi et al., Acetylation of HMG I(Y) by CBP turns off IFN beta expression by disrupting the enhanceosome. Mol Cell. Oct. 1998;2(4):457-67.
Mutch et al., Effects of end groups on the stimulatory capacity of minimal length T cell determinant peptides. Pept Res. May-Jun. 1991;4(3):132-7.
Myers et al., Preparation of the Chiral, C-Protected α-Amino Aldehydes of High Optical Purity and Their Use as Condensation Components in a Linear Synthesis Strategy. J Am Chem Soc. 1999;121:8401-02.
Nagai et al., Synthesis of a Bicyclic Dipeptide with the Shape of β-Turn Central Part. Tetrahedron Lett. 1985;26:647-50.
Nagy et al., Nuclear receptor repression mediated by a complex containing SMRT, mSin3A, and histone deacetylase. Cell. May 2, 1997;89(3):373-80.
Nakatsuka et al., Total Synthesis of FK506 and an FKBP Probe Reagent, (C8, C9-13C2)-FK506. J. Am. Chem. Soc. 1990; 112:5583-5601.
Nakazawa et al., UV and skin cancer: specific p53 gene mutation in normal skin as a biologically relevant exposure measurement. Proc Natl Acad Sci U S A. Jan. 4, 1994;91(1):360-4.
Narang, DNA Synthesis. Tetrahedron. 1983;39:3-22.
Nardelii et al., A chemically defined synthetic vaccine model for HIV-1. J Immunol. Feb. 1, 1992;148(3):914-20.
Nasmyth et al., Both positive and negative regulators of HO transcription are required for mother-cell-specific mating-type switching in yeast. Cell. Feb. 27, 1987;48(4):579-87.
NCBI annotation project, GenBank Accession No. XM_002252, Oct. 16, 2001.
NCBI annotation project, GenBank Accession No. XM_004963, Feb. 9, 2001.
NCBI annotation project, GenBank Accession No. XM_004963.2, Oct. 16, 2001.
NCBI annotation project, GenBank Accession No. XM_007047, Nov. 16, 2000.
NCBI annotation project, GenBank Accession No. XM_008359, Oct. 16, 2001.
NCBI annotation project, GenBank Accession No. XP_002252, Oct. 16, 2001.
NCBI annotation project, GenBank Accession No. XP_008359.2, Feb. 10, 2001.
Needleman et al., A general method applicable to the search for similarities in the amino acid sequence of two proteins. J Mol Biol. Mar. 1970;48(3):443-53.
Needles et al., Generation and screening of an oligonucleotide-encoded synthetic peptide library. Proc Natl Acad Sci. 1993;90:10700-04.
Neer et al., The ancient regulatory-protein family of WD-repeat proteins. Nature. Sep. 22, 1994;371(6495):297-300.
Nefzi et al., The Current Status of Heterocyclic Combinatorial Libraries. Chem Rev. Apr. 1, 1997;97(2):449-472.
Nestler et al., A General Method for Molecular Tagging of Encoded Combinatorial Chemistry Libraries. J Org Chem. 1994;59:4723-24.
Newman et al., The influence of natural products upon drug discovery. Nat Prod Rep. Jun. 2000;17(3):215-34.
Ng et al., Histone deacetylases: silencers for hire. Trends Biochem Sci. Mar. 2000;25(3):121-6.
Ngo et al., Computational complexity, protein structure prediction, and the ILeventhal paradox. In: The Protein Folding Problem and Tertiary Structure Prediction. Merz et al., eds, Birhauser, Boston, MA. 1994:433-506.
Nielsen et al., Crystal structure of a bacterial class 2 histone deacetylase homologue. J Mol Biol. Nov. 18, 2005;354(1):107-20. Epub Oct. 7, 2005.
Nielsen et al., Synthetic Methods for the Implementation of Encoded Combinatorial Chemistry. J Am Chem Soc. 1993;115:9812-13.
Nielsen et al., Toward Chemical Implementation of Encoded Combinatorial Libraries. Methods Compan Methods Enzymol. 1994;6:361-71.
Nikolaiev et al., Peptide-encoding for structure determination of nonsequenceable polymers within libraries synthesized and tested on solid-phase supports. Pept Res. May-Jun. 1993;6(3):161-70.
Noll, Characterization of macromolecules by constant velocity sedimentation. Nature. Jul. 22, 1967;215(5099):360-3.
Notterpek et al., PMP22 accumulation in aggresomes: implications for CMT1A pathology. Neurobiol Dis. Oct. 1999;6(5):450-60.
O'Connor, Developing new drugs for the treatment of lymphoma. European Journal of Haematology. 2005;75:150-58.
O'Gorman et al., Recombinase-mediated gene activation and site-specific integration in mammalian cells. Science. Mar. 15, 1991;251(4999):1351-5.
Ohlmeyer et al., Complex synthetic chemical libraries indexed with molecular tags. Proc Natl Acad Sci U S A. Dec. 1, 1993;90(23):10922-6.
Oliva et al., Histone hyperacetylation can induce unfolding of the nucleosome core particle. Nucleic Acids Res. May 11, 1990;18(9):2739-47.
Orban et al., Tissue- and site-specific DNA recombination in transgenic mice. Proc Natl Acad Sci U S A. Aug. 1, 1992;89(15):6861-5.
Park et al., Point mutations in the yeast histone H4 gene prevent silencing of the silent mating type locus HML. Mol Cell Biol. Sep. 1990;10(9):4932-4.
Parra et al., Protein kinase D1 phosphorylates HDAC7 and induces its nuclear export after T-cell receptor activation J Biol Chem. Apr. 8, 2005;280(14):13762-70. Epub Dec. 28, 2004.
Patani et al., Bioisosterism: A Rational Approach in Drug Design. Chem Rev. Dec. 19, 1996;96(8):3147-3176.
Pátek et al., Safety-catch anchoring linkage for synthesis of peptide amides by Boc/Fmoc strategu. Tetrahedron Lett. 1991;32:3891-94.
Patel et al., Identification and characterization of small molecule inhibitors of a class I histone deacetylase from *Plasmodium falciparum*. J Med Chem. Apr. 23, 2009;52(8):2185-7.
Pei et al., Synergistic induction of oxidative injury and apoptosis in human multiple myeloma cells by the proteasome inhibitor bortezomib and histone deacetylase inhibitors. Clin Cancer Res. Jun. 1, 2004;10(11):3839-52.
PubChemCompound, datasheet [online compound summary] Retrieved from the Internet: <URL:http://pubchem.ncbi.nlm.nih.gov/search/search.cgi> See CID 11593538, CID 4215571, CID 24701534, CID 24694283, CID 19936521, CID 137190, CID 144926, CID 24692493, CID 15952018, CID 11643995, etc.

(56) References Cited

OTHER PUBLICATIONS

Reuben et al., A new group of potent inducers of differentiation in murine erythroleukemia cells. Proc Natl Acad Sci U S A. Mar. 1976;73(3):862-6.
Richardson et al., A phase 2 study of bortezomib in relapsed, refractory myeloma. N Engl J Med. Jun. 26, 2003;348(26):2609-17.
Richon et al., A class of hybrid polar inducers of transformed cell differentiation inhibits histone deacetylases. Proc Natl Acad Sci U S A. Mar. 17, 1998;95(6):3003-7.
Richon et al., Histone deacetylase inhibitor selectively induces p21WAF1 expression and gene-associated histone acetylation. Proc Natl Acad Sci U S A. Aug. 29, 2000;97(18):10014-9.
Richon et al., Second generation hybrid polar compounds are potent inducers of transformed cell differentiation. Proc Natl Acad Sci U S A. Jun. 11, 1996;93(12):5705-8.
Riester et al., Members of the histone deacetylase superfamily differ in substrate specificity towards small synthetic substrates. Biochem Biophys Res Commun. Nov. 19, 2004;324(3):1116-23.
Rine et al., Four genes responsible for a position effect on expression from HML and HMR in *Saccharomyces cerevisiae*. Genetics. May 1987;116(1):9-22.
Rittinger et al., Structural analysis of 14-3-3 phosphopeptide complexes identifies a dual role for the nuclear export signal of 14-3-3 in ligand binding. Mol Cell. Aug. 1999;4(2):153-66.
Roberts et al., Directed evolution of a protein: selection of potent neutrophil elastase inhibitors displayed on M13 fusion phage. Proc Natl Acad Sci U S A. Mar. 15, 1992;89(6):2429-33.
Robertson et al., Germ-line transmission of genes introduced into cultured pluripotential cells by retroviral vector. Nature. Oct. 2-8, 1986;323(6087):445-8.
Rosato et al., Histone deacetylase inhibitors in clinical development. Expert Opin Investig Drugs. Jan. 2004;13(1):21-38.
Rudinger, Characteristics of the amino acids as components of a peptide hormone sequence. In: Peptide Hormones. J.A. Parsons, ed. University Park Press, Baltimore, MD. 1976;1-7.
Rundlett et al., HDA1 and RPD3 are members of distinct yeast histone deacetylase complexes that regulate silencing and transcription. Proc Natl Acad Sci U S A. Dec. 10, 1996;93(25):14503-8.
Ruygrok et al., Rapamycin in cardiovascular medicine. Intern Med J. Mar. 2003;33(3):103-9.
Saikachi et al., Synthesis of Furan Derivatives. XV. 5-Nitrofuryl Polyene Aldehydes. J Am Chem Soc. 1958;80:3642-45.
Saitou et al., The neighbor-joining method: a new method for reconstructing phylogenetic trees. Mol Biol Evol. Jul. 1987;4(4):406-25.
Sanchez Del Pino et al., Properties of the yeast nuclear histone deacetylase. Biochem J. Nov. 1, 1994;303 ( Pt 3):723-9.
Sarraf et al., Rhodium-catalyzed formylation of organomercurials: application to efficient polyol synthesis. Org Lett. Oct. 5, 2000;2(20):3205-8.
Sasaki et al., Ligand-induced recruitment of a histone deacetylase in the negative-feedback regulation of the thyrotropin beta gene. EMBO J. Oct. 1, 1999;18(19):5389-98.
Sato et al., Synthesis and Antibiotic Activity of a Gramicidin S Analogue containing Bicyclic β-Turn Dipeptides. J Chem Soc Perkin Trans. 1986;1:1231-34.
Sawa et al., Histone deacetylase inhibitors such as sodium butyrate and trichostatin A induce apoptosis through an increase of the bcl-2-related protein Bad. Brain Tumor Pathol. 2001;18(2):109-14.
Schena, Quantitative Monitoring of Gene Expression Patterns with a Complementary DNA Microarray. Science. 1995;270:467-70.
Schlienger et al., Human immunodeficiency virus type 1 major neutralizing determinant exposed on hepatitis B surface antigen particles is highly immunogenic in primates. J Virol. Apr. 1992;66(4):2570-6.
Schmidt et al., Rapid determination of methadone in plasma, cerebrospinal fluid, and urine by gas chromatography and its application to routine drug monitoring. Pharm Res. Mar. 1993;10(3):441-4.
Schreiber, Chemical genetics resulting from a passion for synthetic organic chemistry. Bioorg Med Chem. Aug. 1998;6(8):1127-52.

Schreiber, Target-oriented and diversity-oriented organic synthesis in drug discovery. Science. Mar. 17, 2000;287(5460):1964-9.
Schreiber, Using the Principles of Organic Chemistry to Explore Cell Biology. Chem and Eng News. 1992; 70(43): 22-32.
Schuetz et al., Human HDAC7 harbors a class IIa histone deacetylase-specific zinc binding motif and cryptic deacetylase activity. J Biol Chem. Apr. 25, 2008;283(17):11355-63. Epub Feb. 19, 2008.
Scott et al., Searching for peptide ligands with an epitope library. Science. Jul. 27, 1990;249(4967):386-90.
Secrist et al., HDAC inhibitors for the treatment of cancer. Curr Opin Investig Drugs. Dec. 2003;4(12):1422-7.
Seffernick et al., Melamine deaminase and atrazine chlorohydrolase: 98 percent identical but functionally different. J Bacteriol. Apr. 2001;183(8):2405-10.
Serrador et al., HDAC6 deacetylase activity links the tubulin cytoskeleton with immune synapse organization. Immunity. Apr. 2004;20(4):417-28.
Shpaer, GeneAssist. Smith-Waterman and other database similarity searches and identification of motifs. Methods Mol Biol. 1997;70:173-87.
Sikorski et al., A system of shuttle vectors and yeast host strains designed for efficient manipulation of DNA in *Saccharomyces cerevisiae*. Genetics. May 1989;122(1):19-27.
Singh et al., Chemistry and structure-activity relationship of HIV-1 integrase inhibitor integracide B and related natural products. J Nat Prod. Oct. 2003;66(10):1338-44.
Smith et al., A phylogenetically conserved Nad+-dependent protein deacetylase activity in the Sir2 protein family. Proc Natl Acad Sci U S A. Jun. 6, 2000;97(12):6658-63.
Smith et al., Comparison of biosequences. Adv Appl Math. 1981;2:482-89.
Smith et al., Mechanisms and molecular probes of sirtuins. Chem Biol. Oct. 20, 2008;15(10):1002-13.
Somoza et al., Structural snapshots of human HDAC8 provide insights into the class I histone deacetylases. Structure. Jul. 2004;12(7):1325-34.
Stamatakis et al., A rapid bootstrap algorithm for the RAxML Web servers. Syst Biol. Oct. 2008;57(5):758-71.
Sternson et al., Split-pool synthesis of 1,3-dioxanes leading to arrayed stock solutions of single compounds sufficient for multiple phenotypic and protein-binding assays. J Am Chem Soc. Feb. 28, 2001;123(8):1740-7.
Sternson et al., Synthesis of 7200 small molecules based on a substructural analysis of the histone deacetylase inhibitors trichostatin and trapoxin. Org Lett. Dec. 27, 2001;3(26):4239-42.
Stevanovic et al., Natural and Synthetic Peptide Pools: Characterization by Sequencing and Electrospray Mass Spectrometry. Bioorg Med Chem Lett. 1993;3(3):431-36.
Stewart et al., Expression of retroviral vectors in transgenic mice obtained by embryo infection. EMBO J. Feb. 1987;6(2):383-8.
Stillman et al., Epistasis analysis of suppressor mutations that allow HO expression in the absence of the yeast SW15 transcriptional activator. Genetics. Mar. 1994;136(3):781-8.
Stowell et al., The synthesis of N-hydroxy-N'-phenyloctanediamide and its inhibitory effect on proliferation of AXC rat prostate cancer cells. J Med Chem. Apr. 14, 1995;38(8):1411-3.
Strebhardt et al., Additional member of the protein-tyrosine kinase family: the src- and lck-related protooncogene c-tkl. Proc Natl Acad Sci U S A. Dec. 1987;84(24):8778-82.
Sullivan et al., Localization of the BiP molecular chaperone with respect to endoplasmic reticulum foci containing the cystic fibrosis transmembrane conductance regulator in yeast. J Histochem Cytochem. Apr. 2003;51(4):545-8.
Suzuki et al., Synthesis and histone deacetylase inhibitory activity of new benzamide derivatives. J Med Chem. Jul. 29, 1999;42(15):3001-3.
Tallarico et al., An alkylsilyl-tethered, high-capacity solid support amenable to diversity-oriented synthesis for one-bead, one-stock solution chemical genetics. J Comb Chem. May-Jun. 2001;3(3):312-8.

(56) References Cited

OTHER PUBLICATIONS

Tan et al., Novel histone deacetylase inhibitors in clinical trials as anti-cancer agents. J Hematol Oncol. Feb. 4, 2010;3:5. doi: 10.1186/1756-8722-3-5. 13 pages.
Tan et al., Stereoselective Synthesis of over Two Million Compounds Having Structural Features Both Reminiscent of Natural Products and Compatible with Miniaturized Cell-Based Assays. J. Am. Chem. Soc. 1998; 120: 8565-66.
Tanaka et al., Syntheses and anti-inflammatory and analgesic activities of hydroxamic acids and acid hydrazides. Chem Pharm Bull (Tokyo). Aug. 1983;31(8):2810-9.
Tanner et al., Silent information regulator 2 family of NAD-dependent histone/protein deacetylases generates a unique product, 1-O-acetyl-ADP-ribose. Proc Natl Acad Sci U S A. Dec. 19, 2000;97(26):14178-82.
Tanny et al., Coupling of histone deacetylation to NAD breakdown by the yeast silencing protein Sir2: Evidence for acetyl transfer from substrate to an NAD breakdown product. Proc Natl Acad Sci U S A. Jan. 16, 2001;98(2):415-20. Epub Dec. 26, 2000.
Tao et al., Deacetylase inhibition promotes the generation and function of regulatory T cells. Nat Med. Nov. 2007;13(11):1299-307. Epub Oct. 7, 2007.
Taunton et al., A mammalian histone deacetylase related to the yeast transcriptional regulator Rpd3p. Science. Apr. 19, 1996;272(5260):408-11.
Taunton et al., Deacetylation. The Scientist. 1999;13:13.
Taunton et al., Synthesis of Natural and Modified Trapoxins, Useful Reagents for Exploring Histone Deacetylase Function. J Am Chem Soc. 1996;118:10412-22.
Thornton et al., Protein Engineering: Editorial Overview. Curr Opin Biotechnol. 1995;6(4):367-69.
Tissenbaum et al., Increased dosage of a sir-2 gene extends lifespan in *Caenorhabditis elegans*. Nature. Mar. 8, 2001;410(6825):227-30.
Tong et al., Chromatin deacetylation by an ATP-dependent nucleosome remodeling complex. Nature. 1997;395:917-21.
Tsang et al., CobB, a new member of the SIR2 family of eucaryotic regulatory proteins, is required to compensate for the lack of nicotinate mononucleotide:5,6-dimethylbenzimidazole phosphoribosyltransferase activity in cobT mutants during cobalamin biosynthesis in *Salmonella typhimurium* LT2. J Biol Chem. Nov. 27, 1998;273(48):31788-94.
Tsankova et al., Sustained hippocampal chromatin regulation in a mouse model of depression and antidepressant action. Nat Neurosci. Apr. 2006;9(4):519-25. Epub Feb. 26, 2006.
Turner, Decoding the nucleosome. Cell. Oct. 8, 1993;75(1):5-8.
Uchiyama et al., Adhesion of human myeloma-derived cell lines to bone marrow stromal cells stimulates interleukin-6 secretion. Blood. Dec. 15, 1993;82(12):3712-20.
UniProtKB/Swiss-Prot; Accession No. A8K8P3; Jun. 13, 2012.
UniProtKB/Swiss-Prot; Accession No. O15379; Dangond et al.; Apr. 18, 2012.
UniProtKB/Swiss-Prot; Accession No. Q13547; Taunton et al.; Apr. 18, 2012.
UniProtKB/Swiss-Prot; Accession No. Q8WU14; Strausberg et al.; Oct. 31, 2006.
UniProtKB/Swiss-Prot; Accession No. Q92769; Yang et al.; Apr. 18, 2012.
UniProtKB/Swiss-Prot; Accession No. Q9BY41; Hu et al.; Apr. 18, 2012.
UniProtKB/Swiss-Prot; Accession No. Q9UBN7; Grozinger et al.; Apr. 18, 2012.
UniProtKB/Swiss-Prot; Accession No. Q9UQL6; Grozinger et al.; Apr. 18, 2012.
Uong et al., Stereocontrolled Functionalization of Acyclic Molybdenum-η-Allyl Complexes: A New Approach to the Stereoselective Synthesis of 1,3-Diols. J Chem Soc Chem Commun. 1990:1285-87.
Urnov et al., Targeting of N-CoR and histone deacetylase 3 by the oncoprotein v-erbA yields a chromatin infrastructure-dependent transcriptional repression pathway. EMBO J. Aug. 1, 2000;19(15):4074-90.
Valerio et al., Multipin peptide synthesis at the micromole scale using 2-hydroxyethyl methacrylate grafted polyethylene supports. Int J Pept Protein Res. Jul. 1993;42(1):1-9.
Valerio et al., Synthesis of peptide analogues using the multipin peptide synthesis method. Anal Biochem. Aug. 15, 1991;197(1):168-77.
Van Der Krol et al., Modulation of eukaryotic gene expression by complementary RNA or DNA sequences. Biotechniques. Nov.-Dec. 1988;6(10):958-76.
Van Der Putten et al., Efficient insertion of genes into the mouse germ line via retroviral vectors. Proc Natl Acad Sci U S A. Sep. 1985;82(18):6148-52.
Vannini et al., Crystal structure of a eukaryotic zinc-dependent histone deacetylase, human HDAC8, complexed with a hydroxamic acid inhibitor. Proc Natl Acad Sci U S A. Oct. 19, 2004;101(42):15064-9. Epub Oct. 11, 2004.
Varga-Weisz et al., Chromatin-remodeling factors: machines that regulate? Curr Opin Cell Biol. Jun. 1998;10(3):346-53.
Vegas et al., Fluorous-based small-molecule microarrays for the discovery of histone deacetylase inhibitors. Angew Chem Int Ed Engl. 2007;46(42):7960-4.
Venter et al., The sequence of the human genome. Science. Feb. 16, 2001;291(5507):1304-51.
Verdel et al., Identification of a new family of higher eukaryotic histone deacetylases. Coordinate expression of differentiation-dependent chromatin modifiers. J Biol Chem. Jan. 22, 1999;274(4):2440-5.
Vidal et al., RPD3 encodes a second factor required to achieve maximum positive and negative transcriptional states in *Saccharomyces cerevisiae*. Mol Cell Biol. Dec. 1991;11(12):6317-27.
Vong et al., Regio- and Stereocontrolled Functionalization of Acyclic Molybdenum-η-Allyl Complexes. J Am Chem Soc. 1991;113:573-82.
Walker et al., Affinity chromatography of mammalian and yeast nucleosomes. Two modes of binding of transcriptionally active mammalian nucleosomes to organomercurial-agarose columns, and contrasting behavior of the active nucleosomes of yeast. J Biol Chem. Apr. 5, 1990;265(10):5736-46.
Wallace et al., Understanding cytochrome c function: engineering protein structure by semisynthesis. FASEB J. Apr. 1, 1993;7(6):505-15.
Wang et al., ETO, fusion partner in t(8;21) acute myeloid leukemia, represses transcription by interaction with the human N-CoR/mSin3/HDAC1 complex. Proc Natl Acad Sci U S A. Sep. 1, 1998;95(18):10860-5.
Wang et al., HDAC4, a human histone deacetylase related to yeast HDA1, is a transcriptional corepressor. Mol Cell Biol. Nov. 1999;19(11):7816-27.
Wang et al., Isolation of high-affinity peptide antagonists of 14-3-3 proteins by phage display. Biochemistry. Sep. 21, 1999;38(38):12499-504.
Wang et al., Zinc binding in HDAC inhibitors: a DFT study. J Org Chem. Jul. 6, 2007;72(14):5446-9. Epub Jun. 19, 2007.
Warrell et al., Therapeutic targeting of transcription in acute promyelocytic leukemia by use of an inhibitor of histone deacetylase. J Natl Cancer Inst. Nov. 4, 1998;90(21):1621-5.
Wegener et al., A fluorogenic histone deacetylase assay well suited for high-throughput activity screening. Chem Biol. Jan. 2003;10(1):61-8.
Weinberg, Finding the anti-oncogene. Sci Am. Sep. 1988;259(3):44-51.
Wennemers et al., Cyclooligomeric Receptors Based on Trimesic Acid and 1,2-Diamines. Minimal Structure for Sequence-Selective Peptide Binding. J Org Chem. 1995;60:1108-09.
Whelan et al., A general empirical model of protein evolution derived from multiple protein families using a maximum-likelihood approach. Mol Biol Evol. May 2001;18(5):691-9.
Wilen et al., Strategies in Optical Resolution. Tetrahedron. 1977;33:2725-36.
Witkowski et al., Conversion of a beta-ketoacyl synthase to a malonyl decarboxylase by replacement of the active-site cysteine with glutamine. Biochemistry. Sep. 7, 1999;38(36):11643-50.

(56) References Cited

OTHER PUBLICATIONS

Wong et al., Modular synthesis and preliminary biological evaluation of stereochemically diverse 1,3-dioxanes. Chem Biol. Sep. 2004;11(9):1279-91.

Wong et al., Structural biasing elements for in-cell histone deacetylase paralog selectivity. J Am Chem Soc. May 14, 2003;125(19):5586-7.

Workman et al., Alteration of nucleosome structure as a mechanism of transcriptional regulation. Annu Rev Biochem. 1998;67:545-79.

Xie et al., Sum1 and Hst1 repress middle sporulation-specific gene expression during mitosis in *Saccharomyces cerevisiae*. EMBO J. Nov. 15, 1999;18(22):6448-54.

Xu et al., Coactivator and corepressor complexes in nuclear receptor function. Curr Opin Genet Dev. Apr. 1999;9(2):140-7.

Xue et al., NURD, a novel complex with both ATP-dependent chromatin-remodeling and histone deacetylase activities. Mol Cell. Dec. 1998;2(6):851-61.

Yaffe et al., The structural basis for 14-3-3:phosphopeptide binding specificity. Cell. Dec. 26, 1997;91(7):961-71.

Yang et al., Cloning and characterization of two mouse genes with homology to the yeast Sir2 gene. Genomics. Nov. 1, 2000;69(3):355-69.

Yang et al., Isolation and characterization of cDNAs corresponding to an additional member of the human histone deacetylase gene family. J Biol Chem. Oct. 31, 1997;272(44):28001-7.

Yang et al., Maintenance of G2 arrest in the *Xenopus oocyte*: a role for 14-3-3-mediated inhibition of Cdc25 nuclear import. EMBO J. Apr. 15, 1999;18(8):2174-83.

Yang et al., Transcriptional repression by YY1 is mediated by interaction with a mammalian homolog of the yeast global regulator RPD3. Proc Natl Acad Sci U S A. Nov. 12, 1996;93(23):12845-50.

Yoon et al., Cyclooligomeric Receptors for the Sequence Selective Binding of Peptides. A Tetrahedral Receptor from the Trimesic Acid and 1,2-Diamines. Tetrahedron Lett. 1994;35:8557-60.

Yoshida et al., A novel tetracyclic peptide, trapoxin, induces phenotypic change from transformed to normal in sis-oncogene-transformed NIH3T3 cells. Jpn J Cancer Res. Apr. 1992;83(4):324-8.

Yoshida et al., Potent and specific inhibition of mammalian histone deacetylase both in vivo and in vitro by trichostatin A. J Biol Chem. Oct. 5, 1990;265(28):17174-9.

Yoshida et al., Trichostatin A and trapoxin: novel chemical probes for the role of histone acetylation in chromatin structure and function. Bioessays. May 1995;17(5):423-28.

Youngquist et al., Matrix-assisted laser desorption ionization for rapid determination of the sequences of biologically active peptides isolated from support-bound combinatorial peptide libraries. Rapid Commun Mass Spectrom. Jan. 1994;8(1):77-81.

Yu et al., The proteasome inhibitor bortezomib interacts synergistically with histone deacetylase inhibitors to induce apoptosis in Bcr/Abl+ cells sensitive and resistant to STI571. Blood. Nov. 15, 2003;102(10):3765-74. Epub Jul. 31, 2003.

Zervos et al., Mxi1, a protein that specifically interacts with Max to bind Myc-Max recognition sites. Cell. Jan. 29, 1993;72(2):223-32.

Zhang et al., The dermatomyositis-specific autoantigen Mi2 is a component of a complex containing histone deacetylase and nucleosome remodeling activities. Cell. Oct. 16, 1998;95(2):279-89.

Zhou et al., Cloning and characterization of a histone deacetylase, HDAC9. Proc Natl Acad Sci U S A. Sep. 11, 2001;98(19):10572-7. Epub Sep. 4, 2001.

Zhou et al., Identification of a transcriptional repressor related to the noncatalytic domain of histone deacetylases 4 and 5. Proc Natl Acad Sci U S A. Feb. 1, 2000;97(3):1056-61.

Zhu et al., Phosphine-catalyzed synthesis of 1,3-dioxan-4-ylidenes. Org Lett. Mar. 31, 2005;7(7):1387-90.

Zimmermann et al., Conformational and epitope mapping of herpes-simplex-virus type-1 thymidine kinase using synthetic peptide segments. Eur J Biochem. Sep. 1, 1991;200(2):519-28.

Perrod et al., A cytosolic NAD-dependent deacetylase, Hst2p, can modulate nucleolar and telomeric silencing in yeast. EMBO J. Jan. 15, 2001;20(1-2):197-209.

Peterson et al., Small molecule developmental screens reveal the logic and timing of vertebrate development. Proc Natl Acad Sci U S A. Nov. 21, 2000;97(24):12965-9.

Phillips, The challenge of gene therapy and DNA delivery. J Pharm Pharmacol. Sep. 2001;53(9):1169-74.

Posnett et al., A novel method for producing anti-peptide antibodies. Production of site-specific antibodies to the T cell antigen receptor beta-chain. J Biol Chem. Feb. 5, 1988;263(4):1719-25.

Powell et al., Anti-1,3-diols by Addition of Dialkylzinc Reagents to 4-Acetoxy-1,3-dioxanes. J Org Chem. Mar. 19, 1999;64(6):2026-2037.

Presbitero et al., Drug-eluting stents do they make the difference? Minerva Cardioangiol. Oct. 2002;50(5):431-42. Italian.

Probst et al., Human liver arylacetamide deacetylase. Molecular cloning of a novel esterase involved in the metabolic activation of arylamine carcinogens with high sequence similarity to hormone-sensitive lipase. J Biol Chem. Aug. 26, 1994;269(34):21650-6.

PubChemCompound, datasheet [online compound summary] Retrieved from the Internet: <URL:http://pubchem.ncbi.nlm.nih.gov/search/search.cgi> See CID 11593538, CID 4215571, CID 24701534, CID 24694283, CID 19936521, CID 137190, CID 144926, CID 24692493, CID 15952018, CID 11643995, etc. Jun. 24, 2013.

Pyne et al., Reactions of Lithiated N-Tosyl S-Phenyl S-2-Propenyl Sulfoximine with Aldehydes. Sulfur Letters. 1997;20(6):255-60.

Qian et al., A retinoblastoma-binding protein related to a negative regulator of Ras in yeast. Nature. Aug. 12, 1993;364(6438):648-52.

Raje et al., Combination of the mTOR inhibitor rapamycin and CC-5013 has synergistic activity in multiple myeloma. Blood. Dec. 15, 2004;104(13):4188-93. Epub Aug. 19, 2004.

Remiszewski, The discovery of NVP-LAQ824: from concept to clinic. Curr Med Chem. Nov. 2003;10(22):2393-402.

Renthal et al., Histone deacetylase 5 epigenetically controls behavioral adaptations to chronic emotional stimuli. Neuron. Nov. 8, 2007;56(3):517-29.

\* cited by examiner

HDAC4

MSSQSHPDGLSGRDQPVELLNPARVNHMPSTVDVATALPLQVAPSAVPMDLRLDHQFSLPVAEPALREQQLQELLALKQKQQIQRQILI 90
AEFQRQHEQLSRQHEAQLHEHIKQQQEMLAMKHQQELLEHQRKLERHRQEQELEKQHREQKLQQLKNKEKGKESAVASTEVKMKLQEFVL 180
NKKKALAHRNLNHCISSDPRYWYGKTQHSSLDQSSPPQSGVSTSYNHPVLGMYDAKDDFPLRKTASEPNLKLRSRLKQKVAERRSSPLLR 270
RKDGPVVTALKKRPLDVTDSACSSAPGSGPSSPNNSSGSVSAENGIAPAVPSIPAETSLAHRLVAREGSAAPLPLYTSPSLPNITLGLPA 360
TGPSAGTAGQQDTERLTLPALQQRLSLFPGTHLTPYLSTSPLERDGGAAHSPLLQHMVLLEQPPAQAPLVTGLGALPLHAQSLVGADRVS 450
PSIHKLRQHRPLGRTQSAPLPQNAQALQHLVIQQQHQQFLEKHKQQFQQQLQMNKIIPKPSEPARQPESHPEETEELREHQALLDEPY 540
LDRLPGQKEAHAQAGVQVKQEPIESDEEEAEPPREVEPGQRQPSEQELLFRQQALLLEQQRIHQLRNYQASMEAAGIPVSFGGHRPLSRA 630
QSSPASATFPVSVQEPPTKPRFTTGLVYDTIMLKHQCTCGSSSSHPEHAGRIQSIWSRLQETGLRGKCECIRGRKATLEELQTVHSEAHT 720
LLYGTNPLNRQKLDSKKLLGSLASVFVRLPCGGVGVDSDTIWNEVHSAGAARLAVGCVVELVFKVATGELKNGFAVVRPPGHHAEESTPM 810
GFCYFNSVAVAAKLLQQRLSVSKILIVDWDVHHGNGTQQAFYSDPSVLYMSLHERYDDGNFFPGSGAPDEVGTGPGVGFNVNMAFTGGLDP 900
PMGDAEYLAAFRTVVMPIASEFAPDVVLVSSGFDAVEGHPTPLGGYNLSARCFGYLTKQLMGLAGGRIVLALEGGHDLTAICDASEACVS 990
ALLGNELDPLPEKVLQQRPNANAVRSMEKVMEIHSKYWRCLQRTTSTAGRSLIEAQTCENEEAETVTAMASLSVGVKPAEKRPDEEPMEE 1080
EPPL.1085

FIG. 1A

HDAC5

MNSPNESDGMSGREPSLEILPRTSLHSIPVTVEVKPVLPRAMPSSMGGGGGGSPSPVELRGALVGSVDPTLREQQLQQELLALKQQQQLQ 90
KQLLFAEFQKQHDHLTRQHEVQLQKHLKQQQEMLAAKRQQELEQQRQREQQRQEELEKQRLEQQLLILRNKEKSKESAIAS 180
TEVKLRLQEFLLSKEPTPGGLNHSLPQHPKCWGAHHASLDQSSPPQSGPPGTPPSYKLPLPGPYDSRDDFPLRKTASEPNLKVRSRLK 270
QKVAERRSSPLLRRKDGTVISTFKKRAVEITGAGPGASSVCNSAPGSGPSSPNSSHSTIAENGFTGSVPNIPTEMLPQHERALPLDSSPNQ 360
FSLYTSPSLPNISLGLQATVTVTNSHLTASPKLSTQQEAERQALQSLRQGGTLTGKFMSTSSIPGCLLGVALEGDGSPHGHASLLQHVLL 450
LEQARQQSTLIAVPLHGQSPLVTGERVATSMRTVGKLPRHRPLSRTQSSPLPQSPQALQQLVMQQQHQQFLEKQKQQQLQLGKILTKTGE 540
LPRQPTTHPEETEEELTEQQEVLLGEGALTMPREGSTESESTQEDLEEEDEEEEDGEEEEDCIQVKDEEGESGAEEGPDLEEPGAGYKKLF 630
SDAQPLQPLQVYQAPLSLATVPEHQALGRTQSSPAAPGGMKSPPDQPVKHLFTTGVVYDTFMLKHQCMCGNTHVHPEHAGRIQSIWSRLQE 720
TGLLSKCERIRGRKATLDEIQTVHSEYHTLLYGTSPLNRQKLDSKKLLGPISQKMYAVLPCGGIGVDSDTVWNEMHSSSAVRMAVGCLLE 810
LAFKVAAGELKNGFAIIRPPGHHAEESTAMGFCFFNSVAITAKLLQQKLNVGKVLIVDWDIHHGNGTQQAFYNDPSVLYISLHRYDNGNF 900
FPGSGAPEEVGGGPGVGYNVNVAWTGGVDPPIGDVEYLTAFRTVVMPIAHEFSPDVVLVSAGFDAVEGHLSPLGGYSVTARCFGHLTRQL 990
MTLAGGRVVLALEGGHDLTAICDASEACVSALLSVELQPLDEAVLQQKPNINAVATLEKVIEIQSKHWSCVQKFAAGLGRSLREAQAGET 1080
EEAETVSAMALLSVGAEQAQAAAREHSPRPAEEPMEQEPAL 1122

FIG. 1B

HDAC6
MTSTGQDSTTTRQRRSRQNPQSPPQDSSVTSKRNIKKGAVPRSIPNLAEVKKKGKMKKLGQAMEEDLIVGLQGMDLNLEAEALAGTGLVL       90
DEQLNEFHCLWDDSFPEGPERLHAIKEQLIQEGLLDRCVSFQARFAEKEELMLVHSLEYIDLMETTQYMNEGELRVLADTYDSVYLHPNS      180
YSCACLASGSVLRLVDAVLGAEIRNGMAIIRPPGHHAQHSLMDGYCMFNHVAVAARYAQQKHRIRRVLIVDWDVHHGQGTQFFTFDQDPSV     270
LYFSIHRYEQGRFWPHLKASNWSTTGFGQGQGYTINVPWNQVGMRDADYIAAFLHVLLPVALEFQPQLVLVAAGFDALQGDPKGEMAATP      360
AGFAQLTHLLMGLAGGKLILSLEGGYNLRALAEGVSASLHTLLGDPCPMLESPGAPCRSAQASVSCALEALEPFWEVLVRSTETVERDNM     450
EEDNVEESEEGPWEPPVLPILTWPVLQSRTGLVYDQNMMNHCNLWDSHHPEVPQRILRIMCRLEELGLAGRCLTLTPRPATEAELLTCH      540
SAEYVGHLRATEKMKTRELHRESSNFDSIYICPSTFACAQLATGAACRLVEAVLSGEVLNGAAVVRPPGHHAEQDAACGFCFFNSVAVAA     630
RHAQTISGHALRILIVDWDVHHGNGTQHMFEDDPSVLYVSLHRYDHGTFFPMGDEGASSQIGRAAGTGFTVNVAWNGPRMGDADYLAAWH     720
RIVLPIAYEFNPELVLVSAGFDAARGDPLGGCQVSPEGYAHLTHLLMGLASGRIILILEGGYNLTSISESMAACTRSLLGDPPPLLTLPR     810
PPLSGALASITETIQVHRRYWRSLRVMKVEDREGPSSSKLVTKKAPQPAKPRLAERMTTREKKVLEAGMGKVTSASFGEESTPGQTNSET     900
AVVALTQDPSEAATGGAATLDQTTSEEAVGGATPDQTTSEETVGGAILDQTTSEDAVGGATLGQTTSEEAVGGATL                  990
AQTISEAAMEGATLDQTTSEEAPGGTELIQTPLASSTDHQTPPTSPVQGTTPQISPSTLIGSLRTLELGSESQGASESQAPGEENLLGEA   1080
AGGQDMADSMLMQGSRGLTDQAIFYAVTPLPWCPHLVAVCPIPAAGLDVTQPCGDCGTIQENWVCLSCYQVYCGRYINGEMLQHHGNSGH   1170
PLVLSYIDLSAWCYYCQAYVHHQALLDVKNIAHQNKFGEDMPHPH. 1216

FIG. 1C

```
HDAC1  140  HHAKKSEASGFCYVNDIVLAILELLKYH----QRVLYIDIDIHHGDGVEEAFYTTDRVMTVSFHKY--GEYFPGT  208
HDAC4  802  HHAEESTPMGFCYFNSVAVAAKLLQQRLSVS-K-ILIVDWDVHHGNGTQQAFYSDPSVLYMSLHRYDDGNFFPGS  874
HDAC5  832  HHAEESTAMGFCFFNSVAITAKLLQQKLNVG-K-VLIVDWDIHHGNGTQQAFYNDPSVLYISLHRYDNGNFFPGS  905
HDAC6  215  HHAQHSLMDGYCMFNHVAVAARYAQQKHRIR-R-VLIVDWDVHHGQGTQFTFDQDPSVLYFSIHRYEQGRFWPHL  287
HDAC6  610  HHAEQDAACGFCFFNSVAVAARHAQTISGHALR-ILIVDWDVHHGNGTQHMFEDDPSVLIYVSLHRYDHGTFFPMG  683
hda1   205  HHAEPQAAGGFCLFSNVAVAAKNILKNYPESVRRIMILDWDIHHGNGTQKSFYQDDQVLYVSLHRFEMGKYYPGT  279
```

FIG. 1D

| HOMOLOGY REGIONS | INITIAL AA IN HDAC1 | CONSENSUS SEQUENCES | | EXCEPTIONS |
|---|---|---|---|---|
| 1 | 99 | D(C/T)P(V/t)F<br>N/A | CLASS I<br>CLASS II | |
| 2 | 134 | NXXGGXHHA<br>RPPG  HHA | CLASS I<br>CLASS II | Hos3p ends in C.<br>AcuC ends in G |
| 3 | 148 | SG(F/Y)CXXN<br>G(F/Y)CXXN | CLASS I<br>CLASS II | Hda1 ends in S |
| 4 | 174 | DϕϕHHGDGV(Q/E)<br>DϕDϕHHGXGT  Q | CLASS I<br>CLASS II | |
| 5 | 193 | VX  T  XSH<br>VX(V/F) SXH | CLASS I<br>CLASS II | |
| 6 | 225 | NϕP(M/L)XDGIDDX(S/T)Y<br>N/A | CLASS I<br>CLASS II | Hos1p has instead:<br>NϕPLKHGCDDNY |
| 7 | 298 | ϕGGGG  Y<br>ϕEGG (Y/H) | CLASS I<br>CLASS II | |

FIG. 6A

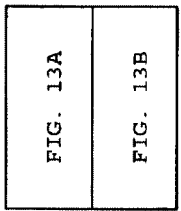

FIG. 13

| | FIG. 13A |
|---|---|
| | FIG. 13B |

Residues on rim of channel

| | P22 | Y91 |
|---|---|---|
| HDLP | P L | G G Y E N P |
| HDAC1 | P H | G - E D C P |
| HDAC2 | P H | G - E D C P |
| HDAC3 | P H | G - D D C P |
| HDAC8 | A K | G - Y D C P |
| HDAC4 | P E | G V D S D T |
| HDAC5 | P E | G V D S D T |
| HDAC6(a) | P E | - - - D S |
| HDAC6(b) | P E | - - - D S |
| HDAC7 | P E | G V D T D T |

Class I: HDAC1, HDAC2, HDAC3, HDAC8
Class II: HDAC4, HDAC5, HDAC6(a), HDAC6(b), HDAC7

Residues in channel

| | G140 P141 | P198 | P265 |
|---|---|---|---|
| HDLP | N G F | E - Y A F P | Y L |
| HDAC1 | S G F | E - Y F - P | R L |
| HDAC2 | S G F | E - Y F - P | R L |
| HDAC3 | S G F | N - Y F F P | R L |
| HDAC8 | S G F | P - G F F P | P M |
| HDAC4 | H G F | D G N F F P | P L |
| HDAC5 | H G F | N G N F F P | P L |
| HDAC6(a) | D G Y | Q G R F W P | P K |
| HDAC6(b) | C G F | H G T F F P | P L |
| HDAC7 | M G F | D G N F F P | P L |

Class I: HDAC1, HDAC2, HDAC3, HDAC8
Class II: HDAC4, HDAC5, HDAC6(a), HDAC6(b), HDAC7

FIG. 13A where Y = OH, NHOH, o-aminoaniline

US 8,895,284 B2

CLASS II HUMAN HISTONE DEACETYLASES, AND USES RELATED THERETO

CROSS REFERENCE TO RELATED APPLICATIONS

This application is a divisional of and claims priority under 35 U.S.C. §120 to U.S. patent application Ser. No. 13/324,036, filed Dec. 13, 2011, now U.S. Pat. No. 8,435,780, which is a divisional of and claims priority under 35 U.S.C. §120 to U.S. patent application Ser. No. 12/370,390, filed Feb. 12, 2009, now U.S. Pat. No. 8,076,116, which is a continuation of and claims priority under 35 U.S.C. §120 to U.S. patent application Ser. No. 11/831,303, filed Jul. 31, 2007, now abandoned, which is a continuation of and claims priority under 35 U.S.C. §120 to U.S. patent application Ser. No. 10/964,313, filed Oct. 13, 2004, now U.S. Pat. No. 7,250,504, which is a continuation of and claims priority under 35 U.S.C. §120 to U.S. patent application Ser. No. 09/800,187, filed Mar. 5, 2001, now abandoned, which claims priority under 35 U.S.C. §119(e) to U.S. Provisional patent application, U.S. Ser. No. 60/186,802, filed Mar. 3, 2000, each of which is incorporated herein by reference.

GOVERNMENT FUNDING

This invention was made with government support under grant number GM38617 awarded by the National Institute of General Medical Sciences. The government has certain rights in the invention.

BACKGROUND OF THE INVENTION

The regulation and mechanism of transcription has been of great interest to researchers. In eukaryotic cells, DNA is packaged in the form of nucleosomal arrays. Each nucleosome core consists of 145 base pairs of DNA wound around an octarner of H2A, H2B, H3 and H4 histone proteins. These nucleosome cores are then packaged into higher order structures with additional factors to form chromatin (Luger, K. et al. *Nature,* 1997, 389, 251-60).

The incorporation of DNA into chromatin creates a repressive environment that has been implicated in transcriptional silencing. Two cellular processes serve to alter chromatin structure (Workman et al., *Annu. Rev. Biochem,* 1998, 67, 545-579). Chromatin remodeling factors such as SWI/SNF, RSC, NURF, and NRD (reviewed in Varga-Weisz, P. D. and Becker, P. B. *Curr. Opin. Cell Biol.,* 1998, 10, 346-353; see also, Tong et al. *Nature,* 1998, 395, 917-921; Zhang et al. *Cell,* 1998, 95, 279-289; Xue et al., *Mol. Cell,* 1998, 2, 851-861) have been shown to increase the accessibility of the DNA, presumably by modifications of the nucleosomal structure. A second cellular mechanism involves alterations of the acetylation state of nucleosomal histones. Hypoacetylated chromatin is often associated with silent genes, while hyperacetylation is correlated with actively transcribed genes. However, this rule is not absolute. Acetylation of K12 on histone H4 is observed in silent heterochromatin regions in *Drosophila* and yeast (reviewed in Grunstein, M. *Nature,* 1997, 389, 349-352). Furthermore, there is increasing evidence for regulation of non-histone proteins by acetylation, and this may function in activation as well as repression of transcription (see, Imhof et al., *Curr. Biol.,* 1997, 7, 689-692; Gu, W. and Roeder, R. G. *Cell,* 1997, 90, 595-606; Munshi et al. *Mol. Cell,* 1998, 2, 457-467). The acetylation state of histones and perhaps non-histone proteins is regulated by a dynamic interaction of histone acetyltransferase (HAT) and histone deacetylase (HDAC) enzymes.

Previously, three human HDACs (Taunton, J. et al. *Science,* 1996, 272, 408-411; Yang et al. *J. Biol. Chem.,* 1997, 272, 28001-28007; Emiliani et al. *Proc. Natl. Acad. Sci. USA,* 1998, 95, 2795-2800; Dagond et al. *Biochem. Biophys. Res. Commun.,* 1998, 242, 648-652) and five yeast HDACs (see, Rundlett et al. *Proc. Natl. Acad. Sci USA,* 1996, 93, 14503-14508; Carmen et al. *J. Biol. Chem.,* 1996, 271, 15837-15844) had been identified and several of these were biochemically characterized. These HDACs, together with the prokaryotic enzymes acetylspermine deacetylase (ASD) and acetoin utilization protein (acuC) comprise a deacetylase superfamily. In yeast, members of this superfamily can be subdivided into two classes based on size and sequence considerations, as well as the observation that Rpd3p and Hda1p function in biochemically distinct complexes. The first class (I) consists of Rpd3p, Hos1p, and Hos2p, while the second class contains Hda1p. Similarly in mammals, HDAC1, HDAC2 and HDAC3 conform to class I criteria, while no human class II HDAC proteins have been identified previously.

Clearly, the identification of alternate classes of genes encoding histone deacetylase proteins would aid in the investigation of functions for these protein products, and thus would be of great benefit in the control of gene transcription and the cell cycle.

SUMMARY OF THE INVENTION

In recognition of the desire to understand the cellular function and regulation of histone deacetylases, the present invention, in one aspect, provides heretofore unidentified histone deacetylase genes, and gene products, expressed in mammals. In general, the invention provides a novel class of isolated HDx polypeptides, preferably recombinant and/or substantially pure preparations of one or more of the subject HDx polypeptides. The invention also provides recombinantly produced HDx polypeptides. In other embodiments, the HDx polypeptides of the present invention bind to 14-3-3 proteins, such binding resulting in regulation of cellular localization of the HDx protein. Additionally, in certain other embodiments, the HDx polypeptides of the present invention associated with other HDx polypeptides of this novel class and regulate HDAC function by protein pairing In preferred embodiments, the invention features human class II HDAC nucleic acids and polypeptides. For example, the nucleic acid of SEQ ID NO. 1 encodes HDAC4 and is substantially identical to GenBank Accession No. XM_002252; and the polypeptide of SEQ ID NO. 2 corresponds to HDAC4 and is substantially identical to GenBank Accession No. XP_002252. The nucleic acid of SEQ ID NO. 3 encodes HDAC5 and is substantially identical to GenBank Accession No. XM_008359; and the polypeptide of SEQ ID NO. 4 corresponds to HDAC5 and is substantially identical to GenBank Accession No. XP_008359.2. The nucleic acid of SEQ ID NO. 5 encodes HDAC6 and is substantially identical to GenBank Accession No. NM_006044; and the polypeptide of SEQ ID NO. 6 encodes HDAC6 and is substantially identical to NP_006035.2.

In still other embodiments, the invention features HDAC7-type human class II HDAC nucleic acids and polypeptides, including both HDAC7A and HDAC7B. HDAC7A is encoded by the nucleic acid of SEQ ID NO. 11 and which is substantially identical to GenBank Accession No. XM_007047. The amino acid sequence of HDAC7A is represented in SEQ ID NO. 12 and is substantially identical to GenBank Accession No. XP_007047.1. HDAC7B is encoded by the nucleic acid of SEQ ID NO. 13 and which is substantially identical to GenBank Accession No. XM_004963. The amino acid sequence of HDAC7A is represented in SEQ ID NO. 14 and is substantially identical to GenBank Accession No. XP_004963.2.

The HDx polypeptides disclosed herein are capable of modulating proliferation, survival and/or differentiation of cells, inter alia because of their ability to alter chromatin structure by deacetylating histones. In preferred embodiments the polypeptide has a biological activity including an ability to deacetylate an acetylated histone substrate, preferably a substrate analog of histone H3 and/or H4. In other embodiments the HDx polypeptides of the present invention bind to trapoxin or to trichostatin, such binding resulting in the inhibition a deacetylase activity of the HDx polypeptide. However, HDx polypeptides which specifically antagonize such activities, such as may be provided by dominant negative mutants, are also specifically contemplated.

In addition to acting as a deacetylating enzymes, the HDx polypeptides of the present invention are also involved in a novel mechanism for controlling the activity of HDAC proteins. In certain embodiments, polypeptides of the present invention are able to interact with 14-3-3 proteins, whereby cellular localization is regulated. Moreover, in preferred embodiments, the subject HDx proteins have the ability to modulate cell growth by influencing cell cycle progression or to modulate gene transcription.

In one embodiment, the polypeptide is identical with or homologous to an HDx protein. Exemplary HDx polypeptides include amino acid sequences represented in any one of SEQ ID Nos. 2, 4 or 6. Related members of the HDx family are also contemplated, for instance, an HDx polypeptide preferably has an amino acid sequence at least 80% homologous to a polypeptide represented by one of more of the polypeptides designated in SEQ ID: Nos: 2, 4, or 6, though polypeptides with higher sequence homologies of, for example, 85%, 90%, 95% or 98% are also contemplated. In one embodiment, the HDx polypeptide is encoded by a nucleic acid which hybridizes under stringent conditions with a nucleic acid sequence represented in one or more of SEQ ID Nos: 1, 3 or 5. Homologs of the subject HDx proteins also include versions of the protein which are resistant to post-translation modification, as for example, due to mutations which alter modification sites (such as tyrosine, threonine, serine or asparagine residues), or which inactivate an enzymatic activity associated with the protein.

The HDx polypeptide can comprise a full length protein, such as represented in SEQ ID Nos. 2, 4 or 6, or it can comprise a fragment corresponding to particular motifs/domains (for example, a v motif such as shown in SEQ ID Nos, 7, 8, 9 or 10), or to arbitrary sizes, e.g., at least 5, 10, 25, 50, 100, 150 or 200 amino acids in length. In preferred embodiments, the polypeptide, or fragment thereof, specifically deacetylates histones. In other preferred embodiments, the HDx polypeptide includes at least one v motif and in certain embodiments includes two v motifs.

In certain preferred embodiments, the invention features a purified or recombinant HDx polypeptide having a molecular weight in the range of 80 kDa to 150 kDa. It will be understood that certain post-translational modifications, e.g., phosphorylation, prenylation and the like, can increase the apparent molecular weight of the HDx protein relative to the unmodified polypeptide chain.

The subject proteins can also be provided as chimeric molecules, such as in the form of fusion proteins. For instance, the HDx protein can be provided as a recombinant fusion protein which includes a second polypeptide portion, e.g., a second polypeptide having an amino acid sequence unrelated (heterologous) to the HDx polypeptide, e.g., the second polypeptide portion is glutathione-S-transferase, e.g., the second polypeptide portion is an epitope tage.

In yet another embodiment, the invention features a nucleic acid encoding an HDx polypeptide, or polypeptide homologous thereto, which polypeptide has the ability to modulate, e.g., either mimic or antagonize, at least a portion of the activity of a wild-type HDx polypeptide. Exemplary HDx-encoding nucleic acid sequences are represented by SEQ ID Nos: 1, 3 or 5.

In another embodiment, the nucleic acid of the present invention includes a coding sequence which hybridizes under stringent conditions with one or more of the nucleic acid sequences in SEQ ID. Nos. 1, 3 or 5. The coding sequence of the nucleic acid can comprise a sequence which is identical to a coding sequence represented in one of SEQ ID Nos. 1, 3 or 5, or it can merely be homologous to one or more of these sequences. In preferred embodiments, the nucleic acid encodes a polypeptide which specifically modulates, by acting as either an agonist or antagonist, the enzymatic activity of an HDx polypeptide.

Furthermore, in certain preferred embodiments, the subject HDx nucleic acid will include a transcriptional regulatory sequence, e.g., at least one of a transcriptional promoter or transcriptional enhancer sequence, which regulatory sequence is operably linked to the HDx gene sequence. Such regulatory sequences can be used to render the HDx gene sequence suitable for use as an expression vector. This invention also contemplates the cells transfected with said expression vector whether prokaryotic or eukaryotic and a method for producing HDx proteins by employing said expression vectors.

In yet another embodiment, the nucleic acid hybridizes under stringent conditions to a nucleic acid probe corresponding to at least 12 consecutive nucleotides of either sense or antisense sequence of one or more of SEQ ID Nos.: 1, 3 or 5; and more preferably to at least 20. 30, 40 or 50 consecutive (e.g., contiguous) nucleotides; and more preferably to at least 100, 200 or 300 consecutive nucleotides of either sense or antisense sequence of one or more of SEQ ID Nos. 1, 3, or 5.

Yet another aspect of the present invention concerns an immunogen comprising an HDx polypeptide in an immunogenic preparation, the immunogen being capable of eliciting an immune response specific for an HDx polypeptide; e.g. a humoral response, e.g. an antibody response; e.g. a cellular response. In preferred embodiments, the immunogen comprising an antigenic determinant, e.g. a unique determinant, from a protein represented by one of SEQ ID Nos. 2, 4, 6, 7, 8, 9 or 10.

A still further aspect of the present invention features antibodies and antibody preparations specifically reactive with an epitope of the HDx immunogen.

The invention also features transgenic non-human animals, e.g., mice, rats, rabbits, chickens, frogs or pigs, having a transgene, e.g., animals which include (and preferably express) a heterologous form of an HDx gene described herein, or which misexpresses an endogenous HDx gene, e.g., an animal in which expression of one or more of the subject HDx proteins is disrupted. Such a transgenic animal can serve as an animal model for studying cellular and tissue disorders comprising mutated or mis-expressed HDx alleles or for use in drug screening.

The invention also provides a probe/primer comprising a substantially purified oligonucleotide, wherein the oligonucleotide comprises a region of nucleotide sequence which hybridizes under stringent conditions to at least 12 consecutive nucleotides of sense or antisense sequence of SEQ ID Nos: 1, 3 or 5, and more preferably to at least 30, 40, 50, 100, 200 or 300 contiguous nucleotides of said sequences.

Nucleic acid probes which are specific for each of the HDx proteins are contemplated by the present invention, e.g., probes which can discern between nucleic acid encoding a human or bovine HD. In preferred embodiments, the probe/primer further includes a label group attached thereto and able to be detected. The label group can be selected, e.g., from a group consisting of radioisotopes, fluorescent compounds, enzymes, and enzyme co-factors. Probes of the invention can be used as a part of a diagnostic test kit for identifying dysfunctions associated with mis-expression of an HDx protein, such as for detecting in a sample of cells isolated from a patient, a level of a nucleic acid encoding a subject HDx protein; e.g., measuring an HDx mRNA level in a cell, or determining whether a genomic HDx gene has been mutated or deleted. These so called "probes/primers" of the invention can also be used as a part of "antisense" therapy which refers to administration or in situ generation of oligonucleotide probes or their derivatives which specifically hybridize (e.g., bind) under cellular conditions, with the cellular mRNA and/or genomic DNA encoding one or more of the subject HDx proteins so as to inhibit expression of that protein, e.g., by inhibiting transcription and/or translation. Preferably, the oligonucleotide is at least 12 nucleotides in length, though primers of 25, 40, 50, or 75 nucleotides in length are also contemplated.

In yet another aspect, the invention provides an assay for screening test compounds for inhibitors, or alternatively, potentiators, or an interaction between an HDx protein and an HDx binding protein or nucleic acid sequence. An exemplary method includes the steps of (I) combining an HDx polypeptide or fragment thereof, an HDx target polypeptide (such as a histone, a 14-3-3 protein, a MEF2 transcription factor, a retinoblastoma associated protein such as RbAp48, or fragment thereof which interacts with the HDx protein), and a test compound, e.g., under conditions wherein, but for the test compound, the HDx protein and the target polypeptide are able to interact; and (ii) detecting the formation of a complex which includes the HDx protein and the target polypeptide either by directly quantitating the complex, the deacetylase activity of the HDx protein, or by measuring inductive effects of the HDx protein. A statistically significant change, such as a decrease, in the formation of a complex in the presence of a test compound (relative to what is seen in the absence of a test compound) is indicative of a modulation, e.g., inhibition, of the interaction between the HDx protein and its target polypeptide.

In a particularly preferred embodiment, the invention provides combinatorial chemical libraries of compounds for screening for specific inhibitors of class II Histone Deacetylases (HDACs). The combinatorial libraries are used in the assays of the invention in order to identify HDAC inhibitors, including inhibitors specific to all class II histone deacetylases and inhibitors specific to individual class II histone deacetylases. The combinatorial libraries of the invention comprise a plurality of compounds represented by the structures #1, #2, and #3 shown in FIG. 14A and the structure shown in FIG. 14B. In preferred embodiments, the plurality of compounds are spatially segregated.

Furthermore, the present invention contemplates the use of other homologs of the HDx polypeptides or bioactive fragments thereof to generate similar assay formats. In one embodiment, the drug screening assay can be derived with a fungal homolog of an HDx protein, such as RPD3, in order to identify agents which selectively inhibit the fungal histone acetylase and not the human enzyme, e.g., for use as antifungal agents.

Yet another aspect of the present invention concerns a method for modulating one or more of growth, differentiation, or survival of a mammalian cell by modulating HDx bioactivity, e.g., by inhibiting the deacetylase activity of HDx proteins, or disrupting certain protein-protein interactions. In general, whether carried out in vivo, in vitro, or in situ, the method comprises treating the cell with an effective amount of an HDx therapeutic so as to alter, relative to the cell in the absence of treatment, at least one of (i) rate of growth; (ii) differentiation, or (iii) survival of the cell. Accordingly, the method can be carried out with HDx therapeutics such as peptide and peptidomimetics or other molecules identified in the above-reference drug screens which antagonize the effects of naturally occurring HDx protein on said cell. Other HDx therapeutics include antisense constructs for inhibiting expression of HDx proteins, and dominant negative mutants of HDx proteins which competitively inhibit protein-substrate and/or protein-protein interactions upstream and downstream of the wild-type HDx protein.

In an exemplary embodiment the subject method is used to treat tumor cells by antagonizing HDx activity and blocking cell cycle progression. In one embodiment, the subject method includes the treatment of testicular cells, so as to modulate spermatogenesis. In another embodiment, the subject method is used to modulate osteogenesis, comprising the treatment of osteogenic cells with an HDx polypeptide. Likewise, where the treated cell is a chondrogenic cell, the present method is used to modulate chondrogenesis. In still another embodiment, HDx polypeptides can be used to modulate the differentiation of progenitor cells, e.g., the method can be used to cause differentiation of a hematopoietic cells, neuronal cells, or other stem/progenitor cell populations, to maintain a cell in a differentiated state, and/or to enhance the survival of a differentiated cell, e.g., to prevent apoptosis, or other forms of cell death.

In addition to such HDx therapeutic uses, anti-fungal agents developed with such screening assays as described herein can be used, for example, as preservatives in foodstuff, feed supplement for promoting weight gain in livestock, or in disinfectant formulations for treatment of non-living matter, e.g., for decontaminating hospital equipment and rooms. In similar fashion, assays provided herein will permit selection of deacetylase inhibitors which discriminate between the human and insect deacetylase enzymes. Accordingly, the present invention expressly contemplates the use and formulations of the deacetylase inhibitors in insecticides, such as for use in management of insects like the fruit fly. Moreover, certain of the inhibitors can be selected on the basis of inhibitory specificity for plant HDx-related activities relative to the mammalian enzymes. Thus, the present invention specifically contemplates formulations of deacetylase inhibitors for agricultural applications, such as in the form of a defoliant or the like.

The present method is applicable, for example, to cell culture technique, such as in the culturing of hematopoietic cells and other cells whose survival or differentiative state is dependent on HDx function. Moreover, HDx agonists and antagonists can be used for therapeutic intervention, such as to enhance survival and maintenance of cells, as well as to influence organogenic pathways, such as tissue patterning and other differentiation processes. In an exemplary embodiment, the method is practiced for modulating, in an animal, cell growth, cell differentiation or cell survival, and comprises administering a therapeutically effective amount of an HDx polypeptide to alter, relative to the absence of HDx treatment, at least one of (I) rate of growth; (ii) differentiation; or (iii) survival of one or more cell-types in the animal.

Another aspect of the present invention provides a method of determining if a subject, e.g., a human patient, is at risk for a disorder characterized by unwanted cell proliferation or aberrant control of differentiation. The method includes detecting, in a tissue of the subject, the presence or absence of a genetic lesion characterized by at least one of (I) a mutation of a gene encoding an HDx protein, e.g., represented in one of SEQ ID Nos. 2, 4, 6, 7, 8, 9, or 10 or a homolog thereof; or (ii) the mis-expression of an HDx gene. In preferred embodiments, detecting the genetic lesion includes ascertaining the existence of at least one of; a deletion of one or more nucleotides from an HDx gene; an addition of one or more nucleotides to the gene, a substitution of one or more nucleotides of the gene, a gross chromosomal rearrangement of the gene; an alteration in the level of a messenger RNA transcript of the gene; the presence of a non-wild type splicing pattern of a messenger RNA transcript of the gene; or a non-wild type level of the protein.

For example, detecting the genetic lesion can include (I) providing a probe/primer including an oligonucleotide containing a region of nucleotide sequence which hybridizes to a sense or antisense sequence of an HDx gene, e.g., a nucleic acid represented in one of SEQ ID Nos. 1, 3 or 5 or naturally occurring mutants thereof, or 5 or 3' flanking sequences naturally associated with the HDx gene; (ii) exposing the probe/primer to nucleic acid of the tissue; and (iii) detecting, by hybridization of the probe/primer to the nucleic acid, the presence or absence of the genetic lesion; e.g. wherein detecting the lesion comprises utilizing the probe/primer to determine the nucleotide sequence of the HDx gene and, optionally, of the flanking nucleic acid sequences. For instance, the probe/primer can be employed in a polymerase chain reaction (PCR) or in a ligation chain reaction (LGR). In alternate embodiments, the level of an HDx protein is detected in an immunoassay using an antibody which is specifically immunoreactive with the HDx protein.

DESCRIPTION OF THE DRAWING

FIGS. 1A-1D Predicted amino acid sequences of human class II histone deacetylases. The conserved residues of the catalytic domains are highlighted. (A) HDAC4 (SEQ ID NO:2) (B) HDAC5 (SEQ ID NO:4) (C) HDAC6 (SEQ ID NO:6) predicted amino acid sequences. Note that there are two putative catalytic domains in HDAC6. (D) Alignment of catalytic domains of yeast HDA1p (SEQ ID NO:16), human HDAC1 (SEQ ID NO:15), 4 (SEQ ID NO:8), and 5 (SEQ ID NO:9) with both catalytic regions of HDAC6 (SEQ ID NO:10 and residues 610-683 of SEQ ID NO:6, respectively). The residues that are conserved in these HDACs as well as in acuC (*B. subtilis*, Accession 348052) and ASD (*M. ramosa*, Accession 3023317) are in bold type, and those residues that are conserved within the Class II human HDAC enzymes are boxed.

FIGS. 6A and 6B. Sequence analysis suggests that HDAC enzymes have diverged into two classes. (A) (SEQ ID NOS: 17-25, respectively) Alignment of human HDAC enzymes 1 through 6 with yeast Rpd3p, Hos1p, Hos2p, Hos3p, *M. ramosa* ASD, and *B. subtilis* acuC reveals the presence of seven conserved regions, whose consensus sequences differ between the two classes. Amino acids are represented by single letter codes; X represents any amino acid while Φ indicates a hydrophobic residue. NF=not found. (B) A phylogenetic analysis suggests that the HDAC enzymes diverged from a common prokaryotic ancestor to form two classes of HDAC proteins. Proteins from three different phyla were examined. Prokaryotic proteins are preceded by (pro), yeast proteins are preceded by y, while human proteins are capitalized. Note that yHos3p does not correlate well with either HDAC class.

A) Recombinant, FLAG-tagged HDAC1 and HDAC4 were transiently expressed in TAg Jurkat cells and immunoprecipitated using α-FLAG agarose (Sigma). Mock-transfected cells were used as a negative control. The immunopurified complexes were separated by SDS/PAGE and the proteins were visualized by silver stain. Two novel bands at 30 and 32 kDa in the HDAC4 immunoprecipitate were identified as 14-3-3 β and ε by peptide microsequencing analysis, B) The association between HDAC4 and HDAC5 with 14-3-3 was confirmed by Western blot analysis. The recombinant FLAG-tagged proteins were immunoprecipitated with α-FLAG agarose and the purified complexes were separated by SDS/PAGE. The presence of HDAC3, 14-3-3 β and ε was confirmed by probing with specific antibodies (Santa Cruz).

Figure 8A:
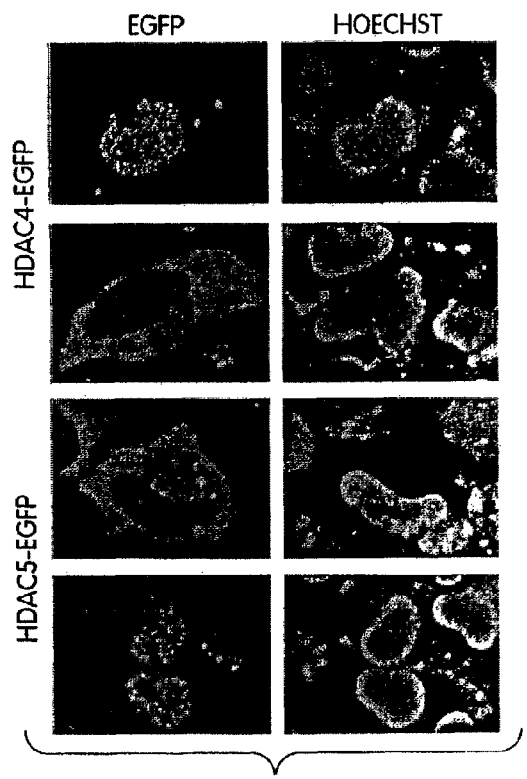
Figure 8B:
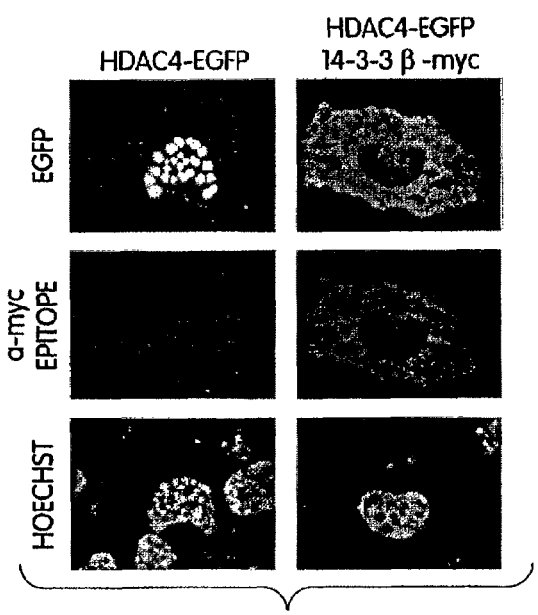

FIGS. 8A and 8B. Nuclear-cytoplasmic shuttling of HDAC4 and HDAC5 is correlated to 14-3-3 expression levels A) Recombinant HDAC4-EGFP and HDAC5-EGFP were transiently expressed in U2OS cells and the localization of the protein was observed by fluorescence microscopy.

B) Overexpression of 14-3-3 β causes an increased cytoplasmic localization of HDAC4-EGPF. U2OS cells were transiently transfected with HDAC4-EGFP and either a control plasmid (pcDNA3.1, Invitrogen) or myc-tagged 14-3-3 β. Forty-eight hours post-transfection, the cells were fixed with paraformaldehyde and probed with an α-myc antibody (Upstate Biotechnology) and an α-mouse Ig Texas Red conjugated secondary antibody (Sigma). The DNA was stained with Hoechst dye (Molecular Probes).

Figure 9A:
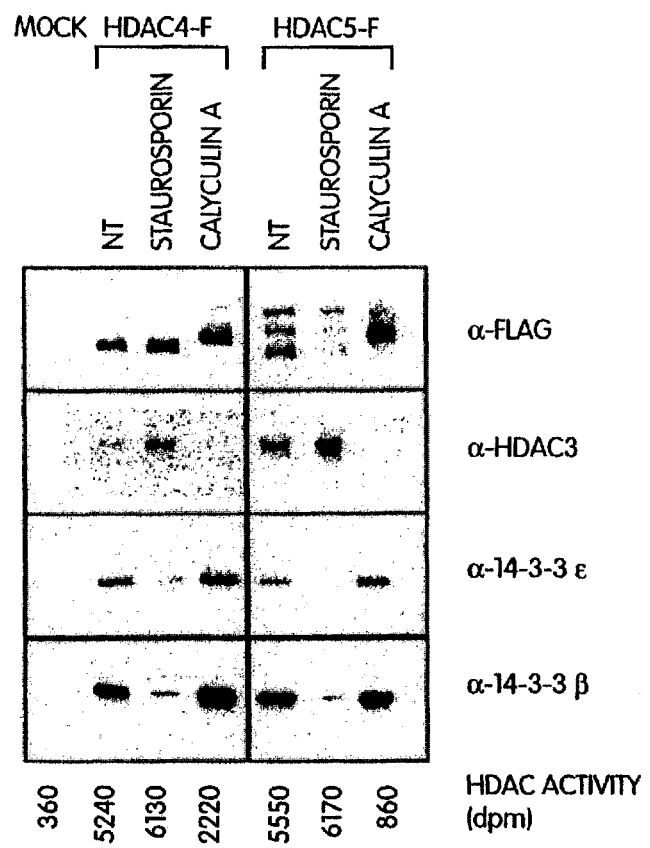
Figure 9B:
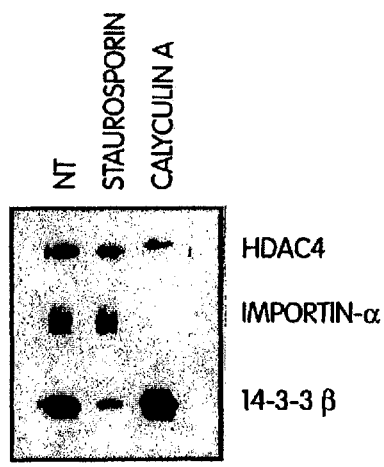

FIGS. 9A and 9B. Phosphorylation-dependent binding of 14-3-3 to HDAC4 and HDAC5

A) Association of HDAC4 and HDAC5 with 14-3-3 and HDAC3 is dependent on the phosphorylation state of the proteins. HDAC4-FLAG and HDAC5-FLAG were transiently expressed in TAg Jurkat cells. Forty-eight hours post-transfection, the cells were treated for 1.5 hours with staurosporine and calyculin A. The immunopurified HDAC4-FLAG and HDAC5-FLAG complexes were subjected to Western blot analysis and tested for HDAC activity, as described in the experimental procedures. The HDAC activity was measured by scintillation counting of the released [$^3$H]-acetic acid.

B) The binding of 14-3-3 to HDAC4 prevents interaction with importin α. Forty-eight hours after transfection with HDAC4-FLAG, TAg Jurkat cells were treated with staurosporin or calyculin A for 1.5 hours. HDAC4-FLAG was immunopurified and subjected to Western blot analysis with α-importin α antibodies (Transducin Laboratories).

Figure 10:
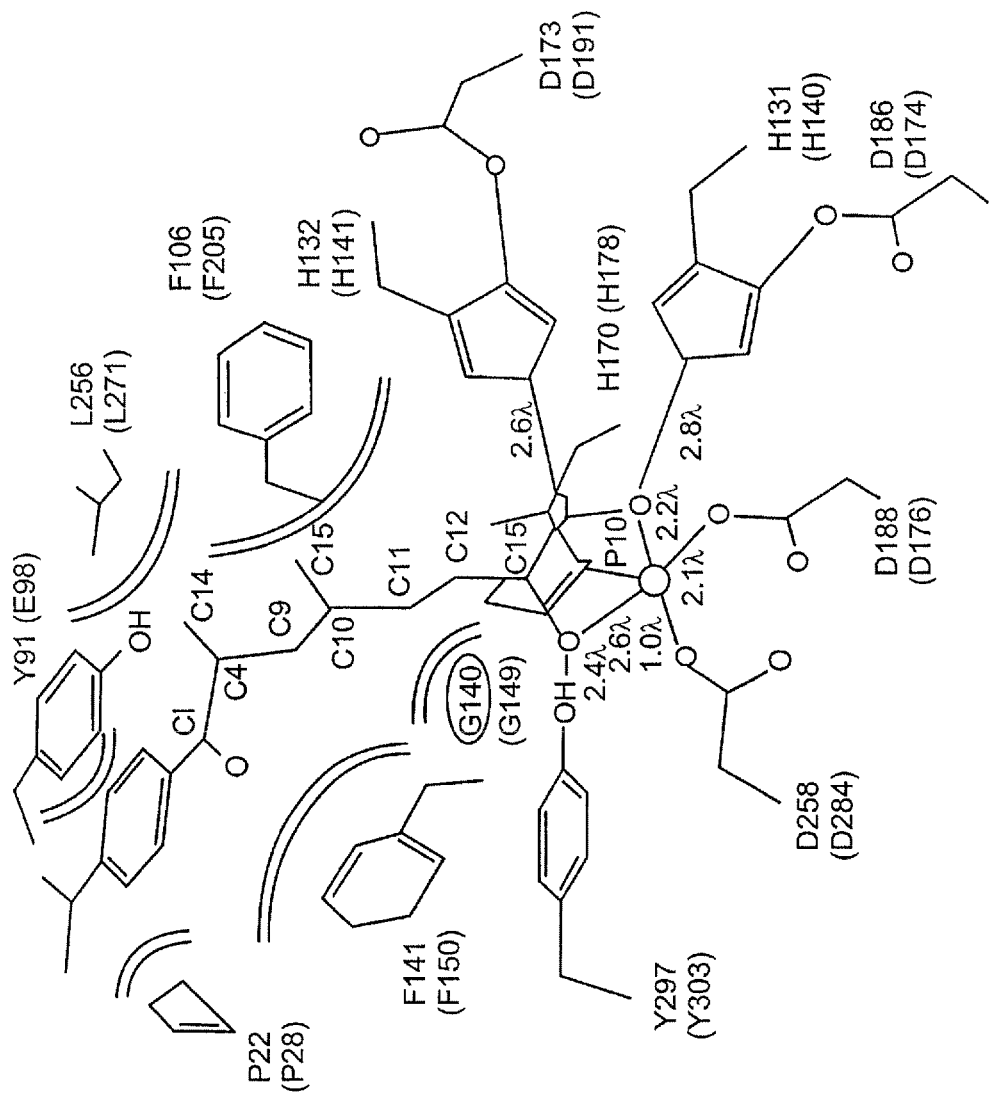

FIG. 10. Schematic representation of HDLP-TSA complex interactions. The TSA HDAC inhibitor is shown bound to HPLP (C7-C15 of TSA are labeled). The surrounding HDLP residues are labelled and the corresponding HDAC1 active site residues are indicated below in parentheses. The $Zn^{2+}$ cation in the active site of HDLP is shown as a filled circle. Thatched semi-circles indicate van der Waals contacts between hydrophobic protein resides and TSA, while hydrogen bonds are shown as dashed lines.

Figure 11A:
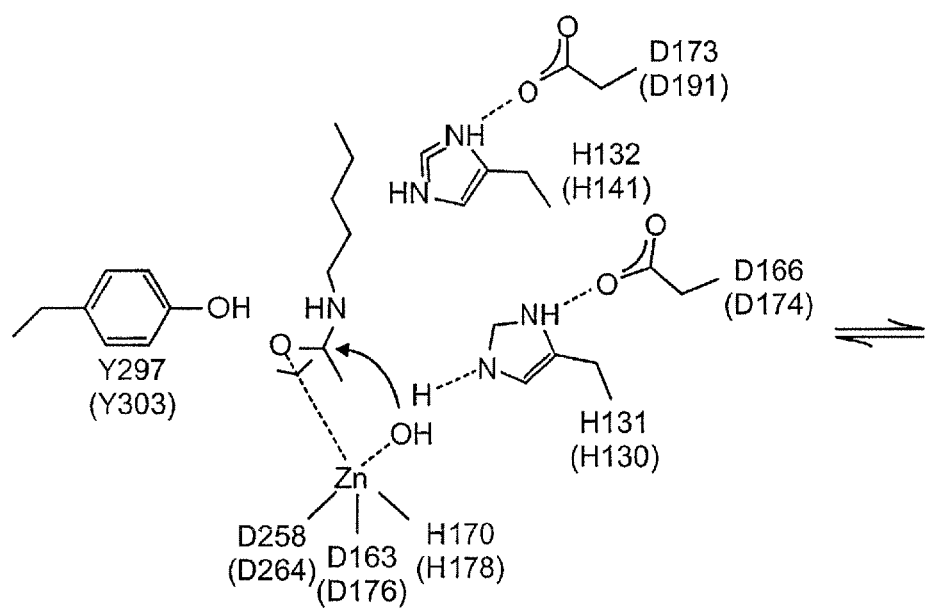
Figure 11B:
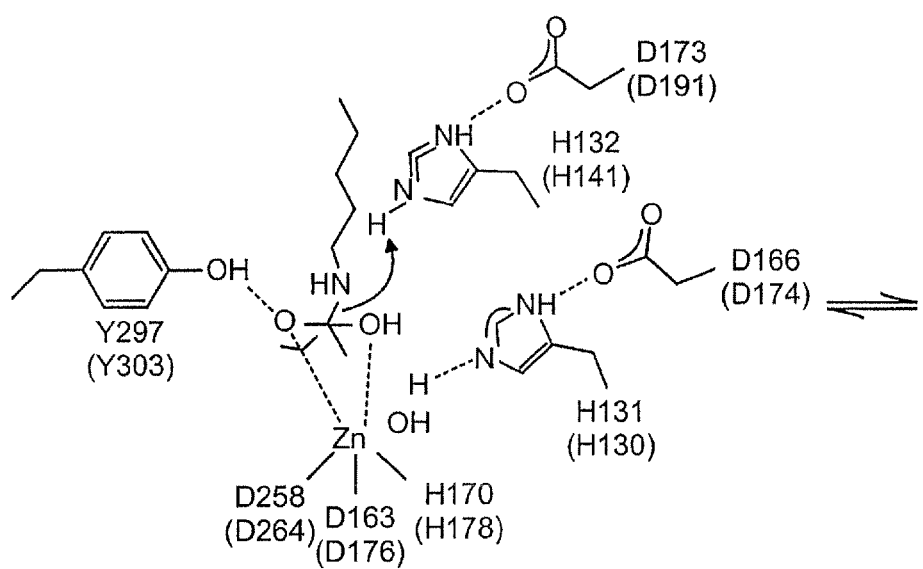
Figure 11C:
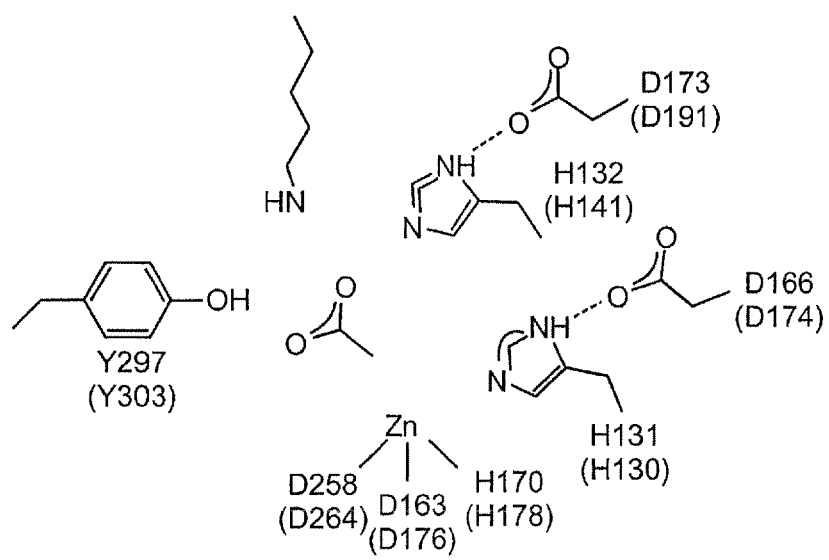

FIGS. 11A-11C. Proposed catalytic mechanism for deacetylation of acetylated lysine. HDLP active site residues and their proposed HDAC counterparts (in parentheses) are labelled.

Figure 12:
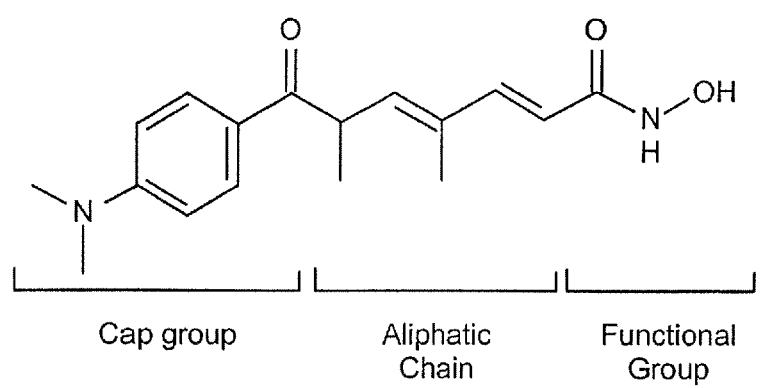

FIG. 12. General structural feature of HDAC inhibitors. The general structural features of HDAC inhibitors include a Cap group which can be varied to optimize inhibition of a particular HDAC or class of HDACs, an aliphatic chain and a functional group which interacts with the active site of the HDAC.

Figure 13B:
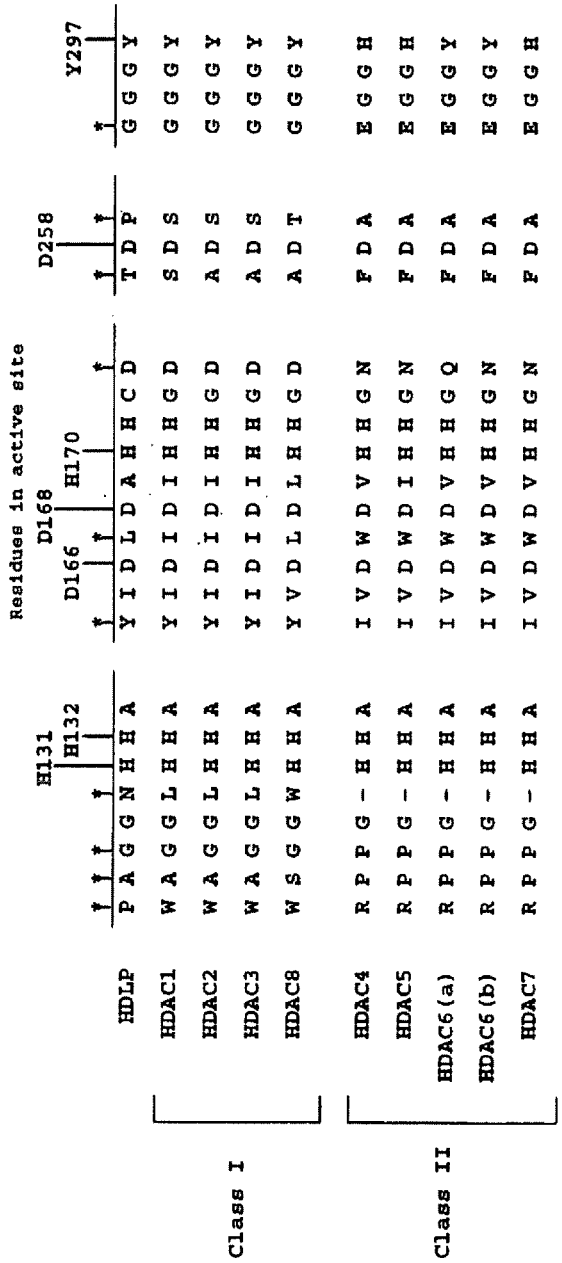

FIGS. 13A and 13B. Alterations in residues contacting TSA in human HDACs. The residues contacting TSA in HDLP are those which are both shaded and labelled with a consensus residue (i.e. P22 and Y91 residues in the rim of channel, GI40, F141, F198, and L265 residues in the channel, and 11131, 132, D166, D168, 11170, D258, and Y297 residues in the active site) is shown. The surrounding resides that differ between class I and class II HDACs are shaded and labelled with an asterisk (*). (SEQ ID NOS:26-73, respectively.)

Figure 14A:
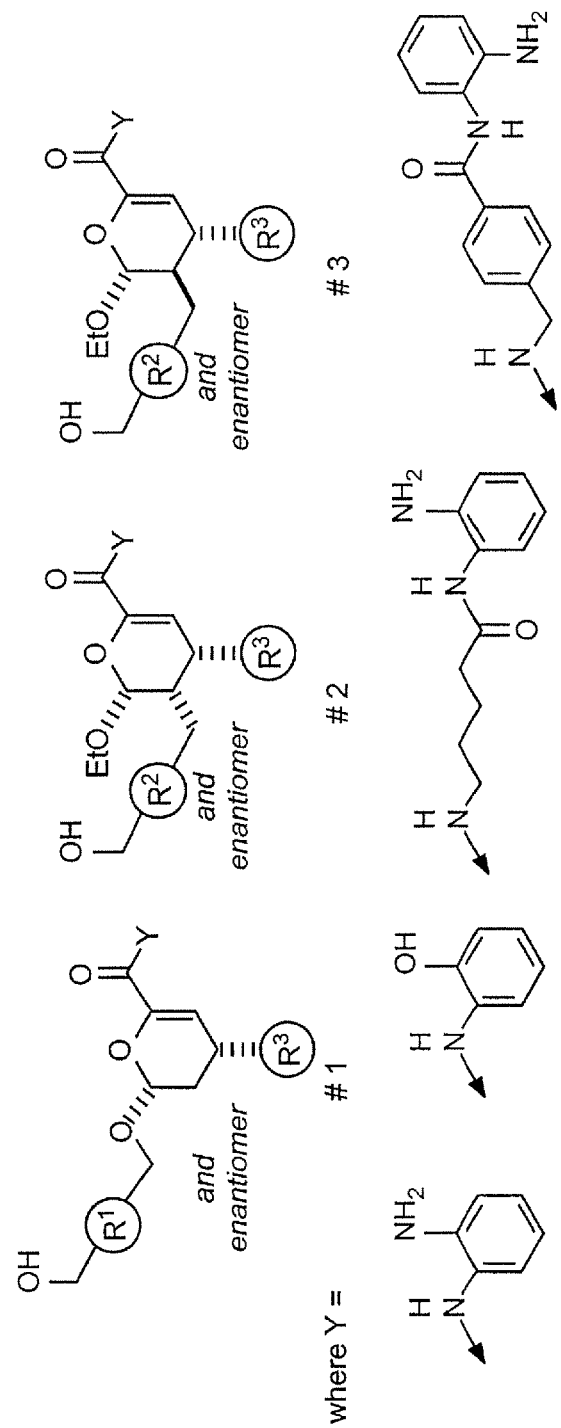
Figure 14B:
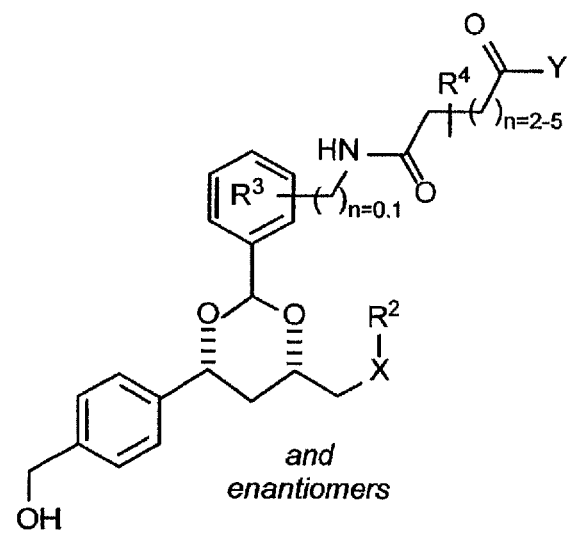

FIGS. 14A and 14B. HDAC inhibitor small molecule libraries. The generalized structures of two representative HDAC inhibitor compound libraries are shown.

Figure 15:
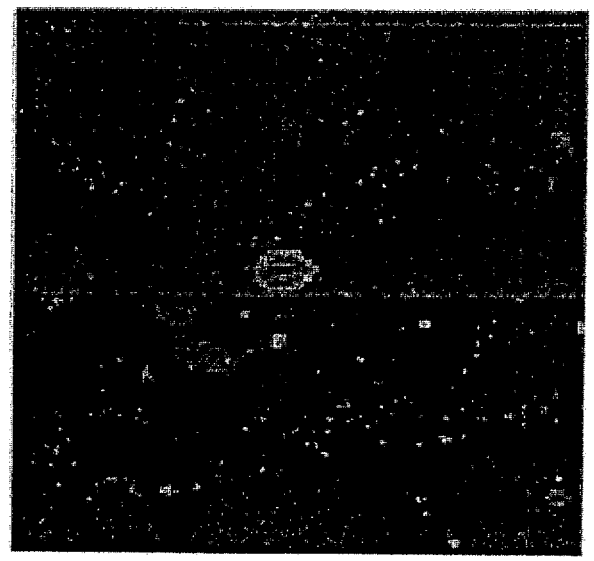

FIG. 15. Representative positive from HDAC6 screen of printed library. Cy5HDAC was used to screen the printed 1,3-dioxane library. A representative positive (compound 4-P9) from this screen is shown.

Figure 16:
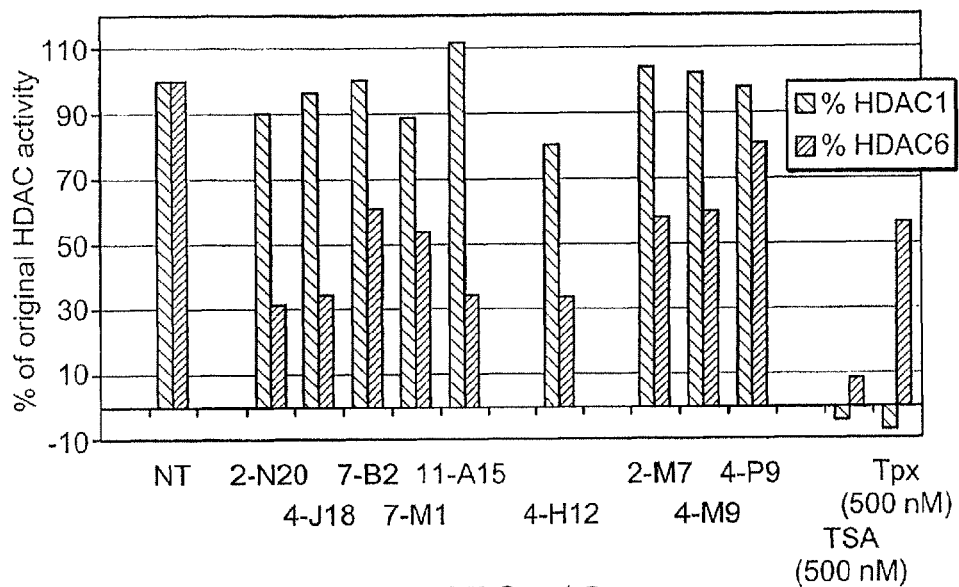

FIG. 16. Affect of representative compounds on HDAC1 and HDAC6 activity.

Figure 17:
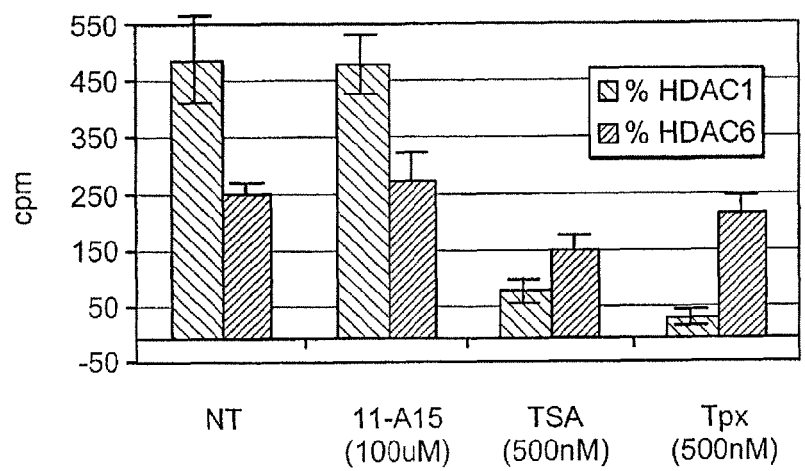

FIG. 17. Retesting of resynthesized 11-A15.

DEFINITIONS

For convenience, certain terms employed in the specification, examples and appended claims are collected here.

As used herein, the "HDx" polypeptides and nucleic acids of the invention include the histone deacetylace ("HDAC") class II polypeptide and nucleic acid sequences disclosed herein and "HDx" and "HDAC" are used interchangeably.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "gene" or "recombinant gene" refers to a nucleic acid comprising an open reading frame encoding one of the novel class of HDx polypeptides of the present invention, including both exon and (optionally) intron sequences. A "recombinant gene" refers to nucleic acid encoding an HDx polypeptide and comprising HDx-encoding exon sequences, though it may optionally include intron sequences which are either derived from a chromosomal HDx gene or from an unrelated chromosomal gene. Exemplary recombinant genes encoding the subject HDx polypeptide are represented in the appended Sequence Listing. The term "intron" refers to a DNA sequence present in a given HDx gene which is not translated into protein and is generally found between exons.

As used herein, the term "transfection" means the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of an HDx polypeptide or, where antisense expression occurs from the transferred gene, the expression of a naturally-occurring form of the HDx protein is disrupted.

As used herein, the term "specifically hybridizes" refers to the ability of the probe/primer of the invention to hybridize to at least 15 consecutive nucleotides of an HDx gene, such as an HDx sequence designated in one of SEQ ID Nos: 1, 3 or 5, or a sequence complementary thereto, or naturally occurring mutants thereof, such that it has less than 15%, preferably less than 10%, and more preferably less than 5% background hybridization to a cellular nucleic acid (e.g., mRNA or genomic DNA) encoding a protein other than an HDx protein, as defined herein. In preferred embodiments, the oligonucleotide probe specifically detects only one of the subject HDx paralogs, e.g., does not substantially hybridize to transcripts for other HDx homologs in the same species. In general, the term "specifically hybridizes" or "specifically detects" further refers to the ability of a nucleic acid molecule of the invention to hybridize to at least approximately 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 100, 150, 200, 300, 350, or 400 consecutive nucleotides of a vertebrate, preferably a HDAC gene. In certain instances the invention provides nucleic acids which hybridize under stringent conditions to a nucleic acid represented by SEQ ID Nos. 1, 3 or 5 or complement thereof or the nucleic acids. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1-6.3.6 or in Molecular Cloning: A Laboratory Manual, Cold Spring Harbor Press (1989). For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature and salt concentration may be held constant while the other variable is changed. In a preferred embodiment, an htrb nucleic acid of the present invention will bind to one of SEQ ID Nos. 1, 3, or 5 or complement thereof under moderately stringent conditions, for example at about 2.0× SSC and about 40° C. In a particularly preferred embodiment, an HDAC nucleic acid of the present invention will bind to one of SEQ ID Nos. 1, 2, 3, or 4 or complement thereof under high stringency conditions. In another particularly preferred embodiment, a HDAC nucleic acid sequence of the present invention will bind to one of SEQ ID Nos. 1, 3 or 5 which correspond to the HDAC cDNA, preferably ORF nucleic acid sequences, under high stringency conditions.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

"Transcriptional regulatory sequence" is a generic term used throughout the specification to refer to DNA sequences, such as initiation signals, enhancers, and promoters, which induce or control transcription of protein coding sequences with which they are operable linked. In preferred embodiments, transcription of one of the recombinant HDx genes is under the control of a promoter sequence (or other transcriptional regulatory sequence) which controls the expression of the recombinant gene in a cell-type which expression is intended. It will also be understood that the recombinant gene can be under the control of transcriptional regulatory sequences which are the same or which are different from those sequences which control transcription of the naturally-occurring forms of HDx genes.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of hepatic, pancreatic, neuronal or hematopoietic origin. The term also covers so-called "leaky" promoters, which regulate expression of a selected DNA primarily in one tissue, but can cause at least low level expression in other tissues as well.

As used herein "transgenic animal" is any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of recombinant DNA molecule. This molecule may be integrated within a chromosome, or it may be extrachromosomally replicating DNA. In the typical transgenic animals described herein, the transgene causes cells to express a recombinant form of one of the HDx proteins, e.g., either agonistic or antagonistic forms. However, transgenic animals in which the recombinant HDx gene is silent are also contemplated, as for example, the FLP or CRE recombinase dependent constructs described below. Moreover, "transgenic animal" also includes those recombinant animals in which gene disruption of one or more HDx genes is caused by human intervention, including both recombination and antisense techniques.

The "non-human animals of the invention include, but are not limited to, vertebrates such as rodents, non-human primates, sheep, dog, cow, chickens, amphibians, reptiles, etc. Preferred non-human animals are selected from the rodent family including rat and mouse, most preferably mouse, though transgenic amphibians, such as members of the *Xenopus* genus, and transgenic chickens can also provide important tools for understanding and identifying agents which can affect, for example, embryogenesis and tissue formation. The invention also contemplates transgenic insects, including those of the genus *Drosophila*, such as *D. melanogaster*. The term "chimeric animal" is used herein to refer to animals in which the recombinant gene is found, or in which the recombinant gene is expressed in some but not all cells of the animal. The term "tissue-specific chimeric animal" indicates that one of the recombinant HDx genes is present and/or expressed or disrupted in some tissues but not others.

As used herein, the term "transgene" means a nucleic acid sequence (encoding, e.g., one of the HDx polypeptides, or pending an antisense transcript thereto), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

As is well known, genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding an HDx polypeptide" may thus refer to one or more genes within a particular individual. Moreover, certain differences in nucleotide sequences may exist between individuals of the same species, which are called alleles. Such allelic differences may or may not result in differences in amino acid sequence of the encoded polypeptide yet still encode a protein with the same biological activity.

The term "nucleotide sequence complementary to the nucleotide sequence set forth in SEQ ID No. x" refers to the nucleotide sequence of the complementary strand of a nucleic acid strand having SEQ ID No. x. The term "complementary strand" is used herein interchangeably with the term "complement". The complement of a nucleic acid strand can be the complement of a coding strand or the complement of a non-coding strand. When referring to double stranded nucleic acids, the complement of a nucleic acid having SEQ ID No. x refers to the complementary strand of the strand having SEQ ID No. x or to any nucleic acid having the nucleotide sequence of the complementary strand of SEQ ID No. x. When referring to a single stranded nucleic acid having the nucleotide sequence SEQ ID No. x, the complement of this nucleic acid is a nucleic acid having a nucleotide sequence which is complementary to that of SEQ ID No. x. The nucleotide sequences and complementary sequences thereof are always given in the 5' to 3' direction.

The term "percent identical" refers to sequence identity between two amino acid sequences or between two nucleotide sequences. Identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

Other techniques for alignment are described in *Methods in Enzymology*, vol. 266: Computer Methods for Macromolecular Sequence Analysis (1996), ed. Doolittle, Academic Press, Inc., a division of Harcourt Brace & Co., San Diego, Calif., USA. Preferably, an alignment program that permits gaps in the sequence is utilized to align the sequences. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

Databases with individual sequences are described in *Methods in Enzymology*, ed. Doolittle, supra. Databases include Genbank, EMBL, and DNA Database of Japan (DDBJ).

Preferred nucleic acids have a sequence at least 70%, and more preferably 80% identical and more preferably 90% and even more preferably at least 95% identical to an nucleic acid sequence of a sequence shown in one of SEQ ID Nos. of the invention. Nucleic acids at least 90%, more preferably 95%, and most preferably at least about 98-99% identical with a nucleic sequence represented in one of SEQ ID Nos: 1-4 are of course also within the scope of the invention. In preferred embodiments, the nucleic acid is mammalian. In comparing a new nucleic acid with known sequences, several alignment tools are available. Examples include PileUp, which creates a multiple sequence alignment, and is described in Feng et al., J. Mol. Evol. (1987) 25:351-360. Another method, GAP, uses the alignment method of Needleman et al., J. Mol. Biol. (1970) 48:443-453. GAP is best suited for global alignment of sequences. A third method, BestFit, functions by inserting gaps to maximize the number of matches using the local homology algorithm of Smith and Waterman, Adv. Appl. Math. (1981) 2:482-489.

"Homology" and "identity" each refer to sequence similarity between two polypeptide sequences, with identity being a more strict comparison. Homology and identity can each be determined by comparing a position in each sequence which may be aligned for purposes of comparison. When a position in the compared sequence is occupied by the same amino acid residue, then the polypeptides can be referred to as identical at that position; when the equivalent site is occupied by the same amino acid (e.g., identical) or a similar amino acid (e.g., similar in steric and/or electronic nature), then the molecules can be referred to as homologous at that position. A percentage of homology or identity between sequences is a function of the number of matching or homologous positions shared by the sequences. An "unrelated" or "non-homologous" sequence shares less than 40 percent identity, though preferably less than 25 percent identity, with an HDx sequence of the present invention.

As used herein, an "HDx-related protein" refers to the HDx proteins described herein, and other human homologs of those HDx sequences, as well as orthologs and paralogs (homologs) of the HDx proteins in other species, ranging from yeast to other mammals, e.g., homologous histone deacetylase. The term "ortholog" refers to genes or proteins which are homologs via speciation, e.g., closely related and assumed to have common descent based on structural and functional considerations. Orthologous proteins function as recognizably the same activity in different species. The term "paralog" refers to genes or proteins which are homologs via gene duplication, e.g., duplicated variants of a gene within a genome. See also, Fritch, W M (1970) Syst Zool 19: 99-113.

"Cells", "host cells", or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric protein" or "fusion protein" is a fusion of a first amino acid sequence encoding one of the subject HDx polypeptides with a second amino acid sequence defining a domain (e.g. polypeptide portion) foreign to and not substantially homologous with any domain of one of the HDx proteins. A chimeric protein may present a foreign domain which is found (albeit in a different protein) in an organism which also expresses the first protein, or it may be an "interspecies", "intergenic", etc. fusion of protein structures expressed by different kinds of organisms. In general, a fusion protein can be represented by the general formula X-HDx-Y, wherein HDx represents a portion of the protein which is derived from one of the HDx proteins, and X and Y are, independently, absent or represent amino acid sequences which are not related to one of the HDx sequences in an organism.

The term "isolated" as also used herein with respect to nucleic acids, such as DNA or RNA refers to molecules separated from other DNAs, or RNAs, respectively, that are present in the natural source of the macromolecule. For example, an isolated nucleic acid encoding one of the subject HDx polypeptides preferably includes no more than 10 kilobases (kb) of nucleic acid sequence which naturally immediately flanks the HDx gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

DETAILED DESCRIPTION OF THE INVENTION

The positioning of nucleosomes relative to particular regulatory elements in genomic DNA has emerged as a mechanism for managing the association of sequence specific DNA-binding proteins with promoters, enhancers and other transcriptional regulatory sequences. Two modifications to nucleosomes have been observed to influence the association of DNA-binding proteins with chromatin. Depletion of histones H2A/H2B from the nucleosome facilitates the binding of RNA polymerase II (Baer et al. (1983) Nature 301: 482-488) and TFIIIA (Hayes et al. (1992) PNAS 89:1229-1233). Likewise, acetylation of the core histones apparently destabilizes the nucleosome and is thought to modulate the accessibility of transcription factors to their respective enhancer and promoter elements (Oliva et al. (1990) Nuc. Acid Res. 18: 2739-2747; and Walker et al. (1990) J. Biol. Chem. 265: 5622-5746). In both cases, overall histone-DNA contacts are altered.

In one aspect, the present invention concerns the discovery of new class of histone deacetylase genes in mammals, the gene products of which are referred to herein as "histone deacetylases" or HDx's. Experimental evidence indicates a functional role for the HDx gene products as catalysts of the deacetylation of histones in mammalian cells, and accordingly play a role in determining tissue fate and maintenance. In addition, however, other experimental evidence indicates a role that is biochemically distinct from other classes of HDAC (class I), whereby regulation of cellular localization is involved in the control of the transcriptional activity of HDAC proteins.

The new class of histone deacetylase genes encode at least three different sub-families, e.g., paralogs, and have been identified from the cells of various mammals. The HDx gene products described herein are referred to as HD4, HD5 and HD6, and are represented in SEQ ID No.'s 1-10.

As described below, one aspect of the invention pertains to isolated nucleic acids comprising nucleotide sequences encoding HDx polypeptides, and/or equivalents of such nucleic acids. The term nucleic acid as used herein is intended to include fragments as equivalents. The term equivalent is understood to include nucleotide sequences encoding functionally equivalent HDx polypeptides or functionally equivalent peptides having an activity of an HDx protein such as described herein. Equivalent nucleotide sequences will include sequences that differ by one or more nucleotide substitutions, additions, or deletions, such as allelic variants; and will, therefore, include sequences that differ from the nucleotide sequence of the HDx cDNA sequences shown in any of SEQ ID Nos: 1, 3 or 5, due to the degeneracy of the genetic code. Equivalents will also include nucleotide sequences that hybridize under stringent conditions (i.e., equivalent to about 20-27° C. below the melting temperature (TM) of the DNA duplex formed in about 1M salt) to the nucleotide sequences represented in one or more of SEQ ID Nos: 1, 3, or 5.

Moreover, it will be generally appreciated that, under certain circumstances, it may be advantageous to provide homologs of one of the subject HDx polypeptides which function in a limited capacity as one of either an HDx agonist (mimetic) or an HDx antagonist, in order to promote or inhibit only a subset of the biological activities of the naturally occurring form of the protein. Thus, specific biological effects can be elicited by treatment with a homolog of limited function, and with fewer side effects relative to treatment with agonists or antagonists which are directed to all of the biological activities of naturally occurring forms of HDx proteins.

Homologs of the subject HDx proteins can be generated by mutagenesis, such as by discrete point mutation(s), or by truncation. For instance, mutation can give rise to homologs which retain substantially the same, or merely a subset, of the biological activity of the HDx polypeptide from which it was derived. Alternatively, antagonistic forms of the protein can be generated which are able to inhibit the function of the naturally occurring form of the protein, as for example competing with wild-type HDx in the binding of a 14-3-3 protein, a MEF2 transcription factor, RbAp48 or a histone. In addition, agonistic forms of the protein may be generated which are constitutively active, or have an altered $K_{cat}$ or $K_m$ for deacetylation reactions. Thus, the HDx protein and homologs thereof provided by the subject invention may be either positive or negative regulators of transcription and/or activation.

In general, polypeptides referred to herein as having an activity of an HDx protein (e.g., are "bioactive") are defined as polypeptides which include an amino acid sequence corresponding (e.g., identical or homologous) to all or a portion of the amino acid sequences of an HDx protein shown in any one or more of SEQ ID Nos. 2, 4, 6, 7, 8, 9 or 10, which mimic or antagonize all or a portion of the biological/biochemical activities of a naturally occurring HDx protein. Examples of such biological activity include the ability to modulate proliferation of cells. For example, inhibiting histone deacetylation causes cells to arrest in G1 and G2 phases of the cell cycle. The biochemical activity associated with HDx proteins of the present invention can also be characterized in terms of binding to and (optionally) catalyzing the deacetylation of an acetylated histone.

Other biological activities of the subject new class of HDx proteins are described herein or will be reasonably apparent to those skilled in the art. According to the present invention, a polypeptide has biological activity if it is a specific agonist or antagonist of a naturally occurring form of an HDx protein.

A. Exemplary Nucleic Acids

Analysis of the new class of HDx sequences indicated similarity with the original class of HDx (HD1) and x conserved residues are found. This, along with other experimental data suggests a role in the new class of human HDx genes in the deacetylation of histones in mammalian cells. In addition, however, the new class of HDx proteins each contains a novel and conserved catalytic region represented by the consensus sequence:

(SEQ ID No.: 7)
HHAXXXXXXGXCXFNXVAXXAXXXQXXXXXXXXXXXLIVDWDXHHGXGTQX

XFXXDPSVLYXSXHRYXXGXFXPXX

With reference to HD4, this catalytic region corresponds to amino acid residues 802-874 of SEQ ID No. 2; with reference to HD5, this catalytic region corresponds to amino acid residues 832-905 of SEQ ID No. 4; and with respect to HD6, this catalytic region corresponds to two catalytic regions corresponding to amino acid residues 215-287 and amino acid residues 610-683 of SEQ ID No. 6.

In another aspect, the invention provides a method of inhibiting a class II HDx. The method comprises contacting the HDx with a compound capable of initiating HDx activity, under conditions such that HDx activity is inhibited.

In another aspect, the invention provides a method of purifying an HDx. The method includes contacting a reaction mixture comprising an HDx with an affinity matrix capable of selectively binding to an HDx, and separating at least one other component of the reaction mixture from the HDx.

Another aspect of the present invention relates to a method of inducing and/or maintaining a differentiated state, enhancing survival, and/or inhibiting (or alternatively potentiating) proliferation of a cell, by contacting the cells with an agent which modulates HDx-dependent transcription. For instance, it is contemplated by the invention that, in light of the present finding of an apparently broad involvement of HDx proteins in the control of chromating structure and, thus, transcription and replication, the subject method could be used to generate and/or maintain an array of different tissue both in vitro and in vivo. An "HDx therapeutic", whether inhibitory or potentiating with respect to modulating histone deacetylation, can be, as appropriate, any of the preparations described above, including isolated polypeptides, gene therapy constructs, antisense molecules, peptidomimetics or agents identified in the drug assays provided herein.

In a further embodiment of the invention, the subject HDx therapeutics will be useful in increasing the amount of protein produced by a cell or recombinant cell. The cell may include any primary cell isolated from any animal, cultured cells, immortalized cells, and established cell lines. The animal cells used in the present invention include cells which intrinsically have an ability to produce a desired protein; cells which are induced to have an ability to produce a desired protein, for example, by stimulation with a cytokine such as an interferon, an interleukin; genetically engineered cells into which a gene for a desired protein is introduced. The protein produced by the process could include any peptides or proteins, including peptide hormone or proteinaceous hormones such as any useful hormone, cytokine, interleukin, or protein which it may be desirable to have in purified form and/or in large quantity.

Another aspect of the invention features transgenic non-human animals which express a heterologous HDx gene of the present invention, or which have had one or more genomic HDx genes disrupted in at least one of the tissue or cell-types of the animal. Accordingly, the invention features an animal model for developmental diseases, which animal has one or more HDx allele which is mis-expressed. For example, a mouse can be bred which has one or more HDx alleles deleted or otherwise rendered inactive. Such a mouse model can then be used to study disorders a rising from mis-expressed HDx genes, as well as for evaluating potential therapies for similar disorders.

Another aspect of the present invention concerns transgenic animals which are comprised of cells (of that animal) which contain a transgene of the present invention and which preferably (though optionally) express an exogenous HDx protein in one or more cells in the animal. An HDx transgene can encode the wild-type form of the protein, or can encode homologs thereof, including both agonists and antagonists, as well as antisense constructs. In preferred embodiments, the expression of the transgene is restricted to specific subsets of cells, tissues or developmental stages utilizing, for example, cis-acting sequences that control expression in the desired pattern. In the present invention, such mosaic expression of an HDx protein can be essential for many forms of lineage analysis and can additionally provide a means to assess the effects of, for example, lack of HDx expression which might grossly alter development in small patches of tissue within an otherwise normal embryo. Toward this end, tissue-specific regulatory sequences and conditional regulatory sequences can be used to control expression of the transgene in certain spatial patterns. Moreover, temporal patterns of expression can be provided by, for example, conditional recombination systems of prokaryotic transcriptional regulatory sequences.

Genetic techniques which allow for the expression of transgenes can be regulated via site-specific genetic manipulation in vivo are know to those skilled in the art. For instance, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of one of the subject HDx proteins. For example, excision of a target sequence which interferes with the expression of a recombinant HDx gene, such as one which encodes an antagonistic homolog or an antisense transcript, can be designed to activate expression of that gene. This interference with expression of the protein can result from a variety of mechanisms, such as spatial separation of the HDx gene from the promoter element or an internal stop codon. Moreover, the transgene can be made wherein the coding sequence of the gene is flanked by recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allows for promoter driven transcriptional activation.

Similar conditional transgenes can be provided using prokaryotic promoter sequences which require prokayrotic proteins to be simulataneously expressed in order to facilitate expression of the HDx transgene. Exemplary promoters and the corresponding transactivating prokaryotic proteins are given in U.S. Pat. No. 4,833,080.

Moreover, expression of the conditional transgenes can be induced by gene therapy-like methods wherein a gene encoding the trans-activating protein, e.g., a recombinase or a prokaryotic protein, is delivered to the tissue and caused to be expressed, such as in a cell-type specific manner. By this method, an HDx transgene could remain silent into adulthood until "turned on" by the introduction of the transactivator.

In an exemplary embodiment, the "transgenic non-human animals" of the invention are produced by introducing transgenes into the germline of the non-human animal. Embryic target cells at various developmental stages can be used to introduce transgenes. Different methods are used depending on the stage of development of the embryonic target cell. The zygote is the best target for micro-injection. In the mouse, the male pronucleus reaches the size of approximately 20 micrometers in diameter which allows reproducible injection of 1-2 pl of DNA solution. The use of zygotes as a target for gene transfer has a major advantage in that in most cases the injected DNA will be incorporated into the host gene before the first cleavage (Brinster et al. (1985) PNAS 82:4438-4442). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

Retroviral infection can also be used to introduce HDx transgenes into a non-human animal. The developing non-human embryo can be cultured in vitro to the blastocyst stage. During this time, the blastomeres can be targets for retroviral infection (Jaenich, R. (1976) PNAS 73:1260-1264). Efficient infection of the blastomeres is obtained by enzymatic treatment to remove the zona pellucida (Manipulating the Mouse Embryo, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) PNAS 82:6927-6931; Van der Putten et al. (1985) PNAS 82:6148-6152). Transfection is easily and efficiently obtained by culturing the blastomeres on a monolayer of virus-producing cells (Van der Putten, supra; Stewart et al. (1987) EMBO J. 6: 383-388). Alternatively, infection can be performed at a later stage. Virus or virus-producing cells can be injected into the blastocoele (Jahner et al. (1982) Nature 298: 623-628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonic stem cell (ES). ES cells are obtained from pre-implantation embryos cultured in vitro and fused with embryos (Evans et al (1981) Nature 292: 154-156; Bradley et al. (1984) Nature 309: 255-258; Gossler et al. (1986) PNAS 83: 9065-9069; and Robertson et al (1986) Nature 322: 445-448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) Science 240: 1468-1474.

Methods of making HDx knock-out of disruption transgenic animals are also generally known. See, for example, Manipulating the Mouse Embryo, (Cold Spring Harbor Laboratory Press, Cold Spring Harbor, N.Y., 1986). Recombinase dependent knockouts can also be generated, e.g., by homologous recombination to insert recombinase target sequences flanking portions of an endogenous HDx gene, such that tissue specific and/or temporal control of inactivation of an HDx allele can be controlled as above.

B. Exemplary Polypeptides

The present invention makes available isolated HDx polypeptides which are isolated from, or otherwise substantially free of other cellular proteins. The term "substantially free of other cellular proteins" (also referred to herein as "contaminating proteins") or "substantially pure or purified preparations" are defined as encompassing preparations of HDx polypeptides having less than about 20% (by dry weight) contaminating protein, and preferably having less than about 5% contaminating protein. Functional forms of the subject polypeptides can be prepared, for the first time, as purified preparations by using a cloned gene as described herein.

Preferred HDx proteins of the invention have an amino acid sequence which is at least about 60%, 70%, 80%, 85%, 90%, or 95% identical or homologous to an amino acid sequence of any one of SEQ ID Nos. 1, 3 or 5. Even more preferred HDx proteins comprise an amino acid sequence which is at least about 97, 98, or 99% homologous or identical to an amino acid sequence of any one of SEQ ID Nos. 1, 3, or 5. Such proteins can be recombinant proteins, and can be, e.g., produced in vitro from nucleic acids comprising a nucleotide sequence set forth in SEQ ID Nos. 1, 3, or 5, or homologs thereof. For example, recombinant polypeptides preferred by the present invention can be encoded by a nucleic acid, which is at least 85% homologous and more preferably 90% homologous and most preferably 95% homologous with a nucleotide sequence set forth in SEQ ID NOS. 1, 3 or 5. Polypeptides which are encoded by a nucleic acid that is at least about 98-99% homologous with the sequence of SEQ ID NOS: 1, 3 or 5 are also within the scope of the invention.

In a preferred embodiment, an HDx protein of the present invention is a mammalian HDx protein, and more preferably a human HDx protein. In a particularly preferred embodiment an HDx protein is set forth as SEQ ID No: 2, 4 or 6. In particularly preferred embodiment, an HDx protein has an HDx bioactivity. It will be understood that certain post-translational modifications, e.g., phosphorylation and the like, can increase the apparent molecular weight of the HDx protein relative to the unmodified polypeptide chain.

HDx polypeptides preferably are capable of functioning in one of either role of an agonist or antagonist of at least one biological activity of a wild-type ("authentic") HDx protein of the appended sequence listing. The term "evolutionarily related to", with respect to amino acid sequences of HDx proteins, refers to both polypeptides having amino acid sequences which have arisen naturally, and also to mutational variants of human HDx polypeptides which are derived, for example, by combinatorial mutagenesis. Full length proteins or fragments corresponding to one or more particular motifs and/or domains or to arbitrary sizes, for example, at least 5, 10, 25, 50, 75 and 100, amino acids in length are within the scope of the present invention.

For example, isolated HDx polypeptides can be encoded by all or a portion of a nucleic acid sequence shown in any of SEQ ID NOS. 1, 3 or 5. Isolated peptidyl portions of HDx proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, an HDx polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") HDx protein.

In general, polypeptides referred to herein as having an activity (e.g., are "bioactive") of an HDx protein are defined as polypeptides which include an amino acid sequence encoded by all or a portion of the nucleic acid sequences shown in one of SEQ ID NOS: 1, 3 or 5, and which mimic or antagonize all or a portion of the biological/biochemical activities of a naturally occurring HDx protein. Examples of such biological activity include the ability to deacetylate histones, bind to histone(s), 14-3-3 proteins, MEF2 transcription factors and/or RbAp48. Other biological activities of the subject HDx proteins are described herein or will be reasonably apparent to those skilled in the art. According to the present invention, a polypeptide has biological activity if it is a specific agonist or antagonist of a naturally-occurring form of an HDx protein.

Other preferred proteins of the invention are those encoded by the nucleic acids set forth in the section pertaining to nucleic acids of the invention. In particular, the invention provides fusion proteins, e.g., HDx-immunoglobulin fusion proteins. Such fusion proteins can provide, e.g., enhanced stability and solubility of HDx proteins and may thus be useful in therapy.

In addition to utilizing fusion proteins to enhance immunogenicity, it is widely appreciated that fusion proteins can also facilitate the expression of proteins, and accordingly, can be used in the expression of the HDx polypeptides of the present invention. For example, HDx polypeptides can be generated as glutathione-S-transferase (GST-fusion) proteins. Such GST-fusion proteins can enable easy purification of the HDx polypeptide, as for example by the use of glutathione-derivatized matrices (see, for example, Current Protocols in Molecular Biology, eds. Ausubel et al. (N.Y.: John Wiley & Sons, 1991)).

The present invention further pertains to methods of producing the subject HDx polypeptides. For example, a host cell transfected with a nucleic acid vector directing expression of a nucleotide sequence encoding the subject polypeptides can be cultured under appropriate conditions to allow expression of the peptide to occur. Suitable media for cell culture are well known in the art. The recombinant HDx polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant HDX polypeptide is a fusion protein containing a domain which facilitates its purification, such as GST fusion protein.

Moreover, it will be generally appreciated that, under certain circumstances, it may be advantageous to provide homologs of one of the subject HDX polypeptides which function in a limited capacity as one of either an HDX agonist (mimetic) or an HDX antagonist, in order to promote or inhibit only a subset of the biological activities of the naturally-occurring form of the protein. Thus, specific biological effects can be elicited by treatment with a homolog of limited function, and with fewer side effects relative to treatment with agonists or antagonists which are directed to all of the biological activities of naturally occurring forms of HDX proteins.

Homologs of each of the subject HDX proteins can be generated by mutagenesis, such as by discrete point mutation(s), or by truncation. For instance, mutation can give rise to homologs which retain substantially the same, or merely a subset, of the biological activity of the HDX polypeptide from which it was derived. Alternatively, antagonistic forms of the protein can be generated which are able to inhibit the function of the naturally occurring form of the protein, such as by competitively binding to an HDX receptor.

The recombinant HDX polypeptides of the present invention also include homologs of the wildtype HDX proteins, such as versions of those protein which are resistant to proteolytic cleavage, as for example, due to mutations which alter ubiquitination or other enzymatic targeting associated with the protein.

HDX polypeptides may also be chemically modified to create HDX derivatives by forming covalent or aggregate conjugates with other chemical moieties, such as glycosyl groups, lipids, phosphate, acetyl groups and the like. Covalent derivatives of HDX proteins can be prepared by linking the chemical moieties to functional groups on amino acid sidechains of the protein or at the N-terminus or at the C-terminus of the polypeptide.

Modification of the structure of the subject HDX polypeptides can be for such purposes as enhancing therapeutic or prophylactic efficacy, stability (e.g., ex vivo shelf life and resistance to proteolytic degradation), or post-translational modifications (e.g., to alter phosphorylation pattern of protein). Such modified peptides, when designed to retain at least one activity of the naturally-occurring form of the protein, or to produce specific antagonists thereof, are considered functional equivalents of the HDX polypeptides described in more detail herein. Such modified peptides can be produced, for instance, by amino acid substitution, deletion, or addition. The substitutional variant may be a substituted conserved amino acid or a substituted non-conserved amino acid.

For example, it is reasonable to expect that an isolated replacement of a leucine with an isoleucine or value, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine, (see, for example, Biochemistry, $2^{nd}$ ed., Ed. by L. Stryer, WH Freeman and Co.: 1981). Whether a change in the amino acid sequence of a peptide results in a functional HDX homolog (e.g., functional in the sense that the resulting polypeptide mimics or antagonizes the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

This invention further contemplates a method for generating sets of combinatorial mutants of the subject HDX proteins as well as truncation mutants, and is especially useful for identifying potential variant sequences (e.g., homologs). The purpose of screening such combinatorial libraries is to generate, for example, novel HDX homologs which can act as either agonists or antagonist, or alternatively, possess novel activities all together. Thus, combinatorially-derived homologs can be generated to have an increased potency relative to a naturally occurring form of the protein.

In one embodiment, the variegated library of HDX variants is generated by combinatorial mutagenesis at the nucleic acid level, and is encoded by a variegated gene library. For instance, a mixture of synthetic oligonucleotides can be enzymatically ligated into gene sequences such that the degenerate set of potential HDX sequences are expressible as individual polypeptides, or alternatively, as a set of larger fusion proteins (e.g., for phage display) containing the set of HDX sequences therein.

There are many ways by which such libraries of potential HDX homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential HDX sequences. The synthesis of degenerate oligonucleotides is well known in the art (see for example, Narang, S A (1983) Tetrahedron 39:3; Itakura et al. (1981) Recombinant DNA, Proc $3^{rd}$ Cleveland Sympos. Macromolecules, ed. A G Walton, Amsterdam: Elsevier pp 273-289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins (see, for example, Scott et al. (1990) Science 249:386-390; Roberts et al. (1992) PNAS 89:2429-2433; Devlin et al. (1990) Science 249: 404-406; Cwirla et al. (1990) PNAS 87: 6378-6382; as well as U.S. Pat. Nos. 5,223,409, 5,198,346, and 5,096,815).

Likewise, a library of coding sequence fragments can be provided for an HDX clone in order to generate a variegated population of HDX fragments for screening and subsequent selection of bioactive fragments. A variety of techniques are known in the art for generating such libraries, including chemical synthesis. In one embodiment, a library of coding sequence fragments can be generated by (i) treating a double stranded PCR fragment of an HDX coding sequence with a nuclease under conditions wherein nicking occurs only about once per molecule; (ii) denaturing the double stranded DNA; (iii) renaturing the DNA to form double stranded DNA which can include sense/antisense pairs from different nicked products; (iv) removing single stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of HDX homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate HDX sequences created by combinatorial mutagenesis techniques. Combinatorial mutagenesis has a potential to generate very large libraries of mutant proteins, e.g., in the order of $10^{26}$ molecules. Combinatorial libraries of this size may be technically challenging to screen even with high throughput screening assays. To overcome this problem, a new technique has been developed recently, retrusive ensemble mutagenesis (REM), which allows one to avoid the very high proportion of non-functional proteins in a random library and simply enhances the frequency of functional proteins, thus decreasing the complexity required to achieve a useful sampling of sequence space. REM is an algorithm which enhances the frequency of functional mutants in a library when an appropriate selection or screening method is employed (Arkin and Yourvan, 1992, PNAS USA 89:7811-7815; Yourvan et al., 1992, Parallel Problem Solving from Nature, 2. In Maenner and Manderick, eds., Elsevier Publishing Co., Amsterdam, pp. 401-410; Delgrave et al., 1993, Protein Engineering 6(3):327-331).

The invention also provides for reduction of the HDX proteins to generate mimetics, e.g., peptide or non-peptide agents, such as small molecules, which are able to disrupt binding of an HDX polypeptide of the present invention with a molecule, e.g. target peptide. Thus, such mutagenic techniques as described above are also useful to map the determinants of the HDX proteins which participate in protein-protein interactions involved in, for example, binding of the subject HDX polypeptide to a target peptide. To illustrate, the critical residues of a subject HDX polypeptide which are involved in molecular recognition of its receptor can be determined and used to generate HDX derived peptidomimetics or small molecules which competitively inhibit binding of the authentic HDX protein with that moiety. By employing, for example, scanning mutagenesis to map the amino acid residues of the subject HDX proteins which are involved in binding other proteins, peptidomimetic compounds can be generated which mimic those residues of the HDX protein which facilitate the interaction. Such mimetics may then be used to interfere with the normal function of an HDX protein. For instance, non-hydrolyzable peptide analogs of such residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) J Med Chem 29:295; and Ewenson et al. in Peptides: Structure and Function (Proceedings of the $9^{th}$ American Peptide Symposium) Pierce Chemical Co. Rockland, Ill., 1985), b-turn dipeptide cores (Nagai et al. (1985) Tetrahedron Lett 26:647; and Sato et al. (1986) J Chem Soc Perkin Trans 1:1231), and b-aminoalcohols (Gordon et al. (1985) Biochem Biophys Res Commun 126:419; and Dann et al. (1986) Biochem Biophys Res Commun 134:71).

C. HDx Antibodies

Another aspect of the invention pertains to an antibody specifically reactive with an HDx protein. For example, by using immunogens derived from an HDx protein, e.g., based on the cDNA sequences, anti-protein/anti-peptide antisera or monoclonal antibodies can be made by standard protocols (See, for example, Antibodies: A Laboratory Manual ed. By Halow and Lane (Cold Spring Harbor Press: 1988)). A mammal, such as a mouse, a hamster or rabbit can be immunized with an immunogenic form of the peptide (e.g., an HDx polypeptide or an antigenic fragment which is capable of eliciting an antibody response). Techniques for conferring immunogenicity on a protein or peptide include conjugation to carriers or other techniques well known in the art. An immunogenic portion of an HDx protein can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of a class II HDx protein of an organism, such as a mammal, e.g, antigenic determinants of a protein represented by one of SEQ ID Nos, or closely related homologs (e.g., at least 85% homologous, preferably at least 90% homologous, and more preferably at least 90% identical). In yet a further embodiment of the present invention, in order to provide, for example, antibodies which are immuno-selective for discrete HDx homologs, e.g, HDAC 4, HDAC5 or HDAC6, the anti-HDx polypeptide antibodies do not substantially cross react (i.e., does not react specifically) with a protein which is, for example, less than 85%, 90% or 95% homologous with the selected HDx. By "not substantially cross react", it is meant that the antibody has a binding affinity for a non-homologous protein which is at least one order of magnitude, more preferably at least 2 orders of magnitude, and even more preferably at least 3 orders of magnitude less than the binding affinity of the antibody for the intended target HDx.

Following immunization of an animal with an antigenic preparation of an HDx polypeptide, anti-HDx antisera can be obtained and, if desired, polyclonal anti-HDx antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with an HDx polypeptide of the present invention and monoclonal antibodies isolated from a culture comprising such hybridoma cells.

The term antibody, as used herein, is intended to include fragments thereof which are also specifically reactive with one of the subject HDx polypeptides. Antibodies can be fragmented using conventional techniques and the fragments screened for utility in the same manner as described above for whole antibodies. For example F(ab)2 fragments can be generated by treating antibody with pepsin. The resulting F(ab)2 fragment can be treated to reduce disulfide bridges to produce Fab fragments. The antibody of the present invention is further intended to include bispecific and chimeric molecules having affinity for an HDx protein conferred by at least one CDR region of the antibody.

Both monoclonal and polyclonal antibodies (Ab) directed against authentic HDx polypeptides, or HDx variants, and antibody fragments such as Fab, F(ab)$_2$, Fv and scFv can be used to block the action of one or more HDx proteins and allow the study of the role of these proteins in, for example, differentiation of tissue. Experiments of this nature can aid in deciphering the role of HDx proteins that may be involved in control of proliferation versus differentiation, e.g., in patterning and tissue formation.

Antibodies which specifically bind HDx epitopes can also be used in immunohistochemical staining of tissue samples in order to evaluate the abundance and pattern of expression of each of the subject HDx polypeptides. Anti-HDx antibodies can be used diagnostically in immuno-precipitation and immuno-blotting to detect and evaluate HDx protein levels in tissue as part of a clinical testing procedure. For instance, such measurements can be useful in predictive valuations of the onset or progression of proliferative or differentiative disorders. Likewise, the ability to monitor HDx protein levels in an individual can allow determination of the efficacy of a given treatment regimen for an individual affected with such a disorder. The level of HDx polypeptides may be measured from cells in bodily fluid, such as in samples of cerebral spinal fluid or amniotic fluid, or can be measured in tissue, such as produced by biopsy. Diagnostic assays using anti-HDx antibodies can include, for example, immunoassays designed to aid in early diagnosis of a disorder, particularly ones which are manifest at birth. Diagnostic assays using anti-HDx polypeptide antibodies can also include immunoassays designed to aid in early diagnosis and phenotyping neoplastic or hyperplastic disorders.

D. HDx Therapeutic Agents

As discussed above, purified and recombinant HDx polypeptides are made available by the present invention and thus facilitates the development of assays which can be used to screen for drugs, including HDx homologs, which are either agonists of antagonists of the normal cellular function of the subject HDx polypeptides, or of their role in the pathogenesis of cellular differentiation and/or proliferation and disorders related thereto. In certain embodiments, the subject method is used to identify a gents which potentiate or inhibit the deacetylase activity of an HDx protein. Moreover, because proteins have been identified which bind to the subject HDx proteins, e.g., such as histones, 14-3-3 proteins, MEF2 transcription factor, and RbAp48 as, the present invention further provides drug screening assays for detecting agents which modulate those interactions.

In a general sense, the assay evaluates the ability of a compound to modulate binding between an HDx polypeptide and a molecule, be it protein or DNA, that interacts with the HDx polypeptide, be it a substrate of the deacetylase, or serves a regulatory function. Exemplary compounds which can be screened include peptides, nucleic acids, carbohydrates, small organic molecules, and natural product extract libraries, such as isolated from animals, plants, fungus and/or microbes.

It is contemplated that any of the novel interactions described herein could be exploited in a drug screening assay. To illustrate, the interaction between an HDx protein and a histone, a 14-3-3 protein or other HDx-binding protein can be detected in the presence and the absence of a test compound. In other embodiments, the ability of a compound to modulate the acetylase activity of an HDx protein can be assessed. A variety of assay formats will suffice and, in light of the present inventions, will be comprehended by a skilled artisan.

In a preferred embodiment, assays which employ the subject mammalian HDx proteins can be used to identify compounds that have therapeutic indexes more favorable than sodium butyrate, trapoxin, trichostatin or the like. For instance, trapoxin-like drugs can be identified by the present invention which have enhanced tissue-type or cell-type specificity relative to trapoxin. To illustrate, the subject assays can be used to generate compounds which preferentially inhibit IL-2 mediated proliferation/activation of lymphocytes, or inhibit proliferation of certain tumor cells, without substantially interfering with other tissues, e.g. hepatocytes. Likewise, similar assays can be used to identify drugs which inhibit proliferation of yeast cells or other lower eukaryotes, but which have a substantially reduced effect on mammalian cells, thereby improving therapeutic index of the drug as an anti-mycotic agent.

In one embodiment, the identification of such compounds is made possible by the use of differential screening assays which detect and compare drug-mediated inhibition of deacetylase activity or protein-protein or protein-DNA interactions involving two or more different HDx enzymes, e.g., to find compounds that selectively inhibit class I or class I HDx proteins relative to one another or selectively inhibit one HDx protein relative to all the others. To illustrate, the assay can be designed for side-by-side comparison of the effect of a test compound on the deacetylase activity or protein interactions of tissue-type specific HDx proteins. Given the apparent diversity of HDx proteins, it is probable that different functional HDx activities, or HDx complexes exist and, in certain instances, are localized to particular tissue or cell types. Thus, test compounds can be screened for agents able to inhibit the tissue-specific formation of only a subset of the possible repertoire of HDx/regulatory protein complexes, or which preferentially inhibit certain HDx enzymes. In an exemplary embodiment, an interaction trap assay can be derived using class I and class II HDx "bait" proteins, while the "fish" protein is constant in each, e.g., a human RbAp48 construct. Running the interaction trap side-by-side permits the detection for agents which have a greater effect (e.g., statistically significant) on the formation of one of the class I HDx/RbAp48 complexes than on the formation of the class I HDx/RbAp48 complexes.

In similar fashion, differential screening assays can be used to exploit the difference in protein interactions and/or catalytic mechanism of mammalian HDx proteins and yeast RPD3 proteins in order to identify agents which display a statistically significant increase in specificity for inhibiting the yeast enzyme relative to the mammalian enzyme. Thus, lead compounds which act specifically on pathogens, such as fungus involved in mycotic infections, can be developed. By way of illustration, the present assays can be used to screen for agents which may ultimately be useful for inhibiting at least one fungus implicated in such mycosis as candidiasis, aspergillosis, mucormycosis, blastomycosis, geotrichosis, cryptococcosis, chromoblastomycosis, coccidioidomycosis, conidiosporosis, histoplasmosis, maduromycosis, rhinosporidosis, nocaidiosis, para-actinomycosis, penicilliosis, monoliasis, or sporotrichosis. For example, if the mycotic infection to which treatment is desired is candidiasis, the present assay can comprise comparing the relative effectiveness of a test compound on inhibiting the deacetylase activity of a mammalian HDx protein with its effectiveness towards inhibiting the deacetylase activity of an RPD3 homolog cloned from yeast selected from the group consisting of *Candida albicans, Candida stellatoidea, Candida tropicalis, Candida parapsilosis, Candida krusei, Candida pseudotropicalis, Candida quillermondii*, or *Candida rugosa*. Likewise, the present assay can be used to identify anti-fungal agents which may have therapeutic value in the treatment of aspergillosis by selectively targeting RPD3 homologs cloned from yeast such as *Aspergillus fumigatus, Aspergillus flavus, Aspergillus niger, Aspergillus nidulans*, or *Aspergillus terreus*. Where the mycotic infection is mucormycosis, the RPD3 deacetylase can be derived from yeast such as *Rhizopus arrhizus, Rhizopus oryzae, Absidia corymbifera, Absidia ramosa*, or *Mucor pusillus*. Sources of other RPD3 activities for comparison with a mammalian HDx activity includes the pathogen *Pneumocystis carinii*.

In addition to such HDx therapeutic uses, anti-fungal agents developed with such differential screening assays can be used, for example, as preservatives in foodstuff, feed supplement for promoting weight gain in livestock, or in disinfectant formulations for treatment of non-living matter, e.g., for decontaminating hospital equipment and rooms.

In a similar fashion, side by side comparison of inhibition of mammalian HDx proteins and an insect HDx-related proteins, will permit selection of HDx inhibitors which discriminate between the human/mammalian and insect enzymes. Accordingly, the present invention expressly contemplates the use and formulations of the subject HDx therapeutics in insecticides, such as for use in management of insects like the fruit fly.

In yet another embodiment, certain of the subject HDx inhibitors can be selected on the basis of inhibitory specificity for plant HDx-related activities relative to the mammalian enzyme. For example, a plant HDx-related protein can be disposed in a differential screen with one or more of the human enzymes to select those compounds of greatest selectivity for inhibiting the plant enzyme. Thus, the present invention specifically contemplates formulations of the subject HDx inhibitors for agricultural applications, such as in the form of a defoliant or the like.

In many drug screening programs which test libraries of compounds and natural products, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with upstream or downstream elements. Accordingly, in an exemplary screening assay of the present invention, a reaction mixture is generated to include an HDx polypeptide, compound(s) of interest, and a "target polypeptide" e.g., a protein which interacts with the HDx polypeptide, whether as a substrate or by some other protein-protein interaction. Detection and quantification of complexes containing the HDx protein provide a means for determining a compound's efficacy at inhibiting (or potentiating) complex formation between the HDx and the target polypeptide. The efficacy of the compound can be assessed by generating dose response curves from data obtained using various concentrations of the test compound. Moreover, a control assay can also be performed to provide a baseline for comparison. In the control assay, isolate and purified HDx polypeptide is added to a composition containing the target polypeptide and the formation of a complex is quantitated in the absence of the test compound.

Complex formation between the HDx polypeptide and the target polypeptide may be detected by a variety of techniques. Modulation of the formation of complexes can be quantitated using, for example, detectably labeled proteins such as radiolabeled, fluorescently labeled, or enzymatically labeled HDx polypeptides, by immunoassay, by chromatographic detection, or by detecting the intrinsic activity of the acetylase.

Typically, it will be desirable to immobilize either HDx or the target polypeptide to facilitate separation of complexes from uncomplexed forms of one or both of the proteins, as well as to accommodate automation of the assay. Binding of HDx to the target polypeptide, in the presence and absence of a candidate agent, can be accomplished in any vessel suitable for containing the reactants. Examples include microtitre plates, test tubes, and micro-centrifuge tubes. In one embodiment, a fusion protein can be provided which adds a domain that allows the protein to be bound to the matrix. For example, glutathione-S-transferase/HDx (GST/HDx) fusion proteins can be adsorbed onto glutathione sepharose beads (Sigma Chemical, St. Louis, Mo.) or glutathione derivatized microtitre plates, which are then combined with the cell lysates, e.g. an $^{35}$S-labeled, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintillant), or in the supernatant after the complexes are subsequently dissociated. Alternatively, the complexes can be dissociated from the matrix, separated by SDS-PAGE, and the level of HDx-binding protein found in the bead fraction quantitated from the gel using standard electrophoretic techniques such as described in the appended examples.

Other techniques for immobilizing proteins on matrices are also available for use in the subject assay. For instance, either HDx or target polypeptide can be immobilized utilizing conjugation of biotin and streptavidin. For instance, biotinylated HDx molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with HDx, but which do not interfere with the interaction between the HDx and target polypeptide, can be derivatized to the wells of the plate, and HDx trapped in the wells by antibody conjugation. As above, preparations of an target polypeptide and a test compound are incubated in the HDx-presenting wells of the plate, and the amount of complex trapped in the well can be quantitated. Exemplary methods for detecting such complexes, in addition to those described above for the GST-immobilized complexes, include immunodetection of complexes using antibodies reactive with the target polypeptide, or which are reactive with HDx protein and compete with the target polypeptide; as well as enzyme-linked assays which rely on detecting an enzymatic activity associated with the target polypeptide, either intrinsic or extrinsic activity. In the instance of the latter, the enzyme can be chemically conjugated or provided as a fusion protein with the target polypeptide. To illustrate, the target polypeptide can be chemically cross-linked or genetically fused with horseradish peroxidase, and the amount of polypeptide trapped in the complex can be assessed with a chromogenic substrate of the enzyme, e.g. 3,3'-diamino-benzadine terahydrochloride or 4-chloro-1-napthol. Likewise, a fusion protein comprising the polypeptide and glutathione-S-transferase can be provided, and complex formation quantitated by detecting the GST activity using 1-chloro-2,4-dinitrobenzene (Habig et al (1974) *J Biol Chem* 249:7130).

For processes which rely on immunodetection for quantitating one of the proteins trapped in the complex, antibodies against the protein, such as anti-HDx antibodies, can be used. Alternatively, the protein to be detected in the complex can be "epitope tagged" in the form of a fusion protein which includes, in addition to the HDx sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) J Biol Chem 266:21150-21157) which includes a 10-residue sequence from c-myc, as well as the pFLAG system (International Biotechnologies, Inc.) or the pEZZ-protein A system (Pharmacia, NJ).

In another embodiment of a drug screening, a two hybrid assay can be generated with an HDx and HDx-binding protein. Drug dependent inhibition or potentiation of the interaction can be scored.

Where the HDx proteins themselves, or in complexes with other proteins, are capable of binding DNA and modifying transcription of a gene, a transcriptional based assay using, for example, an transcriptional regulatory sequences responsive to HDx complexes operably linked to a detectable marker gene.

Furthermore, each of the assay systems set out above can be generated in a "differential" format as set forth above. That is, the assay format can provide information regarding specificity as well as potency. For instance, side-by-side comparison of a test compound's effect on different HDxs can provide information on selectivity, and permit the identification of compounds which selectively modulate the bioactivity of only a subset of the HDx family.

Furthermore, inhibitors of the enzymatic activity of each of the subject HDx proteins can be identified using assays derived from measuring the ability of an agent to inhibit catalytic conversion of a substrate by the subject proteins. For example, the ability of the subject HDx proteins to deacetylate a histone substrate, such as histone H4, in the presence and absence of a candidate inhibitor, can be determined using standard enzymatic assays.

A number of methods have been employed in the art for assaying histone deacetylase activity, and can be incorporated in the drug screening assays of the present invention. In preferred embodiments, the assay will employ a labeled acetyl group linked to appropriate histone lysine residues as substrates, in other embodiments, a histone substrate peptide can be labeled with a group whose signal is dependent on the simultaneous presence or absence of an acetyl group, e.g., the label can be a fluorogenic group whose fluorescence is modulated (either quenched or potentiated) by the presence of the acetyl moiety. Using standard enzymatic analysis, the ability of a test agent to cause a statistically significant change in substrate conversion by a histone deacetylase can be measured, and as desirable, inhibition constants, e.g., $K_i$ values, can be calculated. The histone substrate can be provided as a purified or semi-purified polypeptide or as part of a cell lysate. Likewise, the histone deacetylase can be provided to the reaction mixture as a purified or semi-purified polypeptide or as a cell lysate. Accordingly, the reaction mixtures of the subject method can range from reconstituted protein mixtures derived with purified preparations of histones and deacetylases, to mixtures of cell lysates, e.g., by admixing baculovirus lysates containing recombinant histones and deacetylases.

In an exemplary embodiment, the histone substrate for the subject assay is provided by isolation of radiolabeled histones from metabolically labelled cells. To illustrate, as described by Hay et al. (1983) *J Biol Chem* 258:3726-3734, HeLa cells can be labelled in culture by addition of [$^3$H]acetate (New England Nuclear) to the culture media. The addition of butyrate, trapoxin or the like can be used to increase the abundance of acetylated histones in the cells. Radiolabelled histones can be isolated from the cells by extraction with $H_sSO_4$ (Marushige et al. (1966) *J Mol Biol* 15:160-174). Briefly, cells are homogenized in buffer, centrifuged to isolate a nuclear pellet, the subsequently homogenized nuclear pellet centrifuged through sucrose, and the resulting chromatin pellet extracted by addition of $H_sSO_4$ to yield [$^3$H]acetyl-labelled histones. In an alternate embodiment, nucleosome preparations containing [$^3$H]acetyl-labelled histones can be isolated from the labelled cells. As described in the art, nucleosomes can be isolated from cell preparations by sucrose gradient centrifugation (Hay et al. (1983) *J Biol Chem* 258:3726-3734; and Noll (1967) *Nature* 215:360-363), and polynucleosomes can be prepared by NaCl precipitation from micrococcal nuclease digested cells (Hay et al., supra). Similar procedures for isolating labelled histones from other cells types, including yeast, have been described. See, for example, Alonso et al. (1986) *Biochem Biophys Acta* 866: 161-169; and Kreiger et al. (1974) *J Biol Chem* 249:332-334. In yet other embodiments, the histone is generated by recombinant gene expression, and includes an exogenous tag (e.g., an HA epitope, a poly(his) sequence or the like) which facilitates in purification from cell extracts. In still other embodiments, whole nuclei can be isolated from metabolically labelled cells by micrococcal nuclease digestion (Hay et al., supra)

In still another embodiment, the deacetylase substrate can be provided as an acetylated peptide including a sequence corresponding to the sequence about the specific lysyl residues acetylated on histone, e.g., a peptidyl portions of the core histones H2A, H2B, H3 or H4. Such fragments can be produced by cleavage of acetylated histones derived from metabolically labelled cells, e.g., such as by treatment with proteolytic enzymes or cyanogen bromide (Kreiger et al., supra). In other embodiments, the acetylated peptide can be provided by standard solid phase synthesis using acetylated lysine residues (Kreiger et al., supra).

Continuing with the illustrative use of [$^3$H]acetyl-labelled histones, the activity of a histone deacetylase in the subject assays is detected by measuring release of [$^3$H]acetate by standard scintillant techniques. In a merely illustrative example, a reaction mixture is provided which comprises a recombinant HDx protein suspended in buffer, along with a sample of [$^3$H]acetyl-labelled histones and (optionally) a test compound. The reaction mixture is maintained at a desired temperature and pH, such as 22° C. at pH7.8, for several hours, and the reaction terminated by boiling or other form of denaturation. Released [$^3$H]acetate is extracted and counted. For example, the quenched reaction mixture can be acidified with concentrated HCl, and used to create a biphasic mixture with ethyl acetate. The resulting 2 phase system is thoroughly mixed, centrifuged, and the ethyl acetate phase collected and counted by standard scintillation methods. Other methods for detecting acetate release will be easily recognized by those skilled in the art.

In yet another embodiment, the drug screening assay is derived to include a whole cell recombinantly expressing one or more of a target protein or HDx protein. The ability of a test agent to alter the activity of the HDx protein can be detected by analysis of the recombinant cell. For example, agonists and antagonists of the HDx biological activity can by detected by scoring for alterations in growth or differentiation (phenotype) of the cell. General techniques for detecting each are well known, and will vary with respect to the source of the particular reagent cell utilized in any given assay.

For example, quantification of proliferation of cells in the presence and absence of a candidate agent can be measured with a number of techniques well known in the art, including simple measurement of population growth curves. For instance, where the assay involves proliferation in a liquid medium, turbidimetric techniques (i.e. absorbence/transmittance of light of a given wavelength through the sample) can be utilized. For example, in the instance where the reagent cell is a yeast cell, measurement of absorbence of light at a wavelength between 540 and 600 nm can provide a conveniently fast measure of cell growth. Likewise, ability to form colonies in solid medium (e.g. agar) can be used to readily score for proliferation. In other embodiments, an HDx substrate protein, such as a histone, can be provided as a fusion protein which permits the substrate to be isolated from cell lysates and the degree of acetylation detected. Each of these techniques are suitable for high through-put analysis necessary for rapid screening of large numbers of candidate agents.

In addition, where the ability of an agent to cause or reverse a transformed phenotype, growth in solid media such as agar can further aid in establishing whether a mammalian cell is transformed.

Additionally, visual inspection of the morphology of the reagent cell can be used to determine whether the biological activity of the targeted HDx protein has been affected by the added agent. To illustrate, the ability of an agent to influence an apoptotic phenotype which is mediated in some way by a recombinant HDx protein can be assessed by visual microscopy. Likewise, the formation of certain cellular structures as part of differentiation, such as the formation of neuritic process, can be visualized under a light microscope.

The nature of the effect of test agent on reagent cell can be assessed by measuring levels of expression of specific genes, e.g., by reverse transcription-PCR. Another method of scoring for effect on Hdx activity is by detecting cell-type specific marker expression through immunofluorescent staining. Many such markers are known in the art, and antibodies are readily available. For example, the presence of chondroitin sulphate proteoglycans as well as type-II collagen are correlated with cartilage production in chondrocytes, and each can be detected by immunostaining. Similarly, the human kidney differentiation antigen gp160, human aminopeptidase A, is a marker of kidney induction, and the cytoskeletal protein troponin I is a marker of heart induction. In yet another embodiment, the alteration of expression of a reporter gene construct provided in the reagent cell provides a means of detecting the effect on HDx activity. For example, reporter gene constructs derived using the transcriptional regulatory sequences, e.g. the promoters, for developmentally regulated genes can be used to drive the expression of a detectable marker, such as a luciferase gene. In an illustrative embodiment, the construct is derived using the promoter sequence from a gene expressed in a particular differentiative phenotype.

It is also deemed to be within the scope of this invention that the recombinant HDx cells of the present assay can be generated so as to comprise heterologous HDx proteins (i.e. cross-species expression). For example, HDx proteins from one species can be expressed in the cells of another under conditions wherein the heterologous protein is able to rescue loss-of-function mutations in the host cell. For example, the reagent cell can be a yeast cell in which a human MDx protein (e.g. exogenously expressed) is the intended target for development of an anti-proliferative agent. To illustrate, the M778 strain, MATa ura3-52 trp1□i his3-200 leu2-1 trk1□ rpd3:: HIS3, described by Vidal et al. (1991) *Mol Cell Biol* 6317-6327, which lacks a functional endogenous RPD3 gene can be transfected with an expression plasmid including a mammalian HDx gene in order to complement the RPD3 loss-of-function. For example, the coding sequence for HD4, HD5 or HD6 can be cloned into a pRS integrative plasmid containing a selectable marker (Sikorski et al. (1989) *Genetics* 122:19-27), and resulting construct used to transform the M778 strain. The resulting cells should produce a mammalian HDx protein which may be capable performing at least some of the functions of the yeast RPD3 protein. The HDx transformed yeast cells can be easier to manipulate than mammalian cells, and can provide access to certain assay formats, such as turbidity detection methods, which may not be obtainable with mammalian cells.

Moreover, the combination of the "mammalianized" strain with the strain M537 (MATa ura3-52 trp1☐i his3-200 leu2-1 trk1☐, Vidal et al., supra) can provide an exquisitely sensitive cell-based assay for detecting agent which specifically inhibit, for example, the yeast RPD3 deacetylase.

E. Small Molecule Combinatorial Libraries for HDx Inhibitors

The subject reactions readily lend themselves to the creation of combinatorial libraries of compounds for the screening of pharmaceutical, agrochemical or other biological or medically-related activity or material-related qualities. A combinatorial library for the purposes of the present invention is a mixture of chemically related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional methods.

Diversity in a library can be created at a variety of different levels. For instance, the substrate aryl groups used in a combinatorial approach can be diverse in terms of the core aryl moiety, e.g., a variegation in terms of the ring structure, and/or can be varied with respect to the other substituents.

A variety of techniques are available in the art for generating combinatorial libraries of small organic molecules. See, for example, Blondelle et al. (1995) *Trends Anal. Chem.* 14:83; the Affymax U.S. Pat. Nos. 5,359,115 and 5,362,899: the Ellman U.S. Pat. No. 5,288,514: the Still et al. PCT publication WO 94/08051; Chen et al. (1994) *JACS* 116: 2661: Kerr et al. (1993) *JACS* 115:252; PCT publications WO92/10092, WO93/09668 and WO91/07087; and the Lerner et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/08051, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay. Detailed descriptions of a number of combinatorial methodologies are provided below.

Direct Characterization

A growing trend in the field of combinatorial chemistry is to exploit the sensitivity of techniques such as mass spectrometry (MS), e.g., which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

Multipin Synthesis

The libraries of the subject method can take the multipin library format. Briefly, Geysen and co-workers (Geysen et al. (1984) PNAS 81:3998-4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also been appended to the pins so that the compounds may be cleaved from the supports after synthesis for assessment of purity and further evaluation (c.f., Bray et al. (1990) Tetrahedron Lett 31:5811-5814; Valerio et al. (1991) Anal Biochem 197:168-177; Bray et al. (1991) Tetrahedron Lett 32:6163-6166).

Divide-Couple-Recombine

In yet another embodiment, a variegated library of compounds can be provided on a set of beads utilizing the strategy of divide-couple-recombine (see, e.g., Houghten (1985) PNAS 82:5131-5135; and U.S. Pat. Nos. 4,631,211; 5,440, 016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) PNAS 82:5131-5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

Combinatorial Libraries by Light-Directed, Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) Annu Rep Med Chem 26:271-280; Fodor, S. P. A. (1991) Science 251:767; Pirrung et al. (1992) U.S. Pat. No. 5,143,854; Jacobs et al. (1994) Trends Biotechnol 12:19-26). The spatial resolution of photolithography affords miniaturization. This technique can be carried out through the use protection/deprotection reactions with photolabile protecting groups.

The key points of this technology are illustrated in Gallop et al. (1994) J Med Chem 37:1233-1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

Encoded Combinatorial Libraries

In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

Tagging with Sequenceable Bio-Oligomers

The principle of using oligonucleotides to encode combinatorial synthetic libraries was described in 1992 (Brenner et al. (1992) PNAS 89:5381-5383), and an example of such a library appeared the following year (Needles et al. (1993) PNAS 90:10700-10704). A combinatorial library of nominally $7^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In preferred embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr J M et al. (1993) J Am Chem Soc 115:2529-2531), orthogonality in synthesis is achieved by employing acid-labile protection for the coding strand and base-labile protection for the compound strand.

In an alternative approach (Nikolaiev et al. (1993) Pept Res 6:161-170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) Tetrahedron Lett 32:3891-3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

Non-Sequenceable Tagging: Binary Encoding

An alternative form of encoding the test compound library employs a set of non-sequenceable electrophoric tagging molecules that are used as a binary code (Ohlmeyer et al. (1993) *PNAS* 90:10922-10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) *J Org Chem* 59:4723-4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) *PNAS* 92:6027-6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

Examples

The invention, now being generally described, will be more readily understood by reference to the following examples, which are included merely for purposes of illustration of certain aspects and embodiments of the present invention and are not intended to limit the invention.

Experimental Results

A. Identification of Three Novel Class II human HDAC Enzymes

The NCBI database was screened with the yeast Hda1p amino acid sequence to identify human homologs. The complete ORFs of HDAC 4, 5, and 6 were constructed as described in Methods. HDAC4 consists of 1085 amino acids, with a putative catalytic region beginning at amino acid 802 (FIG. 1A). HDAC5 is highly homologous to HDAC4 (51% identity, 63% similarity), with 1123 amino acids and a catalytic region beginning at amino acid 832 (FIG. 1B). HDAC6 is the largest HDAC protein yet identified in humans, with 1216 amino acids. It is also unique in that it consists of an apparent internal dimer containing two catalytic domains, with the first beginning at amino acid 215 and the second at amino acid 610 (FIG. 1C). The two catalytic regions in HDAC6 are highly homologous to each other (47% identity, 64% similarity) and therefore the protein may have arisen evolutionarily from an in frame gene duplication event. All the catalytic domains of these three proteins are highly conserved with respect to each other and previously identified HDAC proteins (FIG. 1D). There are 15 invariant residues in this region between HDAC1, 4, 5, 6 proteins and Hda1p, and a total of 37 invariant residues within the four catalytic domains of the three new HDAC proteins. This level of sequence conservation strongly suggests that these novel proteins have deacetylase activity.

B. Differential Expression of Class II HDACs in Human Tissues

Figure 2A:
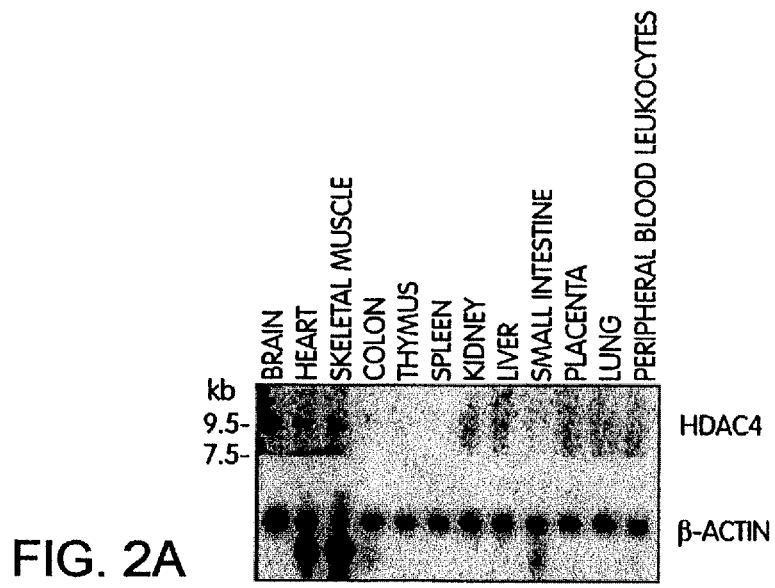
FIGS. 2A and 2B. Expression analysis of novel human Class II HDAC family members. Multiple human tissue northern blots were probed to determine mRNA expression of HDAC4, HDAC5, and HDAC6. Blots were stripped and reprobed with (β-actin cDNA to normalize for total mRNA. The position of molecular size markers is indicated to the left.
Figure 2B:
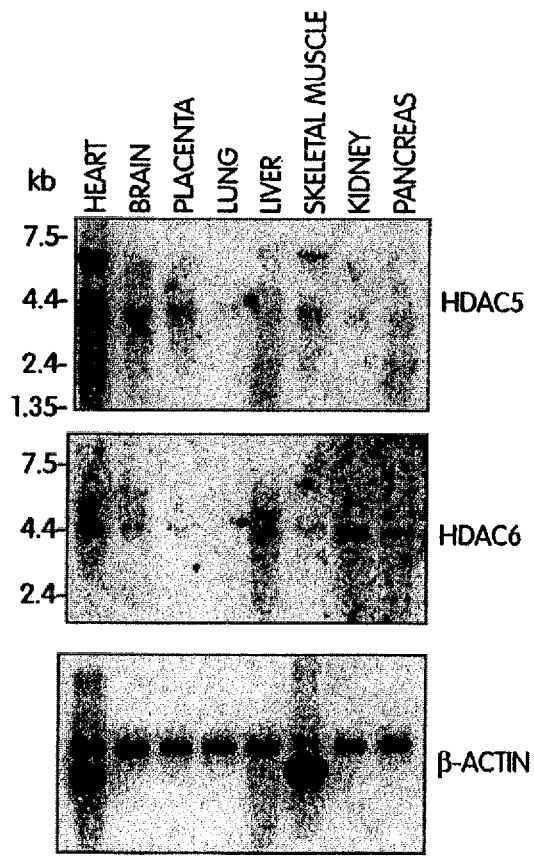

Northern blot analyses indicate differential tissue expression of the human class II HDACs (FIG. 2). HDAC4 is detectable as a 9.6 kb transcript in brain, heart and skeletal muscle tissues. The signal is very weak, however, which may have been caused by the fact that the transcript is at the upper size limit for mRNA samples in this particular blot. It is possible that HDAC4 is expressed in other tissues, but the quantity of transcript in these samples may be too low to detect. This finding is consistent with the small number of ESTs corresponding to this cDNA present in the database. HDAC5 expression partially overlaps that of HDAC4, and is observed primarily in brain, heart, skeletal muscle, and placental tissues as a 3.7 kb transcript. HDAC6, which is present as a 5 kb transcript, has the highest expression levels in heart, liver, kidney, and pancreas. The differences in tissue expression may reflect a tissue specific function of these enzymes.

C. In Vitro Histone Deacetylase Activity of Class II HDACs

Figure 3A:
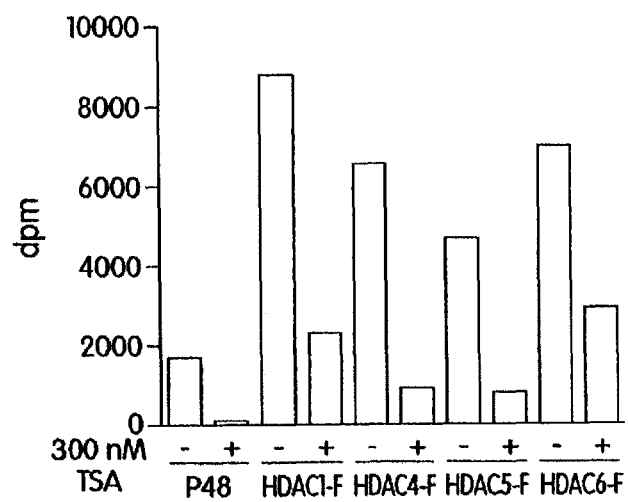
FIGS. 3A and 3B. Class II HDAC enzymes deacetylate all four core histones in vitro. Recombinant FLAG-tagged HDACs were immunoprecipitated from transfected Jurkat cell extracts using α-FLAG antibody (Sigma). Immunopurified enzymes were incubated with radiolabeled core histones as described in Methods. (A) The HDAC activity was measured by scintillation counting of the released [$^3$H]-acetic acid. Where indicated, immunoprecipitates were preincubated with trichostatin A (Wako) prior to addition of histones. Each assay was performed in duplicate and averaged. (B) Substrate specificity of class II HDACs. Deacetylase reactions were separated by 20% SDS/PAGE and stained with Coomassie (top). The gel was treated with EnHance (National Diagnostics), dried and exposed to film (bottom). The identities of the core histones are indicated to the left. RbAp48 was transfected as a negative control.

To determine if HDAC4, 5 and 6 possess histone deacetylase activity, the recombinant proteins were assayed for enzymatic activity in vitro. Epitope-tagged recombinant HDACs 1, 4, 5, and 6 were expressed in Tag-Jurkat cells and immunoprecipitated. The immunoprecipitates were incubated with $^3$H-acetate labeled histones, and the subsequent release of $^3$H-acetate was quantified by scintillation counting. All four HDAC enzymes exhibit deacetylation activity that is at least two-fold above background levels (FIG. 3A). In each case, activity is greatly reduced by the presence of 300 nM TSA, a potent HDAC inhibitor. HDAC1 and HDAC6 possess comparable activity, whereas that of HDAC4 and HDAC5 is somewhat reduced. This is most likely due to lower expression levels for these two recombinant proteins rather than inherently weaker histone deacetylase activity (see FIG. 5A). Furthermore, co-immunoprecipitation experiments (see FIG. 5*b*) demonstrate the association of HDAC4 and HDAC5 with HDAC3. It is possible that the observed HDAC activity is due to HDAC3. However, sequence analysis suggests that HDAC4 and HDAC5 possess functional catalytic domains, and therefore should contribute to the activity. Therefore, in vitro, all three human class II HDACs can deacetylate histones in a trichostatin-sensitive manner.

Figure 3B:
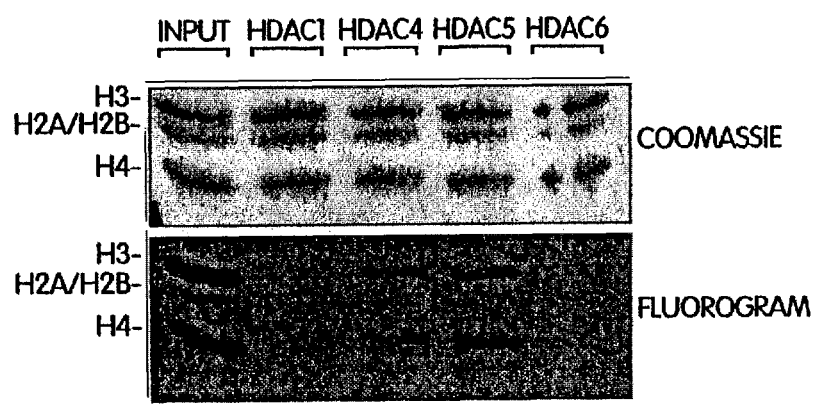

Previously, Hda1p was shown to preferentially deacetylate histone H3 in vitro (16). In order to determine if HDAC4, 5 and 6 display similar preferences, the immunopurified recombinant proteins were incubated with $^3$H-acetate labeled histones and the deacetylase reactions were separated by SDS/PAGE to identify the different histone isotypes. The gel was then exposed to autoradiography to determine the relative amount of acetylated histones remaining in each case. HDAC1, 4, 5, and 6 deacetylate all four core histories equally well, though again deacetylation by HDAC4 and HDAC5 is incomplete (FIG. 3B).

D. Independently Active Catalytic Domains of HDAC6

Figure 4A:
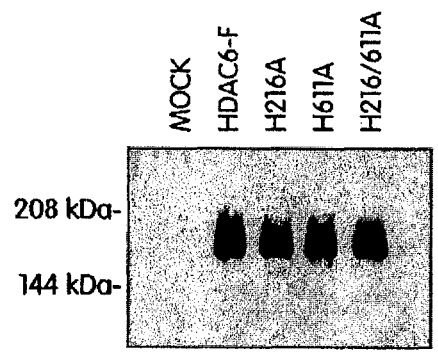
FIGS. 4A and 4B. The catalytic domains of HDACb function independently. The histidine residues homologous to H141 of HDAC1 in each of the catalytic domains (H216 and H611) were mutated to alanine by PCR overlap extension. The single and double mutants were FLAG-tagged and expressed in Tag-Jurkat cells. The enzymes were immunoprecipitated using α-FLAG antibodies (Sigma) and expression levels were compared by Western blotting (A). The mutant enzymes were then assayed for histone deacetylase activity as before (B).
Figure 4B:
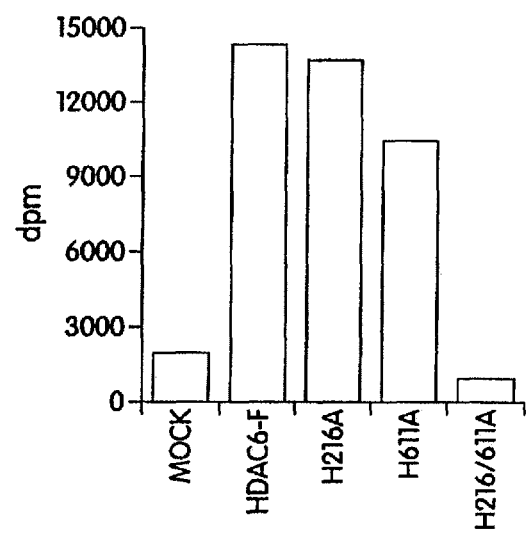

HDAC6 possesses two separate putative catalytic domains. Site-directed mutagenesis was performed in order to determine if either domain required the other for catalytic activity. Histidine 141 of HDAC1 was shown previously to be critical for deacetylase activity (18). The corresponding histidine residues in each catalytic domain of HDAC6 were mutated to alanine, to produce the H216A and H611A single mutants and the H216/611A double mutant. The mutant HDAC6 proteins were expressed and assayed for in vitro deacetylation of histones. Mutation of either H216 or H611 to alanine results in a slight reduction of histone deacetylase activity, and simultaneous mutation of both sites abrogates this activity completely (FIG. 4A, 4B). Furthermore, a truncation of HDAC6 containing the N-terminal 460 amino acids, and therefore only the first catalytic domain, is still catalytically active (data not shown). Therefore, both catalytic domains of HDAC6 are fully functional histone deacetylases and contribute independently to the overall activity of the wild-type HDAC6 protein.

E. Expression and Co-Immunoprecipitation of Class II HDACs

Figure 5A:
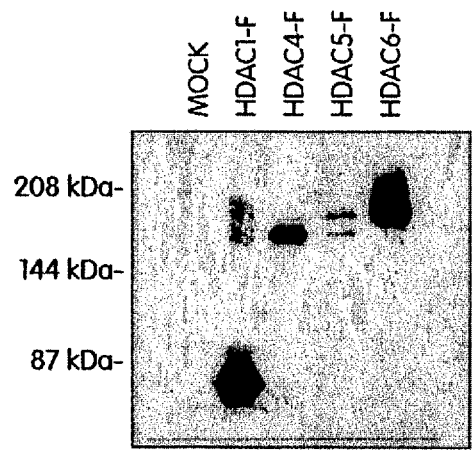
FIGS. 5A and 5B. Class II HDAC enzymes and HDAC1 are in different complexes in vivo. Recombinant FLAG-tagged HDACs were precipitated from transfected Jurkat cell extracts using α-FLAG antibody (Sigma), separated by SDS/PAGE and subjected to Western blot analysis. Blots were probed with (A) α-FLAG antibody (Sigma) to determine expression levels and (B) α-CHD4, α-mSin3A, α-MTA, α-HDAC1, αHDAC3 and α-Rbp48 antibodies to determine if these proteins co-immunoprecipitated with the Class II HDAC enzymes.

Recombinant, FLAG epitope-tagged proteins were subjected to Western blot analysis to address possible protein-protein interactions. HDAC1 migrates as a band slightly above its expected size of 55 kDa in SDS/PAGE (FIG. 5A). Recombinant HDAC4 and 6 appeared above their theoretical molecular weights of 119 kDa and 131 kDa, respectively. The expression level of HDAC5 is significantly lower than the others, and the protein appears as a doublet, both in the lysate (data not shown) and in the immunoprecipitate (FIG. 5A). This doublet may be the result of post-translational modifications or partial proteolytic degradation. The high molecular weight diffuse signal apparent in the blot is most likely due to cross-reaction of the secondary mouse antibody with contaminating FLAG antibody used for the immunoprecipitation. This signal is partially masked by the comigration of the recombinant HDAC4, 5 and 6 proteins.

Figure 5B:
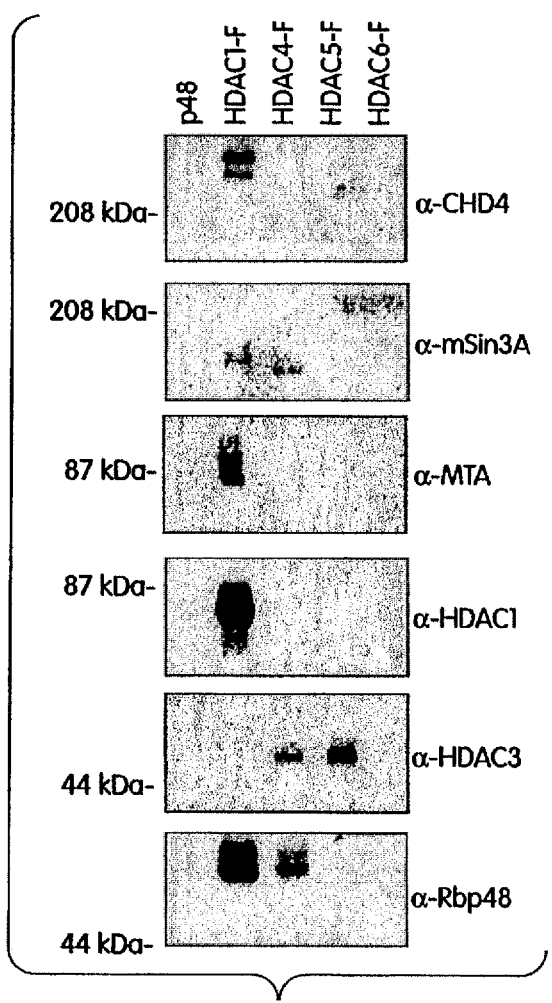
Figure 6B:
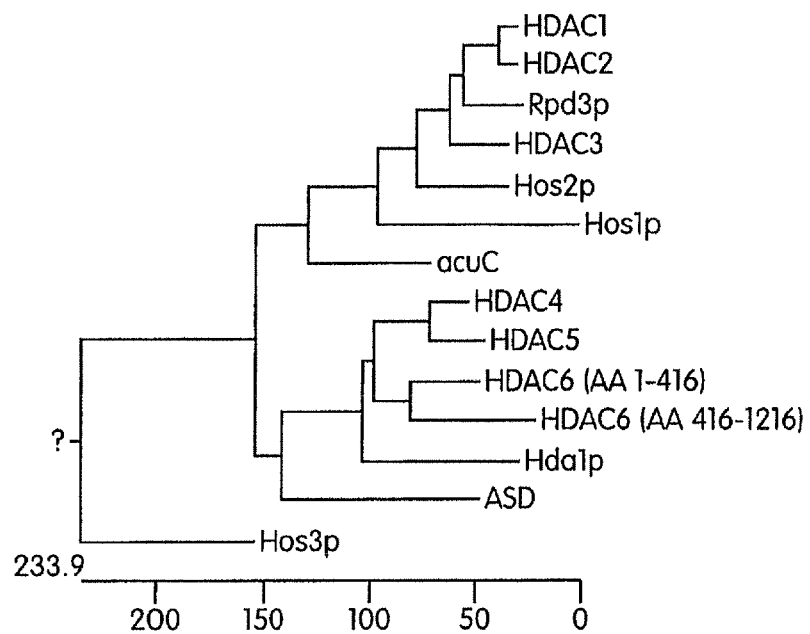

HDAC1 has been shown to be associated with a variety of transcription-related proteins, including the CHD chromodomain proteins, metastasis-associated factors (MTA), the co-repressor mSin3A and the histone-binding protein RbAp48. In order to determine if HDAC4, 5, and 6 associated with the same proteins in vivo, a series of co-immunoprecipitation experiments was performed. Immunoprecipitates were probed with □-CHD4, □-mSin3A, □-MTA, □-RbAp48, □-HDAC1, and □-HDAC3 antibodies (FIG. 5B). The HDAC1 sample contains bands corresponding to all proteins with the exception of HDAC3, as anticipated. There is a band in the mSin3A blot of the HDAC4 immunoprecipitate, which appears at a lower molecular weight than expected for mSin3A. The nature of this band is unclear, since it does not correspond to any of the previously observed forms of mSin3A. HDAC4 coimmunoprecipitates with Rbp48 and HDAC3, though none of the other proteins were apparent. HDAC5 associates only with HDAC3, though it is possible that the expression levels were too low to detect other associated factors. HDAC6 does not appear to interact with any of these proteins, despite robust expression, nor was HDAC1 or HDAC2 found to co-immunoprecipitate with the class II HDACs. This analysis suggests that these novel class II HDAC proteins are biochemically distinct from HDAC1 in vivo.

F. Immunoprecipitation of HDAC4 and HDAC5 Complexes

Figure 7A:
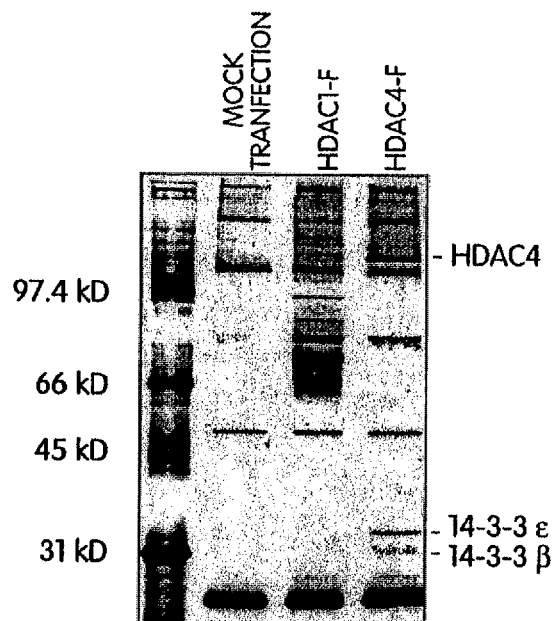
FIGS. 7A and 7B. Association of 11DAC4 and HDAC5 with two isoforms of 14-3-3.
Figure 7B:
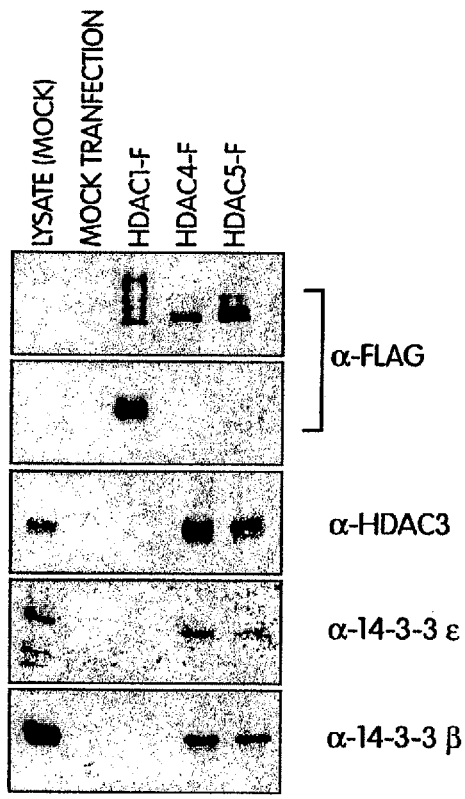

Recombinant, FLAG-epitope tagged HDAC1 and HDAC4 were transiently expressed in TAg Jurkat cells and immunoprecipitated with □-FLAG antibodies. The purified proteins were separated by SDS/PAGE and visualized by silver staining. Comparison with the mock-transfected negative control and the HDAC1 samples revealed the presence of specific 30- and 32-kDa protein bands in the HDAC4 immunoprecipitate. Peptides derived from these proteins were analyzed by peptide microsequencing and found to correspond to the □ and □ isoforms of 14-3-3, respectively (FIG. 7A). Duo to the high degree of sequence similarity between HDAC4 and HDAC5 (51% identity), it was hypothesized that HDAC5 associates with 14-3-3 proteins as well. The presence of these two 14-3-3 protein isoforms in both HDAC4 and HDAC5 immunoprecipitates was confirmed by Western blot analysis with isoform-specific antibodies (FIG. 7B). This analysis also confirmed the previously observed association of HDAC3 with both class II HDACs. These immunoprecipitation experiments suggest that HDAC4 and HDAC5 can associate, either directly or indirectly, both with HDAC3, which is nuclear (Emiliani et al., 1998), and 14-3-3 proteins, which are generally cytoplasmic (Burbelo and Hall, 1995).

G. Nuclear-Cytoplasmic Shuttling of HDAC4 and HDAC5 is Regulated by Binding to 14-3-3

We and other groups (Miska et al., 1999) have observed by immunofluorescence that HDAC4 and HDAC5 can be localized to either the cytoplasm or the nucleus, often aggregating in discrete foci (FIG. 8A). This nuclear and cytoplasmic localization is dynamic and shuttling can occur under normal conditions of cell growth. Recombinant HDAC4-EGFP was transiently expressed in COS-7 cells, and the localization of the protein was monitored over a period of three hours in live cells. While the localization of HDAC4-EGFP remained static in the majority of cells, shuttling was observed in some cases (data not shown). This nuclear-cytoplasmic shuttling process could explain the apparent discrepancy observed in the immunoprecipitation experiments, in which HDAC4 and HDAC5 were found to interact with both nuclear HDAC3 and cytoplasmic 14-3-3.

Several cases have been reported in which proteins are sequestered in the cytoplasm by binding to 14-3-3, and disruption of this interaction allows the proteins to translocate into the nucleus and perform their function (Brunet et al., 1999; Lopez-Girona et al., 1999; Wang et al., 1999; Yang et al., 1999). It is possible that binding of HDAC4 and HDAC5 to 14-3-3 sequesters these proteins in the cytoplasm, where they are presumably unable to repress transcription. Upon loss of 14-3-3 binding, HDAC4 and HDAC5 could translocate into the nucleus, bind to HDAC3 and MEF2, and repress MEF2-dependent gene expression. In order to study the effect of 14-3-3 binding on HDAC4 localization, HDAC4-EGFP and myc-tagged 14-3-3□ were co-expressed in U2OS cells, and the cellular localization of HDAC4 was analyzed by immunofluorescence in triplicate experiments (FIG. 8B). Expression of HDAC4-EGFP alone results in a cytoplasmic localization of HDAC4 in 67 (±3) % of the cells, while simultaneous overexpression of 14-3-3□ increases this to 97 (±1) % of the cells. This correlation suggests that 14-3-3 may play a role in sequestering HDAC4 in the cytoplasm.

H. Association of HDAC4 and HDAC5 with 14-3-3 and HDAC3

It is known that 14-3-3 proteins bind to phosphorylated serine or threonine residues in defined consensus sequences (Rittinger et al., 1999; Yaffe et al., 1997). It was hypothesized that phosphorylation of HDAC4 and HDAC5 would allow association with 14-3-3 and sequestration in the cytoplasm. Dephosphorylation of these HDACs should result in the loss of interaction with 14-3-3, with subsequent translocation to the nucleus and binding to HDAC3. To test this hypothesis, the effect of phosphorylation of HDAC4 and HDAC5 on their association with 14-3-3 and HDAC3 was analyzed.

Recombinant FLAG-tagged HDAC4 and HDAC5 were transiently expressed in TAg Jurkat cells that were subsequently treated with the general serine/threonine kinase inhibitor staurosporine or the PP1 and PP2A phosphatase inhibitor calyculin A. The recombinant proteins were immunoprecipitated and analyzed by western blot (FIG. 9A). Under dephosphorylating conditions due to staurosporine treatment, there is a decrease in binding of HDAC4 and HDAC5 to either 14-3-3 isoform, and a corresponding increase in HDAC3 association. In addition, an increase in the overall HDAC activity of the purified complex was observed (FIG. 9A). Similarly, under hyper-phosphorylating conditions due to calyculin A treatment, HDAC4 and HDAC5 undergo a notable electrophoretic mobility shift, probably due to direct phosphorylation. An increase in 14-3-3 binding is observed as well, with a concomitant loss of interaction with HDAC3. This loss of binding to HDAC3 presumably causes the dramatic reduction in immunoprecipitated HDAC activity that is observed, though the activity of isolated HDAC4 and HDAC5 is still above background. These data suggest that binding of 14-3-3 to HDAC4 and HDAC5 is dependent on the presence of phosphorylated serine or threonine residues, and corresponds to a loss of interaction with HDAC3 in the nucleus.

I. Binding of 14-3-3 to HDAC4 Blocks Binding of Importin □

14-3-3 proteins have been shown to sequester *Xenopus* Cdc25 in the cytoplasm by binding near a bipartite nuclear localization sequence and blocking its interaction with the importin □□ heterodimer (Yang et al., 1999), which is required for import into the nucleus (Gorlich, 1997). HDAC4 also contains a nuclear localization sequence (Hicks and Raikhel, 1995). In order to determine if the interaction with 14-3-3 blocks binding of the importin heterodimer, recombinant FLAG-tagged HDAC4 was immunoprecipitated from untreated, staurosporine-, and calyculin A-treated TAg-Jurkat cells and analyzed for binding to importin □ by Western blotting. Upon binding to 14-3-3 due to calyculin. A treatment, HDAC4 fails to associate with importin □ (FIG. 9B). Thus, sequestration of HDAC4 and HDAC5 in the cytoplasm by 14-3-3 may be caused by masking a nuclear localization sequence.

J. Mutations of the 14-3-3 Binding Sites Cause Increased Nuclear Localization of HDAC4

14-3-3 proteins bind to well-defined consensus sequences containing phosphorylated serine or threonine residues (Rittinger et al., 1999; Yaffe et al., 1997). There are four canonical 14-3-3 binding sites in HDAC4, three of which are well conserved in HDAC5. The serine residues in each of these three sites in HDAC4 (S246, S466, S632) were mutated to alanine in order to prohibit phosphorylation and thus prevent 14-3-3 binding. Mutation of individual sites or two sites is not sufficient to abrogate binding of 14-3-3, but mutation of all three serine residues to alanine (HDAC4 S246/466/632A) abolishes binding to 14-3-3□ and □, even under hyperphosphorylating conditions due to calyculin A treatment. Furthermore, localization of the triple mutant to the cytoplasm is dramatically decreased compared to the wild-type and single mutants, consistent with a role for 14-3-3 in sequestration of HDAC4 and HDAC5 in the cytoplasm.

K. Disruption of HDAC3 and HDAC4 Interaction Upon Calyculin A Treatment

Interestingly, despite its inability to bind 14-3-3 and its concomitant nuclear localization, the HDAC4 S246/466/632A triple mutant is still unable to bind to HDAC3 under calyculin A treatment. Hence, the inability of HDAC4 to associate with HDAC3 under hyperphosphorylating conditions cannot simply be due to its sequestration in the cytoplasm. Other possibilities include a change in HDAC4 conformation or electrostatic properties upon direct phosphorylation that prevents association with HDAC3, direct phosphorylation of HDAC3 resulting in similar alteration in its conformation or electrostatic nature, or modifications of additional factors that may be required for mediating the HDAC4-HDAC3 interaction.

In order to distinguish between these possibilities, immunoprecipitated HDAC4 from untreated, staurosporine-treated, or calyculin A-treated cells was incubated with lysates from untreated or calyculin A-treated TAg Jurkat cells. Briefly, forty-eight hours after transfection with HDAC4-FLAG, TAg Jurkat cells were treated with staurosporine or calyculin A for 1.5 hours. HDAC4-FLAG was immunopurified and the sample was split into thirds. One-third of the immunopurified protein was prepared for Western blot analysis, one-third was incubated for 1 hour with untreated TAg Jurkat lysate, and the remaining one-third of the sample was incubated with calyculin A-treated TAg Jurkat lysate for 1 hour. These samples were analyzed for 14-3-3 and HDAC3 binding by Western blot analysis. Untreated and staurosporine-treated (presumably hypophosphorylated) HDAC4 associated with HDAC3 under all conditions, which is consistent with previous observations. Notably, there is an increase in the amount of associated HDAC3 upon incubation with lysate from untreated cells, but not after incubation with lysate from cells treated with calyculin A. This suggests that HDAC3 from untreated cells, but not from calyculin A-treated cells, is still competent to bind HDAC4. Furthermore, there is no factor in calyculin A-treated cells that can disrupt the HDAC4-HDAC3 interaction once it has formed.

As previously observed, calyculin A-treated (hyperphosphorylated) HDAC4 does not bind to HDAC3 under normal immunoprecipitation conditions. However, upon incubation with untreated cell lysates, calyculin A-treated HDAC4 does pull down HDAC3. This interaction is not present upon incubation with calyculin A-treated lysate. Hence, calyculin A-treatment of HDAC4 does not cause it to undergo a conformational change that would prevent it from binding to HDAC3. Note that though there does seem to be a slight decrease in the amount of HDAC3 present in the calyculin A treated lysate, it is not significant enough to explain the complete lack of binding to HDAC4.

These experiments suggest that while sequestration of HDAC4 in the cytoplasm by 14-3-3 may serve to prevent its interaction with HDAC3, this association is abrogated by an additional mechanism when the cell is exposed to hyperphosphorylating conditions. Since calyculin A-treated HDAC4 still is capable of association with HDAC3, this loss of interaction instead may be due to the phosphorylation of HDAC3 or to the modification of additional proteins required for mediating the HDAC3-HDAC4 association.

L. Increased Nuclear Localization of HDAC4 Enhances MEF2-Dependent Repression

The sequestration of HDAC4 and HDAC5 in the cytoplasm by 14-3-3 presumably prevents these proteins from repressing gene transcription, and therefore represents a novel mechanism for controlling HDAC activity. In order to determine if cellular localization affects HDAC4-mediated transcriptional repression by MEF2, the following series of reporter gene assays was performed. TAg-Jurkat cells were transfected with a MEF2-luciferase reporter, the MEF2D transcription factor, and either wild-type HDAC4 or the HDAC4 S246/466/632A triple mutant, which no longer binds to 14-3-3 and displays enhanced nuclear localization. Equivalent expression levels of the wild-type and triple mutant HDAC4 recombinant proteins was confirmed by Western blot analysis (data not shown). Expression of wild-type HDAC4 decreases MEF2-dependent transcription slightly, while expression of the HDAC4 triple mutant completely represses transcription. These data are consistent with a model in which loss of association with 14-3-3 results in nuclear localization of HDAC4 and association with MEF2 and HDAC3, causing increased transcriptional repression.

M. Screening for Specific Inhibitors of Human HDACs

Three classes of histone deacetylase enzymes have been identified in mammalian cells Gray et al. (2001) Exp Cell Res 262:75-83). Class I and Class II HDACs are structurally very similar and possess a conserved catalytic domain of approximately 390 amino acids (Finnin et al. (1999) Nature 401: 188-93). Of these, four class I (HDAC1, 2, 3 and 8) and four class II (HDAC4, 5, 6, 7) have been identified in humans. A third class of seven human histone deacetylases with homology to yeast Sir2 has recently been characterized. These HDACs posses a very different primary sequence, and have a conserved catalytic domain of approximately 275 AA. Unlike the class I and class II HDACs, the Sir2 enzymes require NAD as a substrate for deacetylation. Furthermore, these enzymes are not affected by any known HDAC inhibitors. Thus, class I and II HDACs presumably function by the same mechanism, while the Sir2 HDACs evolved separately and function by a very different mechanism.

The class I and class II HDACs are found in several different protein complexes (rev in Ng and Bird (2000) TIBS 25: 121-6; Ahringer (2000) TIGS 16: 351-6) Kao et al (2000) Genes Dev 14: 55-66; Huang et al. (2000) Genes Dev 14: 45-54). With the exception of HDAC6, all of these HDACs are found in the nucleus (unpublished observations) and presumably function in deacetylating histones and silencing gene expression when recruited to chromosomal domains or promoters of specific genes. Several transcription factors, including nuclear hormone receptors (Xu et al. (1999) Curr Opin Genet Dev 9: 140-7) and methylated DNA-binding proteins (Ballestar and Wolffe (2001) Eur J Biochem 268: 1-6) have been shown to recruit specific HDAC complexes, but thus far it has not been possible to determine the complete set of gene targets for each of the HDACs in mammalian cells, since profiling of knockouts have not been reported. Thus, it would be highly advantageous to acquire a set of inhibitors that are specific for each of the known class I and class II HDACs. Analysis of the differences in the structures of the HDACs and previous reports of specificity of certain natural and synthetic HDAC inhibitors suggest that this is a feasible goal.

Structure of Class I and II HDACs

The crystal structure of a bacterial HDAC homolog, HDLP (histone-deacetylase like protein), has been reported (Finnin et al. (1999) Nature 401: 188-93). HDLP has a single domain structure related to the open α/β class of folds. It contains a central eight-stranded parallel β-sheet, with four α-helices packed on either face. Eight additional α-helices and large loops in the β-sheet further extend the structure, and result in the formation of a deep, narrow pocket, with an adjacent internal cavity. HDLP requires $Zn^{2+}$ for activity, and this zinc cation positioned near the bottom of the pocket, which thus presumably is the active site (see FIG. 10). The active site contains several aspartate and histidine residues, which appear to function in both coordinating the zinc ion and acting as a charge relay system to increase the nucleophilicity of a bound water molecule, thereby activating it to attack the amide bond of the acetyl-lysine (see FIG. 11). The channel leading to the active site is surrounded by hydrophobic residues, which is presumably where the aliphatic chain of the acetyl-lysine residue is nestled.

A small molecule inhibitor of histone deacetylases, trichostatin A, has been co-crystallized with HDLP and allows for an analysis of the structural properties of these inhibitors. TSA contains a cap group, and aliphatic chain and a terminal hydroxamic acid functional group (FIG. 12). The hydroxamic acid coordinates the zinc cation in a bidentate fashion and hydrogen bonds with some of the active site residues. The aliphatic chain fits snugly into the channel, making several van der Waals contacts with the channel residues. The cap group contacts residues on the rim of the pocket, and probably mimics the amino acids adjacent to the acetylated lysine residue in the histone. Binding of TSA causes a conformational change in a tyrosine residue on this rim (Tyr91), thereby allowing tighter packing of the cap group.

The proposed mechanism for the deacetylation reaction is similar to that seen in metallo- and serine proteases (see FIG. 11). The carbonyl oxygen of the N-acetyl amide bond is thought to coordinate to the zinc cation, thereby positioning it closely to a bound water molecule and activating it for a nucleophilic attack by the water. The nucleophilicity of the water molecule, in turn, is enhanced by an interaction with the negatively charged histidine-arginine pair. Attack of the water molecule on the carbonyl carbon produces an oxy-anion intermediate, which is presumably stabilized by interacting with the zinc ion, and possibly by hydrogen bonding to a nearby tyrosine. The collapse of this intermediate would result in the break of the carbon-nitrogen bond, with the nitrogen accepting a proton from the histidine residue, and thereby producing the observed acetate and lysine products.

Structural Differences of the Human HDACs

The catalytic domains of the eight known human HDACs is very well conserved, but there are certain differences that may allow for the production of specific inhibitors. Most of the residues seen in the HDLP structure that interact directly with TSA are completely conserved among all of the HDACs, but the conservation in the surrounding residues is less, with significant differences apparent between the class I and class II HDACs (FIG. 13). Notably, there is significant divergence in the region of Tyr91 of HDLP, and this tyrosine residue itself is very poorly conserved among the human HDACs. This is particularly striking in that this residue is positioned on the rim of the channel and interacts directly with the cap group of TSA, and it is the only residue that shifts its conformation upon TSA binding. Thus, the considerable diversity in the region of the protein interacting with the cap group of the inhibitors suggests that it will be possible to develop specific inhibitors by altering the structure of this cap group.

Synthetic HDAC Inhibitors

Several non-natural inhibitors of histone deacetylases have been synthesized, and analysis of these will facilitate the rational design of novel and specific inhibitors. The basic structure of these small molecules mimics that of TSA, in that they possess a cap group, an aliphatic chain, and a functional group that would interact with the active site. It appears that the optimal length for the aliphatic chain is five to six carbon residues, with inhibitory activity decreasing rapidly for longer and shorter chains (Jung et al. (1999) J Med Chem 42: 4669-79) There are several possible functional groups, including epoxides, which appear to form irreversible covalent bonds with active site residues (see Furumai et al. (2001) Proc Natl Acad Sci USA 98: 87-92) as well as hydroxamic acid (Jung et al (1999) J Med Chem 42: 4669-79; Furumai (2001) Proc Natl Acad Sci USA 98: 87-92; Richon et al. (1996) Proc Natl Acad Sci USA 93: 57605-8; and Richon et al. (1998) 95: 3003-7) and o-aminoanilines (Suzuki et al. (1999) J Med Chem 42: 3001-3) which presumably coordinate the zinc cation. Two types of cap groups are found in natural HDAC inhibitors, a small flat or linear group or a cyclic tetrapeptide. Interestingly, the type of cap group alters the affinity with which the inhibitor binds to the active site. Molecules with a small cap are not active if the functional group is a carboxylic acid, while molecules with cyclic tetrapeptide cap groups and a carboxylic acid functional group are potent inhibitors.

Generation of Specificity

Alterations in the structure of the cap group has led to specific inhibitors of HDACs in two cases. First, N-alkylations of the indole residue in the cap group of apicidin has led to the development of apicidin derivatives that are ~20-fold more potent inhibitors of malarial HDACs than human HDAC1 (Meinke et al. (2000) J Med Chem 43: 4919-22). Secondly, HDAC6 is not inhibited by any of the cyclic tetrapeptide inhibitors, even when a hydroxamic acid is used as a functional group. Notably, HDAC6 has the greatest divergence from the other HDACs in the rim region surrounding Tyr91 in HDLP.

Design of Screen

Combinatorial libraries will be screened for specific inhibitors of HDACs 1, 4 and 6. HDAC1 was chosen to be the representative of the class I HDACs, while HDAC4 is the representative for the class II HDACs. HDAC6 will be screened because it is structurally divergent from the other class II HDACs, both in primary sequence in the catalytic domain, and the fact that it has two catalytic domains. Furthermore, HDAC6 is clearly divergent from the other HDACs in that it is not inhibited by the cyclic tetrapeptide class of inhibitors.

Thus far, an unbiased library (Sternson et al. (2001) J Am Chem Soc 123: 1740-7) has been screened for specific inhibitors of these three HDACs. In the future, libraries structurally biased to be similar to known HDAC inhibitors will be generated. In these cases, an aliphatic chain with a terminal function group, either a hydroxamic acid, carboxylic acid or an o-aminoaniline, will be attached to a structurally diverse core molecule. Thus, the diversity will be localized primarily to the cap group of these potential inhibitors, which is desirable in that changes in this region have been shown to lead to specificity.

Recombinant, purified FLAG-epitope tagged HDAC1 and HDAC6, as well as the catalytic domain of HDAC4(632-1070) fused to GST were incorporated in baculovirus vectors and expressed in Sf9 cells. Expression by baculovirus rather than expression in mammalian cells allowed for the isolation of larger quantities of protein, and also permitted the isolation of these HDACs without associated mammalian proteins. These proteins were labeled with Cy5 dye and used to screen a 1200 member library that had been printed on glass slides (MacBeath et al. (1999) J Am chem Soc 96: 4868-73). The molecules that were identified as reproducibly binding to any of the three HDACs were then tested in a secondary HDAC activity assay (Taunton et al. (1996) Science 272: 408-11) None of the identified hits were able to significantly inhibit HDAC activity at 100

Material and Methods

Construction of Baculoviruses cDNA encoding HDAC1 with a C-terminal FLAG epitope tag was cloned into the transfer vector pVL1392 (Pharmingen) and used to produce recombinant baculovirus as described previously (Hassig et al. (1997) Cell 89: 341-7). cDNA encoding HDAC6 with a C-terminal FLAG epitope tag was cloned into the NotI/XbaI site of pcDNA6-V5-HisA vector (Invitrogen). This construct, with the C-terminal FLAG, V5, and HisA tags was subcloned into the NotI/PmeI sites of pVL1392. This construct was used to generate recombinant baculovirus using the Baculogold DNA, according to the manufacturer's instructions (Pharmingen). HDAC4 recombinant baculovirus was constructed in the pAcSG2T vector, and was obtained from the Pavletich group (Memorial Sloan-Kettering Cancer Research Center, New York City). cDNA encoding residues 632 to 1070 of HDAC4 was inserted into the BamHI and EcoRI sites, in frame with the N-terminal GST coding sequence, separated by a thrombin cut site.

Expression of Protein in Sf9 Cells

Baculovirus was amplified to a concentration of ~1×10$^6$ pfu/ml. Sf9 cells were infected at a concentration of 1×10$^6$ cells/ml, with a multiplicity of infection of 2, at the National Cell Culture Center (Minneapolis, Minn.). 72 hours post-infection, cells infected with HDAC1 and HDAC6 baculovirus were pelleted, washed twice in PBS and flash frozen. In the case of the HDAC4 baculovirus, the protein is secreted into the media, and thus the cells were pelleted and the media saved and stored at 4° C.

Purification of Protein

In the case of GST-HDAC4(632-1070), the protein is secreted into the media. 500 µl of glutathione-agarose beads were washed in PBS and incubated with 500 mL of media, with shaking for 1.5 hours. The beads were pelleted (1000 rpm, 5') and washed twice with cold PBS. The protein was eluted with 10 mM glutathione in JLB (50 mM Tris-HCL, pH 8/150 mM NaCl/10% glycerol/0.5% TritonX-100). The beads were incubated twice with 1 mL of glutathione/JLB for 20 minutes, and once with 0.5 mL for 10 minutes. The collected eluant was dialyzed to remove the glutathione in a 10 kD MWCO Slide-A-Lyzer (Pierce) overnight against 1 L of PBS/10% glycerol/2.5 mM DTT. Note it was necessary to use a buffer without free amines in order to be compatible with the subsequent Cy5-labeling procedure.

Pellets of 250 and 100 mL of Sf9 cells infected with HDAC1 and HDAC6 baculovirus were lysed in 10 mL of JLB, with incubation at 4 C for 20 minutes. The lysate was clarified by pelleting the cellular debris at 14,000 rpm for 15 minutes. The protein was immunoprecipitated by incubating with 100 µl of anti-FLAG M2 agarose (Sigma). The beads were washed three times for three minutes in cold MSWB (50 mM Tris-HCL, pH 8/150 mM NaCl/1 mM EDTA/0.1% Nonidet P-40) and the protein was eluted by incubating the beads in 500 µL JLB with 1 mg of FLAG peptide for four hours. The eluant was collected and the beads washed with 200 µl JLB, which was added to the eluant. The protein was dialyzed overnight against JLB in a 10 kD MWCO Slide-A-Lyzer (Pierce). Since this buffer contains amines, it was necessary to exchange the JLB with PBS/10% glycerol/2.5 mM DTT, using a 10 kD MWCO Microcon (Millipore, Bedford, Mass.), according to the manufacturer's instructions.

Expression and Immunoprecipitation of HDACs from Mammalian Cells

Constructs containing HDAC 1 and HDAC6 with C-terminal FLAG epitope tags in the pBJ5 mammalian expression vector have been described (Grozinger et al. (1999) 96: 4863-73). These were transfected into TAg Jurkat cells by electroporation, and forty-eight hours later cells were lysed in JLB (50 mM Tris HCl pH 8/150 mM NaCl/10% glycerol/0.5% TritonX-100) containing a complete protease inhibitor cocktail (Boehringer-Mannheim). Lysis proceeded for 10 minutes at 4° C., after which the cellular debris was pelleted by centrifugation at 14K for 5 minutes. Recombinant proteins were immunoprecipitated from the supernatant by incubation with α-FLAG M2 agarose affinity gel (Sigma) for 1 hours at 4° C. For enzyme activity assays, the beads were washed three times with JLB at 4° C.

HDAC Assays.

$^3$H-acetate-incorporated histones were isolated from butyrate-treated HeLa cells by hydroxyapatite chromatography as described (Tong et al. (1998) Nature 395: 917-21). Immunoprecipitates were incubated with 1.4 μg (10,000 dpm) histones for three hours at 37° C. HDAC activity was determined by scintillation counting of the ethyl-acetate soluble $^3$H acetic acid (Taunton et al. (1996) Science 272: 408-11).

Cy5-Labeling of Proteins 1 mg of Cy5 monofunctional reactive dye (Amersham) was resuspended in 1 mL of 50 mM NaCO$_3$, pH 8.5. Protein was added to this to a concentration of ~1 mg/mL, and the reaction was incubated for 1.5 hours at 4° C. The solution was dialyzed in a 10 kD MWCO Slide-A-Lyzer (Pierce) against 1 L of PBS/10% glycerol/2.5 mM DTT overnight, and then against 2 L of PBS/10% glycerol/2.5 mM DTT/1 mM EDTA for five hours.

Screening of Slides

The 1,3 dioxane library (Sternson et al. (2001) J Am Chem Soc 123: 1740-7) was printed on glass slides as described previously. The slides were blocked for five hours in 3% BSA in PBST (0.1% Tween-20/PBS) and washed in PBST. Solutions of 400 nM of Cy5-labeled in 1% BSA/PBST were then added and incubated at 4 C for 1 hour. The slides were washed three times with PBST, rinsed with ddH$_2$O and spun dry (800 rpm, 30 seconds). The slides were scanned on a Applied Precision ArrayWorx scanner.

Results

Expression and Activity of Recombinant HDACs

HDAC1-F, GST-HDAC4(632-1070), and HDAC6-F-V5-HisA were expressed in Sf9 cells and purified by FLAG-agarose beads or glutathione agarose. These proteins were then labeled with Cy5 dye and purified from the free dye by dialysis. The purified proteins were subjected to SDS-PAGE and visualized by silver stain or western blotting with α-FLAG antibody. All of the proteins expressed well, and there were no contaminants at stoichiometric concentrations apparent from the silver stain, and thus these are anticipated to be relatively pure. Note that expression in Sf9 cells allows for the purification of these proteins in the absence of the associated mammalian proteins. This is critical for the identification of specific HDAC inhibitors, since HDAC1 usually associates with HDAC2 in most mammalian cell lines, while HDAC4 associates with HDAC3.

Screening on Printed 1,3 Dioxane Library with Recombinant HDACs

Approximately 2000 compounds from the 1,3 dioxane library were printed on slides (MacBeath et al. (1999) J Am Chem Soc 96: 4868-73) and screened with the three Cy5-labeled HDACs in triplicate. Compounds that reproducibly bound these HDACs were identified and their location in the arrayed plates was determined. An example of the observed results for an HDAC6-Cy5 screen (compound 4-P9) is shown in FIG. 15. The following compounds were identified in this assay:

HDAC1/HDAC6 common hits: 2-N20, 4-J18, 7-B2, 7-M1, 11-A15
HDAC1 unique hits: 4-H12
HDAC6 unique hits: 2-M7, 4-M9, 4-P9
Retest hits on HDAC1 and HDAC6

FLAG-tagged HDAC1 and HDAC6 were expressed in TAg Jurkat cells and purified by immunoprecipitation using the anti-FLAG antibody. Note that TAg Jurkat cells have undetectable quantities of soluble HDAC2, and therefore HDAC1 that is purified from these cells does not contain associated HDAC2. The proteins were used in in vitro HDAC assays with the compounds identified in the screen, using concentration of approximately 50 μM.

HDAC6 appeared to be inhibited by compound 11-A15, while HDAC1 was unaffected by it (see FIG. 16). Thus this compound was resynthesized and retested at 100 μM concentration, in triplicate (see results, FIG. 17). It did not inhibit either HDAC at this concentration. Retesting of other compounds also demonstrated that the previously observed inhibition was not reproducible. This suggests that the original results were due to the low signal-to-noise ratio.

Conclusions

In this screen, three different HDACs were chosen to represent the eight known human HDAC proteins. Based on sequence similarities, HDAC1 is highly related to HDACs 2 and 3, while HDAC4 is closely related to HDAC5 and 7. HDAC6 is has unique features, both in its sequence and in the fact that it is not inhibited by the cyclic tetrapeptide class of HDAC inhibitors.

The methodology outlined above will allow for rapidly screening several thousand printed compounds for specific binding to any of these three proteins. Positives identified in this binding assay can easily be tested in in vitro HDAC assays with the purified proteins to screen for specific inhibitory activity. Furthermore, this activity assay can be performed in very small volumes, and thus resynthesis of the positive compounds will not be required for this secondary screen.

None of the compounds identified in the binding assay tested positively in the subsequent activity assay. This suggests that these compounds were either false positives or did not bind to the active site of the enzymes. This is not particularly unexpected, since the library that was tested was not structurally biased to mimic HDAC inhibitors. Future libraries will include moieties containing an aliphatic side chain terminating with a hydroxamic acid, carboxylic acid, or o-amino anilide group. Sample compounds from these libraries have been shown to inhibit HDAC1 activity with an IC$_{50}$ of 5-100 μM, and thus these will probably be more suitable for these screens.

Experimental Methods

A. Cloning of HDAC4, HDAC5 and HDAC6

The amino acid sequence of yeast Hda1p was used in a tblastn search of the NCBI databases to identify human homologs of Hda1p. A cDNA clone for HDAC4 was obtained from the Kazusa DNA Research Institute, Kisarazu, Japan (Gene name KIAA0288, GenBank Accession Number 3024889). The full length clone was 8459 bp, with a predicted ORF of 2903 bp. A comparison of the HDAC4 clone with the HDAC5 sequence, however, revealed that the putative 5'UTR of HDAC4 was highly homologous to the N-terminal coding sequence of HDAC5. A truncation in the HDAC4 ORF seems to have been caused by a C to T point mutation in the putative 5'UTR of the HDAC4 clone, resulting in the conversion of a glutamate codon to a stop codon. This hypothesis was confirmed by obtaining the remaining N-terminal 352 bp by PCR from a 5'Stretch cDNA Leukemia Library (Clontech) and sequencing the product. A C-terminal FLAG epitope tag was incorporated into the complete HDAC4 ORF of 3255 bp, which was then inserted into the Not I-Eco RI sites of a mammalian expression vector (pBJ5).

An EST (GenBank Accession #R64669) homologous to yHda1p was identified and obtained from the I.M.A.G.E. Consortium (Lawrence Livermore National Laboratory). This sequence was used to generate a random primed probe (Boehringer Mannheim) to screen a Lambda ZAP II Jurkat cDNA library (Stratagene). A 2.3 kb cDNA clone was identified that contained a partial ORF of HDAC5. A blastn search of the NCBI database facilitated the assembly of the full-length cDNA sequence as a combination of a second clone from the Kazusa DNA Research Institute (Gene Name KIAA0600, GenBank Accession #3043724) and the cDNA clones containing the 11-js mRNA sequence (GenBank Accession # AF039241), kindly provided by Jeff Swensen, (University of Utah). An ORF of 3369 bp was identified and assembled into a C-terminal FLAG construct by subcloning into the Not I-Xho I sites of a pBJ5 vector.

A second EST homologous to yHDA1p was identified and used to screen the Lambda ZAP II Jurkat cDNA library. The sequence of the 2.5 kb clone produced was used in a blastn search to reveal the full length sequence of HDAC6 in the jm-21 mRNA sequence (GenBank Accession #AJ011972). This information was used to obtain the remaining 1.5 kb by nested PCR from a 0957 cDNA library, kindly provided by Don Ayer (University of Utah) to produce the full length ORF of 3648 bp. A C-terminal FLAG epitope tag was incorporated into this clone, which was inserted into the Not I-Spe I sites of pBJ5.

B. Northern Blot Analysis

Multiple human tissue Northern blots were obtained from Clontech. Probes were generated and blots were stripped using Strip-EZ DNA probe synthesis and removal kit (Ambion). Prehybridization and hybridization was carried out according to manufacturer's instructions using ExpressHyb solution (Clontech). For HDAC4 expression analysis, a 12-lane tissue blot was probed with the 895 bp SalI-SacI fragment of the HDAC4 gene. For HDAC5 expression analysis, an 8-lane tissue blot was probed with the 993 bp SacI-SacII fragment of the HDAC5 gene. This blot was stripped and reprobed for HDAC6 expression using the 667 bp SphI-AvrII fragment of the HDAC6 gene. Blots were stripped and reprobed with □-actin cDNA as a control (Clontech).

C. Antibodies, Immunoprecipitation and Western Blotting

Antibodies against HDAC1 (11), HDAC3 (17) and RbAp48 (17) have been described previously. Antibodies against mSin3A were kindly provided by Don Ayer (18), antibodies to the PHD domain of CHD4 were provided by Weidong Wang (National Institute on Aging/NIH) (6) and antibodies to the N-terminal domain of MTA were provided by Yasushi Toh (Kyushi University, Fukuoka, Japan) (19, 20).

Forty-eight hours after transfection, cells were lysed in JLB (50 mM Tris HCl pH 8/150 mM NaCl/10% glycerol/ 0.5% TritonX-100) containing a complete protease inhibitor cocktail (Boehringer-Mannheim). Lysis proceeded for 10 minutes at 4° C., after which the cellular debris was pelleted by centrifugation at 14K for 5 minutes. Recombinant proteins were immunoprecipitated from the supernatant by incubation with □-FLAG M2 agarose affinity gel (Sigma) for 2 hours at 4° C. For Western blot analysis, the beads were washed three times for 5 minutes at room temperature with MSWB (50 mM Tris HCl pH 8/150 mM NaCl/1 mM EDTA/0.1% NP-40) and the proteins were separated by SDS/PAGE. For enzyme activity assays, the beads were washed three times with JLB at 4° C.

D. HDAC Assays $^3$H-acetate-incorporated histones were isolated from butyrate-treated HeLa cells by hydroxyapatite chromatography as described (4). Immunoprecipitates were incubated with 1.4 µg (10,000 dpm) histones for three hours at 37° C. HDAC activity was determined by scintillation counting of the ethyl-acetate soluble $^3$H acetic acid (11). Inhibition of enzyme activity by trichostatin (TSA) was performed by incubating samples with 300 nM TSA (Wako) for 10 minutes prior to addition of the labeled histones.

E. Histone Isolation and Substrate Specificity Determination

For deacetylase assays, 6 □g of histones were incubated with immunoprecipitated recombinant enzyme or negative control (RbAp48 transfected) for 3 hours at 37° C. in HD buffer (50 mM Tris, pH 8.0/150 mM NaCl/10% glycerol). Reactions were stopped with SDS loading buffer and proteins were separated by 20% SDS/PAGE.

F. HDAC6 Mutagenesis

The H216A and H611A mutations were produced by PCR overlap extension. For each mutant, internal primers to both strands with the corresponding CAC to GCC mismatches were synthesized and used to amplify two overlapping fragments containing the mutation in the common region. These fragments were then used as templates in a second PCR reaction with the same flanking external primers. The H216A fragment was ligated into the Not I and Dra III sites of the wild-type HDAC6-pBJ5 construct. The H611A fragment was ligated into the Dra III and BstE II sites of the wild-type HDAC6-pBJ5. The H216/611A double mutant was constructed by ligating the H216A fragment into the Not I and Dra III sites of the HDAC6-H611A-pBJ5 clone. Plasmids were sequenced to ensure the incorporation of the mutations.

G. Cell Culture and Transfections

TAg-Jurkat cells were transfected by electroporation with 5 µg of FLAG-epitope tagged pBJ5 constructs for expression of recombinant proteins. Cells were mock-transfected without DNA or with an untagged RbAp48 construct in pBJ5 as a negative control. Cells were harvested 48 hours post-transfection.

H. DNA Constructs

FLAG-epitope-tagged HDAC4 and HDAC5 constructs in the pBJ5 mammalian expression vector have been described previously (Grozinger et al, 1999). The HDAC4-EGFP clone in pBJ5 was made by ligation of a Not I-Xba I HDAC4-FLAG fragment to a Xba I-Sal I EGFP fragment, which was generated by PCR from a plasmid containing EGFP (Clontech). The HDAC5-EGFP/pBJ5 construct was made similarly using Not I-Xba I HDAC5-FLAG fragment. The C-terminally-myc-epitope-tagged 14-3-3□ was produced by PCR from a Jurkat cDNA library (Stratagene) and subcloned into the Not I and Spe I sites of pBJ5.

The S246A, S466A and S632A single, double and triple mutations in HDAC4 were generated by PCR overlap extension. For each mutant, internal primers to each complementary strand with the corresponding base pair mismatches were synthesized and used to amplify two overlapping fragments containing the mutations in the common region. These fragments were then used in a second PCR with the same flanking external primers. The sequence of the primers used will be made available on request. The fragments were cloned into the Not I and Sac II sites of the HDAC4-F/pBJ5 construct and sequenced to ensure proper incorporation of the mutations.

The reporter used in the luciferase assays contains three copies of the desmin MEF2 site in pGL2-E1b-Luciferase and was generously provided by Eric Olson (University of Texas, Southwestern Medical Center). The myc-epitope-tagged. MEF2D/pSCT mammalian expression plasmid was kindly provided by Jun Liu (MIT).

I. Antibodies, Immunoprecipitation and Western Blotting

Antibodies against HDAC3 have been described previously (Hassig et al., 1998). Isoform-specific antibodies against 14-3-3□ and □ were obtained from Santa Cruz Biotechnology, while antibodies to importin □0 (□-Rch1) were acquired from Transducin Laboratories. □-FLAG M2 antibodies and □-mouse IgG Texas-red conjugated secondary antibodies for immunofluorescence were obtained from Sigma, while □-c-myc antibodies were purchased from Upstate Biotechnology.

Forty-eight hours after transfection, cells were lysed in JLB (50 mM Tris HCl pH 8/150 mM NaCl/10% glycerol/ 0.5% TritonX-100) containing a complete protease inhibitor cocktail (Boehringer-Mannheim) and phosphatase inhibitors (20 mM $NaH_2(PO_4)$, pH 7.2; 25 mM NaF, 2 mM EDTA). Lysis proceeded for 10 minutes at 4° C., after which the cellular debris was pelleted by centrifugation at 14K for 5 minutes. Recombinant proteins were immunoprecipitated from the supernatant by incubation with □-FLAG M2 agarose affinity gel (Sigma) for 1 hour at 4° C. For Western blot analysis and silver staining, the beads were washed three times for 5 minutes at room temperature with MSWB (50 mM Tris HCl pH 8/150 mM NaCl/1 mM EDTA/0.1% NP-40) and the proteins were separated by SDS/PAGE. For enzyme activity assays, the beads were washed three times with JLB at 4° C.

J. Peptide Microsequencing

The sequence analysis was performed at the Harvard Microchemistry Facility by microcapillary reverse-phase HPLC nano-electrospray tandem mass spectrometry (□LC/MS/MS) on a Finnigan LCQ quadropole ion trap mass spectrometer, K. HDAC Assays

[$^3$H]-acetate-incorporated histones were isolated from butyrate-treated HeLa cells by hydroxyapatite chromatography as described (Tong et al., 1998). Immunoprecipitates were incubated with 1.4 μg (10,000 dpm) histones for two hours at 37° C. HDAC activity was determined by scintillation counting of the ethyl-acetate soluble [$^3$H]acetic acid (Taunton et al., 1996).

L. Cell Culture and Transfections

TAg-Jurkat cells were transfected by electroporation with 5 μg of DNA for expression of recombinant proteins, or mock-transfected without DNA as a negative control. Cells were harvested 48 hours post-transfection. When required, cells were treated with 200 □M staurosporin (Calbiochem) or 20 nM calyculin A (Calbiochem) for 1.5 hours prior to harvesting.

M. Immunofluorescence

Cos-7 or U20S cells were plated on coverslips and allowed to attach overnight. Subsequently they were transfected with 1-2 □g of DNA using the Lipofectamine PLUS system (Gibco). Forty-eight hours later, cells were fixed with paraformaldehyde and stained with antibodies and Hoechst dye (Molecular Probes), or live cells were stained with Hoechst and the EGFP was visualized directly using an fluorescence microscope (Spencer Scientific Corporation). For the time course studies, a Delta Vision confocal microscope (Applied Precision Technologies) was used.

N. Reporter Gene Assays

For each sample, 10 million TAg Jurkat cells were transfected with a total of 5 □g of DNA. A constitutive □-galactosidase expression vector was used as a control for protein expression levels in the luciferase assays. Thirty-eight hours after transfection, the samples were harvested and split into sets of three. Luciferase activity was determined according manufacturer's instructions (Promega), and □-galactosidase activity was determined using a standard □-galactosidase assay. Luciferase values (relative light units) were normalized for transfection efficiency by dividing by □-gal activity. These assays were performed four times with similar results.

EQUIVALENTS

Those skilled in the art will recognize, or be able to ascertain using no more than routine experimentation, numerous equivalents to the specific polypeptides, nucleic acids, methods, assays and reagents described herein. Such equivalents are considered to be within the scope of this invention and are covered by the following claims.

We claim:

1. A polypeptide comprising an amino acid sequence identical to SEQ ID NO: 4 fused to a heterologous polypeptide and/or fused to an epitope tag.

2. The polypeptide of claim 1, wherein the polypeptide has deacetylase activity.

3. The polypeptide of claim 1, wherein the polypeptide binds to a histone, a 14-3-3 protein, a MEF2 transcription factor, or a retinoblastoma associated protein.

4. The polypeptide of claim 3, wherein the retinoblastoma associated protein is RbAp48.

5. The polypeptide of claim 1, wherein the heterologous polypeptide comprises glutathione-S-transferase.

6. The polypeptide of claim 1, wherein the heterologous polypeptide comprises a fluorescent protein.

7. The polypeptide of claim 1, wherein the heterologous polypeptide comprises a green fluorescent protein.

8. The polypeptide of claim 1, wherein the polypeptide has a molecular weight ranging from 80 kDa to 150 kDa.

9. The polypeptide of claim 1, wherein the polypeptide retains one or more of a histone deacetylase activity or a histone binding activity.

10. The polypeptide of claim 1, wherein the polypeptide modulates cellular proliferation.

11. The polypeptide of claim 1, wherein the polypeptide comprises an amino acid sequence identical to SEQ ID NO: 4 fused to an epitope tag.

12. The polypeptide of claim 11, wherein the epitope tag is a FLAG, V5, or HisA tag.

13. The polypeptide of claim 1, wherein the heterologous polypeptide comprises an immunoglobulin.

14. The polypeptide of claim 13, wherein the epitope tag is a HisA tag.

15. The polypeptide of claim 5, wherein the polypeptide is adsorbed onto glutathione sepharose beads or glutathione derivatized microtitre plates.

16. The polypeptide of claim 1, wherein the heterologous polypeptide is streptavidin.

17. A polypeptide comprising an amino acid sequence identical to SEQ ID NO: 4 fused to a biotin moiety.

18. A polypeptide consisting of an amino acid sequence identical to SEQ ID NO: 9 fused to glutathione-S-transferase.

19. A composition comprising the polypeptide of claim 1 and a carrier.

20. An assay for screening test compounds to identify agents which inhibit the deacetylation of histones comprising:
providing a reaction mixture comprising the polypeptide of claim 1 and a test compound, wherein conversion of substrate to product in the reaction mixture is indicative of histone deacetylase activity; and
determining the extent of conversion of substrate to product in the reaction mixture in the presence of a test compound, wherein a statistically significant decrease in the conversion of the substrate in the presence of the test compound indicates that the test compound is a potential inhibitor of histone deacetylation.

21. An assay for screening test compounds to identify agents which inhibit the deacetylation of histones comprising:
providing a reaction mixture comprising the polypeptide of claim 11 and a spatially segregated combinatorial small molecule library; and
detecting the presence of the polypeptide of claim 11 bound at a specific position of the spatially segregated combinatorial small molecule library, wherein the position indicates the identity of the small molecule inhibitor, thereby identifying an agent which inhibits the deacetylation of histones.

22. An assay for screening test compounds to identify agents which inhibit histone deacetylase interaction with cellular proteins comprising:
providing a reaction mixture comprising the polypeptide of claim 1, a histone deacetylase binding protein, and a test compound; and
detecting the interaction of the polypeptide of claim 1 and the histone deacetylase binding protein, wherein a statistically significant decrease in the interaction of the polypeptide of claim 1 and the histone deacetylase binding protein in the presence of the test compound indicates that the test compound is a potential inhibitor of histone deacetylation.

23. The assay of claim 22, wherein the histone deacetylase binding protein is selected from: a histone, a 14-3-3 protein, a MEF2 transcription factor, and a retinoblastoma associated protein.

* * * * *

UNITED STATES PATENT AND TRADEMARK OFFICE
CERTIFICATE OF CORRECTION

PATENT NO. : 8,895,284 B2
APPLICATION NO. : 13/888937
DATED : November 25, 2014
INVENTOR(S) : Christina M. Grozinger et al.

It is certified that error appears in the above-identified patent and that said Letters Patent is hereby corrected as shown below:

In the Specification

At Column 1, Lines 29-33, the paragraph:
"This invention was made with government support under grant number GM38617 awarded by the National Institute of General Medical Sciences. The government has certain rights in the invention."

Should be changed to:
--This invention was made with government support under GM038627 awarded by the National Institutes of Health. The government has certain rights in the invention.--

Signed and Sealed this
Thirteenth Day of August, 2024

Katherine Kelly Vidal
*Director of the United States Patent and Trademark Office*

SEQUENCE LISTING

<160> NUMBER OF SEQ ID NOS: 73

<210> SEQ ID NO 1
<211> LENGTH: 3255

<212> TYPE: DNA
<213> ORGANISM: Homo sapiens

<400> SEQUENCE: 1

| | | | | | |
|---|---|---|---|---|---|
| atgagctccc | aaagccatcc | agatggactt | tctggccgag | accagccagt | ggagctgctg | 60 |
| aatcctgccc | gcgtgaacca | catgcccagc | acggtggatg | tggccacggc | gctgcctctg | 120 |
| caagtggccc | cctcggcagt | gcccatggac | ctgcgcctgg | accaccagtt | ctcactgcct | 180 |
| gtggcagagc | cggccctgcg | ggagcagcag | ctgcagcagg | agctcctggc | gctcaagcag | 240 |
| aagcagcaga | tccagaggca | gatcctcatc | gctgagttcc | agaggcagca | cgagcagctc | 300 |
| tcccggcagc | acgaggcgca | gctccacgag | cacatcaagc | aacaacagga | gatgctggcc | 360 |
| atgaagcacc | agcaggagct | gctggaacac | cagcggaagc | tggagaggca | ccgccaggag | 420 |
| caggagctgg | agaagcagca | ccgggagcag | aagctgcagc | agctcaagaa | caaggagaag | 480 |
| ggcaaagaga | gtgccgtggc | cagcacagaa | gtgaagatga | agttacaaga | atttgtcctc | 540 |
| aataaaaaga | aggcgctggc | ccaccggaat | ctgaaccact | gcatttccag | cgaccctcgc | 600 |
| tactggtacg | ggaaaacgca | gcacagttcc | cttgaccaga | gttctccacc | ccagagcgga | 660 |
| gtgtcgacct | cctataacca | cccggtcctg | gaatgtacg | acgccaaaga | tgacttccct | 720 |
| cttaggaaaa | cagcttctga | accgaatctg | aaattacggt | ccaggctaaa | gcagaaagtg | 780 |
| gccgaaagac | ggagcagccc | cctgttacgc | aggaaagacg | ggccagtggt | cactgctcta | 840 |
| aaaaagcgtc | cgttggatgt | cacagactcc | gcgtgcagca | gcgcccagg | ctccggaccc | 900 |
| agctcaccca | caacagctc | cgggagcgtc | agcgcggaga | acggtatcgc | gcccgccgtc | 960 |
| cccagcatcc | cggcggagac | gagtttggcg | cacagacttg | tggcacgaga | aggctcggcc | 1020 |
| gctccacttc | ccctctacac | atcgccatcc | ttgcccaaca | tcacgctggg | cctgcctgcc | 1080 |
| accggcccct | ctgcgggcac | ggcgggccag | caggacaccg | agagactcac | ccttcccgcc | 1140 |
| ctccagcaga | ggctctcccct | tttccccggc | acccacctca | ctccctacct | gagcacctcg | 1200 |
| cccttggagc | gggacggagg | ggcagcgcac | agccctcttc | tgcagcacat | ggtcttactg | 1260 |
| gagcagccac | cggcacaagc | acccctcgtc | acaggcctgg | gagcactgcc | cctccacgca | 1320 |
| cagtccttgg | ttggtgcaga | ccgggtgtcc | ccctccatcc | acaagctgcg | gcagcaccgc | 1380 |
| ccactggggc | ggacccagtc | ggccccgctg | ccccagaacg | cccaggctct | gcagcacctg | 1440 |
| gtcatccagc | agcagcatca | gcagtttctg | gagaaacaca | agcagcagtt | ccagcagcag | 1500 |
| caactgcaga | tgaacaagat | catccccaag | ccaagcgagc | cagcccggca | gccggagagc | 1560 |
| cacccggagg | agacggagga | ggagctccgt | gagcaccagg | ctctgctgga | cgagccctac | 1620 |
| ctggaccggc | tgccggggca | gaaggaggcg | cacgcacagg | ccggcgtgca | ggtgaagcag | 1680 |
| gagcccattg | agagcgatga | ggaagaggca | gagccccac | gggaggtgga | gccgggccag | 1740 |
| cgccagccca | gtgagcagga | gctgctcttc | agacagcaag | ccctcctgct | ggagcagcag | 1800 |
| cggatccacc | agctgaggaa | ctaccaggcg | tccatggagg | ccgccggcat | ccccgtgtcc | 1860 |
| ttcggcggcc | acaggcctct | gtcccgggcg | cagtcctcac | ccgcgtctgc | caccttcccc | 1920 |
| gtgtctgtgc | aggagccccc | caccaagccg | aggttcacga | caggcctcgt | gtatgacacg | 1980 |
| ctgatgctga | agcaccagtg | cacctgcggg | agtagcagca | gccaccccga | gcacgccggg | 2040 |
| aggatccaga | gcatctggtc | ccgcctgcag | gagacgggcc | tccggggcaa | atgcgagtgc | 2100 |
| atccgcggac | gcaaggccac | cctggaggag | ctacagacgg | tgcactcgga | agcccacacc | 2160 |
| ctcctgtatg | gcacgaaccc | cctcaaccgg | cagaaactgg | acagtaagaa | acttctaggc | 2220 |

```
tcgctcgcct ccgtgttcgt ccggctccct tgcggtggtg ttggggtgga cagtgacacc    2280
atatggaacg aggtgcactc ggcgggggca gcccgcctgg ctgtgggctg cgtggtagag    2340
ctggtcttca aggtggccac aggggagctg aagaatggct ttgctgtggt ccgcccccct    2400
ggacaccatg cggaggagag cacgcccatg ggcttttgct acttcaactc cgtggccgtg    2460
gcagccaagc ttctgcagca gaggttgagc gtgagcaaga tcctcatcgt ggactgggac    2520
gtgcaccatg gaaacgggac ccagcaggct ttctacagcg accctagcgt cctgtacatg    2580
tccctccacc gctacgacga tgggaacttc ttcccaggca gcgggctcc tgatgaggtg     2640
ggcacagggc ccggcgtggg tttcaacgtc aacatggctt tcaccggcgg cctggacccc    2700
cccatgggag acgctgagta cttggcggcc ttcagaacgg tggtcatgcc gatcgccagc    2760
gagtttgccc cggatgtggt gctggtgtca tcaggcttcg atgccgtgga gggccacccc    2820
acccctcttg ggggctacaa cctctccgcc agatgcttcg ggtacctgac gaagcagctg    2880
atgggcctgg ctggcggccg gattgtcctg gccctcgagg gaggccacga cctgaccgcc    2940
atttgcgacg cctcggaagc atgtgttcct gccttgctgg gaaacgagct tgatcctctc    3000
ccagaaaagg ttttacagca aagacccaat gcaaacgctg tccgttccat ggagaaagtc    3060
atggagatcc acagcaagta ctggcgctgc ctgcagcgca caacctccac agcggggcgt    3120
tctctgatcg aggctcagac ttgcgagaac gaagaagccg agacggtcac cgccatggcc    3180
tcgctgtccg tgggcgtgaa gcccgccgaa aagagaccag atgaggagcc catggaagag    3240
gagccgcccc tgtag                                                    3255

<210> SEQ ID NO 2
<211> LENGTH: 1084
<212> TYPE: PRT
<213> ORGANISM: Homo sapiens

<400> SEQUENCE: 2

Met Ser Ser Gln Ser His Pro Asp Gly Leu Ser Gly Arg Asp Gln Pro
  1               5                  10                  15

Val Glu Leu Leu Asn Pro Ala Arg Val Asn His Met Pro Ser Thr Val
             20                  25                  30

Asp Val Ala Thr Ala Leu Pro Leu Gln Val Ala Pro Ser Ala Val Pro
         35                  40                  45

Met Asp Leu Arg Leu Asp His Gln Phe Ser Leu Pro Val Ala Glu Pro
     50                  55                  60

Ala Leu Arg Glu Gln Gln Leu Gln Gln Glu Leu Leu Ala Leu Lys Gln
 65                  70                  75                  80

Lys Gln Gln Ile Gln Arg Gln Ile Leu Ile Ala Glu Phe Gln Arg Gln
                 85                  90                  95

His Glu Gln Leu Ser Arg Gln His Glu Ala Gln Leu His Glu His Ile
            100                 105                 110

Lys Gln Gln Gln Glu Met Leu Ala Met Lys His Gln Gln Glu Leu Leu
        115                 120                 125

Glu His Gln Arg Lys Leu Glu Arg His Arg Gln Glu Gln Glu Leu Glu
    130                 135                 140

Lys Gln His Arg Glu Gln Lys Leu Gln Gln Leu Lys Asn Lys Glu Lys
145                 150                 155                 160

Gly Lys Glu Ser Ala Val Ala Ser Thr Glu Val Lys Met Lys Leu Gln
                165                 170                 175

Glu Phe Val Leu Asn Lys Lys Lys Ala Leu Ala His Arg Asn Leu Asn
            180                 185                 190
```

-continued

His Cys Ile Ser Ser Asp Pro Arg Tyr Trp Tyr Gly Lys Thr Gln His
          195                 200                 205

Ser Ser Leu Asp Gln Ser Ser Pro Pro Gln Ser Gly Val Ser Thr Ser
210                 215                 220

Tyr Asn His Pro Val Leu Gly Met Tyr Asp Ala Lys Asp Asp Phe Pro
225                 230                 235                 240

Leu Arg Lys Thr Ala Ser Glu Pro Asn Leu Lys Leu Arg Ser Arg Leu
              245                 250                 255

Lys Gln Lys Val Ala Glu Arg Arg Ser Ser Pro Leu Leu Arg Arg Lys
              260                 265                 270

Asp Gly Pro Val Val Thr Ala Leu Lys Lys Arg Pro Leu Asp Val Thr
          275                 280                 285

Asp Ser Ala Cys Ser Ser Ala Pro Gly Ser Gly Pro Ser Ser Pro Asn
290                 295                 300

Asn Ser Ser Gly Ser Val Ser Ala Glu Asn Gly Ile Ala Pro Ala Val
305                 310                 315                 320

Pro Ser Ile Pro Ala Glu Thr Ser Leu Ala His Arg Leu Val Ala Arg
              325                 330                 335

Glu Gly Ser Ala Ala Pro Leu Pro Leu Tyr Thr Ser Pro Ser Leu Pro
          340                 345                 350

Asn Ile Thr Leu Gly Leu Pro Ala Thr Gly Pro Ser Ala Gly Thr Ala
          355                 360                 365

Gly Gln Gln Asp Thr Glu Arg Leu Thr Leu Pro Ala Leu Gln Gln Arg
          370                 375                 380

Leu Ser Leu Phe Pro Gly Thr His Leu Thr Pro Tyr Leu Ser Thr Ser
385                 390                 395                 400

Pro Leu Glu Arg Asp Gly Gly Ala Ala His Ser Pro Leu Leu Gln His
              405                 410                 415

Met Val Leu Leu Glu Gln Pro Ala Gln Ala Pro Leu Val Thr Gly
              420                 425                 430

Leu Gly Ala Leu Pro Leu His Ala Gln Ser Leu Val Gly Ala Asp Arg
          435                 440                 445

Val Ser Pro Ser Ile His Lys Leu Arg Gln His Arg Pro Leu Gly Arg
450                 455                 460

Thr Gln Ser Ala Pro Leu Pro Gln Asn Ala Gln Ala Leu Gln His Leu
465                 470                 475                 480

Val Ile Gln Gln Gln His Gln Gln Phe Leu Glu Lys His Lys Gln Gln
              485                 490                 495

Phe Gln Gln Gln Gln Leu Gln Met Asn Lys Ile Ile Pro Lys Pro Ser
              500                 505                 510

Glu Pro Ala Arg Gln Pro Glu Ser His Pro Glu Glu Thr Glu Glu Glu
          515                 520                 525

Leu Arg Glu His Gln Ala Leu Leu Asp Glu Pro Tyr Leu Asp Arg Leu
530                 535                 540

Pro Gly Gln Lys Glu Ala His Ala Gln Ala Gly Val Gln Val Lys Gln
545                 550                 555                 560

Glu Pro Ile Glu Ser Asp Glu Glu Ala Glu Pro Pro Arg Glu Val
              565                 570                 575

Glu Pro Gly Gln Arg Gln Pro Ser Glu Gln Glu Leu Leu Phe Arg Gln
          580                 585                 590

Gln Ala Leu Leu Leu Glu Gln Gln Arg Ile His Gln Leu Arg Asn Tyr
          595                 600                 605

-continued

```
Gln Ala Ser Met Glu Ala Ala Gly Ile Pro Val Ser Phe Gly Gly His
    610                 615                 620
Arg Pro Leu Ser Arg Ala Gln Ser Ser Pro Ala Ser Ala Thr Phe Pro
625                 630                 635                 640
Val Ser Val Gln Glu Pro Pro Thr Lys Pro Arg Phe Thr Thr Gly Leu
                645                 650                 655
Val Tyr Asp Thr Leu Met Leu Lys His Gln Cys Thr Cys Gly Ser Ser
            660                 665                 670
Ser Ser His Pro Glu His Ala Gly Arg Ile Gln Ser Ile Trp Ser Arg
        675                 680                 685
Leu Gln Glu Thr Gly Leu Arg Gly Lys Cys Glu Cys Ile Arg Gly Arg
    690                 695                 700
Lys Ala Thr Leu Glu Glu Leu Gln Thr Val His Ser Glu Ala His Thr
705                 710                 715                 720
Leu Leu Tyr Gly Thr Asn Pro Leu Asn Arg Gln Lys Leu Asp Ser Lys
                725                 730                 735
Lys Leu Leu Gly Ser Leu Ala Ser Val Phe Val Arg Leu Pro Cys Gly
            740                 745                 750
Gly Val Gly Val Asp Ser Asp Thr Ile Trp Asn Glu Val His Ser Ala
        755                 760                 765
Gly Ala Ala Arg Leu Ala Val Gly Cys Val Val Glu Leu Val Phe Lys
    770                 775                 780
Val Ala Thr Gly Glu Leu Lys Asn Gly Phe Ala Val Val Arg Pro Pro
785                 790                 795                 800
Gly His His Ala Glu Glu Ser Thr Pro Met Gly Phe Cys Tyr Phe Asn
                805                 810                 815
Ser Val Ala Val Ala Ala Lys Leu Leu Gln Gln Arg Leu Ser Val Ser
            820                 825                 830
Lys Ile Leu Ile Val Asp Trp Asp Val His His Gly Asn Gly Thr Gln
        835                 840                 845
Gln Ala Phe Tyr Ser Asp Pro Ser Val Leu Tyr Met Ser Leu His Arg
    850                 855                 860
Tyr Asp Asp Gly Asn Phe Phe Pro Gly Ser Gly Ala Pro Asp Glu Val
865                 870                 875                 880
Gly Thr Gly Pro Gly Val Gly Phe Asn Val Asn Met Ala Phe Thr Gly
                885                 890                 895
Gly Leu Asp Pro Pro Met Gly Asp Ala Glu Tyr Leu Ala Ala Phe Arg
            900                 905                 910
Thr Val Val Met Pro Ile Ala Ser Glu Phe Ala Pro Asp Val Val Leu
        915                 920                 925
Val Ser Ser Gly Phe Asp Ala Val Glu Gly His Pro Thr Pro Leu Gly
    930                 935                 940
Gly Tyr Asn Leu Ser Ala Arg Cys Phe Gly Tyr Leu Thr Lys Gln Leu
945                 950                 955                 960
Met Gly Leu Ala Gly Gly Arg Ile Val Leu Ala Leu Glu Gly Gly His
                965                 970                 975
Asp Leu Thr Ala Ile Cys Asp Ala Ser Glu Ala Cys Val Ser Ala Leu
            980                 985                 990
Leu Gly Asn Glu Leu Asp Pro Leu Pro Glu Lys Val Leu Gln Gln Arg
        995                1000                1005
Pro Asn Ala Asn Ala Val Arg Ser Met Glu Lys Val Met Glu Ile His
    1010                1015                1020
Ser Lys Tyr Trp Arg Cys Leu Gln Arg Thr Thr Ser Thr Ala Gly Arg
```

Ser Leu Ile Glu Ala Gln Thr Cys Glu Asn Glu Glu Ala Glu Thr Val
1045             1050             1055

Thr Ala Met Ala Ser Leu Ser Val Gly Val Lys Pro Ala Glu Lys Arg
1060             1065             1070

Pro Asp Glu Glu Pro Met Glu Glu Glu Pro Pro Leu
1075             1080

<210> SEQ ID NO 3
<211> LENGTH: 3369
<212> TYPE: DNA
<213> ORGANISM: Homo sapiens

<400> SEQUENCE: 3

```
atgaactctc ccaacgagtc ggatgggatg tcaggtcggg aaccatcctt ggaaatcctg    60
ccgcggactt ctctgcacag catccctgtg acagtggagg tgaagccggt gctgccaaga   120
gccatgccca gttccatggg gggtgggggt ggaggcagcc ccagccctgt ggagctacgg   180
ggggctctgg tgggctctgt ggaccccaca ctgcgggagc agcaactgca gcaggagctc   240
ctggcgctca gcagcagca gcagctgcag aagcagctcc tgttcgctga gttccagaaa   300
cagcatgacc acctgacaag gcagcatgag gtccagctgc agaagcacct caagcagcag   360
caggagatgc tggcagccaa gcagcagcag agatgctgg cagccaagcg gcagcaggag   420
ctggagcagc agcggcagcg ggagcagcag cggcaggaag agctggagaa gcagcggctg   480
gagcagcagc tgctcatcct gcggaacaag gagaagagca agagagtgc cattgccagc   540
actgaggtaa agctgaggct ccaggaattc ctcttgtcga agtcaaagga gcccacacca   600
ggcggcctca accattccct cccacagcac cccaaatgct ggggagccca ccatgcttct   660
ttggaccaga gttcccctcc ccagagcggc cccctggga cgcctccctc ctacaaactg   720
cctttgcctg ggccctacga cagtcgagac gacttccccc tccgcaaaac agcctctgaa   780
cccaacttga aagtgcgttc aaggctaaaa cagaaggtgg ctgagcggag aagcagtccc   840
ctcctgcgtc gcaaggatgg gactgttatt agcacccttta agaagagagc tgttgagatc   900
acaggtgccg ggcctgggc gtcgtccgtg tgtaacagcg cacccggctc cggccccagc   960
tctcccaaca gctcccacag caccatcgct gagaatggct ttactggctc agtccccaac  1020
atccccactg agatgctccc tcagcaccga gccctccctc tggacagctc ccccaaccag  1080
ttcagcctct acacgtctcc ttctctgccc aacatctccc tagggctgca ggccacggtc  1140
actgtcacca actcacacct cactgcctcc ccgaagctgt cgacacagca ggaggccgag  1200
aggcaggccc tccagtccct gcggcagggt ggcacgctga ccggcaagtt catgagcaca  1260
tcctctattc ctggctgcct gctgggcgtg cactggaggg cgacgggag ccccacgggg  1320
catgcctccc tgctgcagca tgtgctgttg ctggagcagg cccggcagca gagcaccctc  1380
attgctgtgc cactccacgg gcagtcccca ctagtgacgg gtgaacgtgt ggccaccagc  1440
atgcggacgg taggcaagct cccgcggcat cggcccctga ccgcactca gtcctcaccg  1500
ctgccgcaga gtccccaggc cctgcagcag ctggtcatgc aacaacagca ccagcagttc  1560
ctggagaagc agaagcagca gcagctacag ctgggcaaga tcctcaccaa gacagggag  1620
ctgcccaggc agcccaccac ccaccctgag gagacagagg aggagctgac ggagcagcag  1680
gaggtcttgc tggggagg agccctgacc atgcccgg agggctccac agagagtgag  1740
agcacacagg aagacctgga ggaggaggac gaggaagagg atggggagga ggaggaggat  1800
```

-continued

```
tgcatccagg ttaaggacga ggagggcgag agtggtgctg aggaggggcc cgacttggag      1860
gagcctggtg ctggatacaa aaaactgttc tcagatgccc agccgctgca gcctttgcag      1920
gtgtaccagg cgcccctcag cctggccact gtgccccacc aggccctggg ccgtacccag      1980
tcctcccctg ctgccctggg ggcatgaag agcccccag accagcccgt caagcacctc        2040
ttcaccacag gtgtggtcta cgacacgttc atgctaaagc accagtgcat gtgcgggaac      2100
acacacgtgc accctgagca tgctggccgg atccagagca tctggtcccg gctgcaggag      2160
acaggcctgc ttagcaagtg cgagcggatc cgaggtcgca aagccacgct agatgagatc      2220
cagacagtgc actctgaata ccacaccctg ctctatggga ccagtcccct caaccggcag      2280
aagctagaca gcaagaagtt gctcggcccc atcagccaga agatgtatgc tgtgctgcct     2340
tgtgggggca tcgggggtgga cagtgacacc gtgtggaatg agatgcactc ctccagtgct    2400
gtgcgcatgg cagtgggctg cctgctggag ctggccttca aggtggctgc aggagagctc      2460
aagaatggat ttgccatcat ccggcccca ggacaccacg ccgaggaatc cacagccatg      2520
ggattctgct tcttcaactc tgtagccatc accgcaaaac tcctacagca gaagttgaac     2580
gtgggcaagg tcctcatcgt ggactgggac attcaccatg gcaatggcac ccagcaggcg      2640
ttctataatg accctctgt gctctacatc tctctgcatc gctatgacaa cgggaacttc       2700
tttccaggct ctggggctcc tgaagaggtt ggtggaggac caggcgtggg gtacaatgtg      2760
aacgtggcat ggacaggagg tgtggacccc cccattggag acgtggagta ccttacagcc     2820
ttcaggacag tggtgatgcc cattgcccac gagttctcac ctgatgtggt cctagtctcc     2880
gccgggtttg atgctgttga aggacatctg tctcctctgg gtggctactc tgtcaccgcc     2940 agatgtttg ccacttgac caggcagctg atgaccctgg caggggccg ggtggtgctg        3000 gccctggagg gaggccatga cttgaccgcc atctgtgatg cctctgaggc ttgtgtctcg     3060
gctctgctca gtgtagagct gcagcccttg gatgaggcag tcttgcagca aaagcccaac     3120
atcaacgcag tggccacgct agagaaagtc atcgagatcc agagcaaaca ctggagctgt    3180
gtgcagaagt tcgccgctgg tctgggccgg tccctgcgag aggcccaagc aggtgagacc    3240
gaggaggccg agactgtgag cgccatggcc ttgctgtcgg tgggggccga gcaggcccag    3300
gctgcggcag cccgggaaca cagccccagg ccggcagagg agcccatgga gcaggagcct    3360
gccctgtga                                                              3369
```

<210> SEQ ID NO 4
<211> LENGTH: 1122
<212> TYPE: PRT
<213> ORGANISM: Homo sapiens

<400> SEQUENCE: 4

Met Asn Ser Pro Asn Glu Ser Asp Gly Met Ser Gly Arg Glu Pro Ser
 1               5                  10                  15

Leu Glu Ile Leu Pro Arg Thr Ser Leu His Ser Ile Pro Val Thr Val
            20                  25                  30

Glu Val Lys Pro Val Leu Pro Arg Ala Met Pro Ser Ser Met Gly Gly
        35                  40                  45

Gly Gly Gly Gly Ser Pro Ser Pro Val Glu Leu Arg Gly Ala Leu Val
    50                  55                  60

Gly Ser Val Asp Pro Thr Leu Arg Glu Gln Gln Leu Gln Gln Glu Leu
65                  70                  75                  80

Leu Ala Leu Lys Gln Gln Gln Gln Leu Gln Lys Gln Leu Leu Phe Ala
                85                  90                  95

-continued

```
Glu Phe Gln Lys Gln His Asp His Leu Thr Arg Gln His Glu Val Gln
            100                 105                 110

Leu Gln Lys His Leu Lys Gln Gln Glu Met Leu Ala Ala Lys Gln
        115                 120                 125

Gln Gln Glu Met Leu Ala Ala Lys Arg Gln Gln Glu Leu Glu Gln Gln
    130                 135                 140

Arg Gln Arg Glu Gln Gln Arg Gln Glu Glu Leu Glu Lys Gln Arg Leu
145                 150                 155                 160

Glu Gln Gln Leu Leu Ile Leu Arg Asn Lys Glu Lys Ser Lys Glu Ser
                165                 170                 175

Ala Ile Ala Ser Thr Glu Val Lys Leu Arg Leu Gln Glu Phe Leu Leu
            180                 185                 190

Ser Lys Ser Lys Glu Pro Thr Pro Gly Gly Leu Asn His Ser Leu Pro
        195                 200                 205

Gln His Pro Lys Cys Trp Gly Ala His His Ala Ser Leu Asp Gln Ser
    210                 215                 220

Ser Pro Pro Gln Ser Gly Pro Gly Thr Pro Ser Tyr Lys Leu
225                 230                 235                 240

Pro Leu Pro Gly Pro Tyr Asp Ser Arg Asp Asp Phe Pro Leu Arg Lys
                245                 250                 255

Thr Ala Ser Glu Pro Asn Leu Lys Val Arg Ser Arg Leu Lys Gln Lys
            260                 265                 270

Val Ala Glu Arg Arg Ser Ser Pro Leu Leu Arg Arg Lys Asp Gly Thr
        275                 280                 285

Val Ile Ser Thr Phe Lys Lys Arg Ala Val Glu Ile Thr Gly Ala Gly
    290                 295                 300

Pro Gly Ala Ser Ser Val Cys Asn Ser Ala Pro Gly Ser Gly Pro Ser
305                 310                 315                 320

Ser Pro Asn Ser Ser His Ser Thr Ile Ala Glu Asn Gly Phe Thr Gly
                325                 330                 335

Ser Val Pro Asn Ile Pro Thr Glu Met Leu Pro Gln His Arg Ala Leu
            340                 345                 350

Pro Leu Asp Ser Ser Pro Asn Gln Phe Ser Leu Tyr Thr Ser Pro Ser
        355                 360                 365

Leu Pro Asn Ile Ser Leu Gly Leu Gln Ala Thr Val Thr Val Thr Asn
    370                 375                 380

Ser His Leu Thr Ala Ser Pro Lys Leu Ser Thr Gln Gln Glu Ala Glu
385                 390                 395                 400

Arg Gln Ala Leu Gln Ser Leu Arg Gln Gly Gly Thr Leu Thr Gly Lys
                405                 410                 415

Phe Met Ser Thr Ser Ser Ile Pro Gly Cys Leu Leu Gly Val Ala Leu
            420                 425                 430

Glu Gly Asp Gly Ser Pro His Gly His Ala Ser Leu Leu Gln His Val
        435                 440                 445

Leu Leu Leu Glu Gln Ala Arg Gln Gln Ser Thr Leu Ile Ala Val Pro
    450                 455                 460

Leu His Gly Gln Ser Pro Leu Val Thr Gly Glu Arg Val Ala Thr Ser
465                 470                 475                 480

Met Arg Thr Val Gly Lys Leu Pro Arg His Arg Pro Leu Ser Arg Thr
                485                 490                 495

Gln Ser Ser Pro Leu Pro Gln Ser Pro Gln Ala Leu Gln Gln Leu Val
            500                 505                 510
```

-continued

```
Met Gln Gln Gln His Gln Gln Phe Leu Glu Lys Gln Lys Gln Gln
            515                 520                 525
Leu Gln Leu Gly Lys Ile Leu Thr Lys Thr Gly Glu Leu Pro Arg Gln
    530                 535                 540
Pro Thr Thr His Pro Glu Glu Thr Glu Glu Leu Thr Glu Gln Gln
545                 550                 555                 560
Glu Val Leu Leu Gly Glu Gly Ala Leu Thr Met Pro Arg Glu Gly Ser
                565                 570                 575
Thr Glu Ser Glu Ser Thr Gln Glu Asp Leu Glu Glu Asp Glu Glu
            580                 585                 590
Glu Asp Gly Glu Glu Glu Glu Asp Cys Ile Gln Val Lys Asp Glu Glu
            595                 600                 605
Gly Glu Ser Gly Ala Glu Glu Gly Pro Asp Leu Glu Glu Pro Gly Ala
            610                 615                 620
Gly Tyr Lys Lys Leu Phe Ser Asp Ala Gln Pro Leu Gln Pro Leu Gln
625                 630                 635                 640
Val Tyr Gln Ala Pro Leu Ser Leu Ala Thr Val Pro His Gln Ala Leu
                645                 650                 655
Gly Arg Thr Gln Ser Ser Pro Ala Ala Pro Gly Gly Met Lys Ser Pro
            660                 665                 670
Pro Asp Gln Pro Val Lys His Leu Phe Thr Thr Gly Val Val Tyr Asp
675                 680                 685
Thr Phe Met Leu Lys His Gln Cys Met Cys Gly Asn Thr His Val His
    690                 695                 700
Pro Glu His Ala Gly Arg Ile Gln Ser Ile Trp Ser Arg Leu Gln Glu
705                 710                 715                 720
Thr Gly Leu Leu Ser Lys Cys Glu Arg Ile Arg Gly Arg Lys Ala Thr
                725                 730                 735
Leu Asp Glu Ile Gln Thr Val His Ser Glu Tyr His Thr Leu Leu Tyr
            740                 745                 750
Gly Thr Ser Pro Leu Asn Arg Gln Lys Leu Asp Ser Lys Lys Leu Leu
        755                 760                 765
Gly Pro Ile Ser Gln Lys Met Tyr Ala Val Leu Pro Cys Gly Gly Ile
    770                 775                 780
Gly Val Asp Ser Asp Thr Val Trp Asn Glu Met His Ser Ser Ser Ala
785                 790                 795                 800
Val Arg Met Ala Val Gly Cys Leu Leu Glu Leu Ala Phe Lys Val Ala
                805                 810                 815
Ala Gly Glu Leu Lys Asn Gly Phe Ala Ile Ile Arg Pro Pro Gly His
            820                 825                 830
His Ala Glu Glu Ser Thr Ala Met Gly Phe Cys Phe Phe Asn Ser Val
            835                 840                 845
Ala Ile Thr Ala Lys Leu Leu Gln Gln Lys Leu Asn Val Gly Lys Val
850                 855                 860
Leu Ile Val Asp Trp Asp Ile His His Gly Asn Gly Thr Gln Gln Ala
865                 870                 875                 880
Phe Tyr Asn Asp Pro Ser Val Leu Tyr Ile Ser Leu His Arg Tyr Asp
                885                 890                 895
Asn Gly Asn Phe Phe Pro Gly Ser Gly Ala Pro Glu Glu Val Gly Gly
            900                 905                 910
Gly Pro Gly Val Gly Tyr Asn Val Asn Val Ala Trp Thr Gly Gly Val
            915                 920                 925
Asp Pro Pro Ile Gly Asp Val Glu Tyr Leu Thr Ala Phe Arg Thr Val
```

Val Met Pro Ile Ala His Glu Phe Ser Pro Asp Val Val Leu Val Ser
945                 950                 955                 960

Ala Gly Phe Asp Ala Val Glu Gly His Leu Ser Pro Leu Gly Gly Tyr
            965                 970                 975

Ser Val Thr Ala Arg Cys Phe Gly His Leu Thr Arg Gln Leu Met Thr
        980                 985                 990

Leu Ala Gly Gly Arg Val Val Leu Ala Leu Glu Gly Gly His Asp Leu
    995                 1000                1005

Thr Ala Ile Cys Asp Ala Ser Glu Ala Cys Val Ser Ala Leu Leu Ser
    1010                1015                1020

Val Glu Leu Gln Pro Leu Asp Glu Ala Val Leu Gln Gln Lys Pro Asn
1025                1030                1035                1040

Ile Asn Ala Val Ala Thr Leu Glu Lys Val Ile Glu Ile Gln Ser Lys
                1045                1050                1055

His Trp Ser Cys Val Gln Lys Phe Ala Ala Gly Leu Gly Arg Ser Leu
            1060                1065                1070

Arg Glu Ala Gln Ala Gly Glu Thr Glu Glu Ala Glu Thr Val Ser Ala
        1075                1080                1085

Met Ala Leu Leu Ser Val Gly Ala Glu Gln Ala Gln Ala Ala Ala Ala
    1090                1095                1100

Arg Glu His Ser Pro Arg Pro Ala Glu Glu Pro Met Glu Gln Glu Pro
1105                1110                1115                1120

Ala Leu

<210> SEQ ID NO 5
<211> LENGTH: 3648
<212> TYPE: DNA
<213> ORGANISM: Homo sapiens

<400> SEQUENCE: 5
atgacctcaa ccggccagga ttccaccaca accaggcagc aagaagtag gcagaacccc      60 cagtcgcccc ctcaggactc cagtgtcact tcgaagcgaa atattaaaaa gggagccgtt     120
ccccgctcta tccccaatct agcggaggta agaagaaag gcaaaatgaa gaagctcggc     180
caagcaatgg aagaagacct aatcgtggga ctgcaaggga tggatctgaa ccttgaggct     240
gaagcactgg ctggcactgg cttggtgttg atgagcagt taaatgaatt ccattgcctc     300
tgggatgaca gcttcccgga aggccctgag cggctccatg ccatcaagga gcaactgatc     360
caggagggcc tcctagatcg ctgcgtgtcc tttcaggccc ggtttgctga aaaggaagag     420
ctgatgttgg ttcacagcct agaatatatt gatctgatgg aaacaaccca gtacatgaat     480
gagggagaac tccgtgtcct agcagacacc tacgactcag tttatctgca tccgaactca     540
tactcctgtg cctgcctggc ctcaggctct gtcctcaggc tggtggatgc ggtcctgggg     600
gctgagatcc ggaatggcat ggccatcatt aggcctcctg acatcacgc ccagcacagt     660 cttatggatg ctattgcat gttcaaccac gtggctgtgg cagcccgcta tgctcaacag     720
aaacaccgca tccggagggt ccttatcgta gattgggatg tgcaccacgg tcaaggaaca     780
cagttcacct tcgaccagga ccccagtgtc ctctatttct ccatccaccg ctacgagcag     840
ggtaggttct ggccccacct gaaggcctct aactggtcca ccacaggttt cggccaaggc     900
caaggatata ccatcaatgt gccttggaac caggtgggga tgcgggatgc tgactacatt     960
gctgctttcc tgcacgtcct gctgccagtc gccctcgagt tccagcctca gctggtcctg    1020

```
gtggctgctg gatttgatgc cctgcaaggg gaccccaagg gtgagatggc cgccactccg    1080
gcagggttcg cccagctaac ccacctgctc atgggtctgg caggaggcaa gctgatcctg    1140
tctctggagg gtggctacaa cctccgcgcc ctggctgaag gcgtcagtgc ttcgctccac    1200
acccttctgg gagaccccttg ccccatgctg gagtcacctg gtgcccsctg ccggagtgcc    1260
caggcttcag tttcctgtgc tctggaagcc cttgagccct tctgggaggt tcttgtgaga    1320
tcaactgaga ccgtggagag ggacaacatg gaggaggaca atgtagagga gagcgaggag    1380
gaaggaccct gggagccccc tgtgctccca atcctgacat ggccagtgct acagtctcgc    1440
acagggctgg tctatgacca aaatatgatg aatcactgca acttgtggga cagccaccac    1500
cctgaggtac cccagcgcat cttgcggatc atgtgccgtc tggaggagct gggccttgcc    1560
gggcgctgcc tcaccctgac accgcgccct gccacagagg ctgagctgct cacctgtcac    1620
agtgctgagt acgtgggtca tctccgggcc acagagaaaa tgaaacccg ggagctgcac    1680 cgtgagagtt ccaactttga ctccatctat atctgcccca gtaccttcgc ctgtgcacag    1740
cttgccactg gcgctgcctg ccgcctggtg gaggctgtgc tctcaggaga ggttctgaat    1800
ggtgctgctg tggtgcgtcc cccaggacac cacgcagagc aggatgcagc ttgcggtttt    1860 tgcttttca actctgtggc tgtggctgct cgccatgccc agactatcag tgggcatgcc    1920
ctacggatcc tgattgtgga ttgggatgtc caccacggta atggaactca gcacatgttt    1980
gaggatgacc ccagtgtgct atatgtgtcc ctgcaccgct atgatcatgg caccttcttc    2040
cccatggggg atgagggtgc cagcagccag atcggccggg ctgcgggcac aggcttcacc    2100
gtcaacgtgg catggaacgg ccccgcatg ggtgatgctg actacctagc tgcctggcat    2160
cgcctggtgc ttcccattgc ctacgagttt aacccagaac tggtgctggt ctcagctggc    2220
tttgatgctg cacgggggga tccgctgggg gctgccagg tgtcacctga gggttatgcc    2280
cacctcaccc acctgctgat gggccttgcc agtggccgca ttatccttat cctagagggt    2340
ggctataacc tgacatccat ctcagagtcc atggctgcct gcactcgctc cctccttgga    2400
gacccaccac ccctgctgac cctgccacgg ccccactat caggggccct ggcctcaatc    2460
actgagacca tccaagtcca tcgcagatac tggcgcagct acgggtcat gaaggtagaa    2520 gacagagaag gaccctccag ttctaagttg gtcaccaaga aggcaccca accagccaaa    2580 cctaggttag ctgagcggat gaccacacga gaaaagaagg ttctggaagc aggcatgggg    2640
aaagtcacct cggcatcatt tggggaagag tccactccag gccagactaa ctcagagaca    2700
gctgtggtgg ccctcactca ggaccagccc tcagaggcag ccacagggg agccactctg    2760 gcccagacca tttctgaggc agccattggg ggagccatgc tgggccagac cacctcagag    2820
gaggctgtcg ggggagccac tccggaccag accacctcag aggagactgt gggaggagcc    2880
attctggacc agaccacctc agaggatgct gttggggag ccacgctggg ccagactacc    2940
tcagaggagg ctgtaggagg agctacactg gcccagacca tctcggaggc agccatggag    3000
ggagccacac tggaccagac tacgtcagag gaggctccag ggggcaccga gctgatccaa    3060
actcctctag cctcgagcac agaccaccag acccccccaa cctcacctgt gcagggaact    3120
acacccagaa tatctcccag tacactgatt gggagtctca ggaccttgga gctaggcagc    3180
gaatctcagg gggcctcaga atctcaggcc ccaggagagg agaacctact aggagaggca    3240
gctggaggtc aggacatggc tgattcgatg ctgatgcagg gatctagggg cctcactgat    3300
caggccatat tttatgctgt gacaccactg ccctggtgtc cccatttggt ggcagtatgc    3360 cccataccctg cagcaggcct agacgtgacc caaccttgtg gggactgtgg aacaatccaa    3420
```

```
gagaattggg tgtgtctctc ttgctatcag gtctactgtg gtcgttacat caatggccac    3480
atgctccaac accatggaaa ttctggacac ccgctggtcc tcagctacat cgacctgtca    3540
gcctggtgtt actactgtca ggcctatgtc caccaccagg ctctcctaga tgtgaagaac    3600
atcgcccacc agaacaagtt tggggaggat atgccccacc cacactaa                 3648
```

<210> SEQ ID NO 6
<211> LENGTH: 1215
<212> TYPE: PRT
<213> ORGANISM: Homo sapiens

<400> SEQUENCE: 6

```
Met Thr Ser Thr Gly Gln Asp Ser Thr Thr Arg Gln Arg Arg Ser
 1               5                  10                  15

Arg Gln Asn Pro Gln Ser Pro Gln Asp Ser Ser Val Thr Ser Lys
                20                  25                  30

Arg Asn Ile Lys Lys Gly Ala Val Pro Arg Ser Ile Pro Asn Leu Ala
                35                  40                  45

Glu Val Lys Lys Gly Lys Met Lys Lys Leu Gly Gln Ala Met Glu
         50                  55                  60

Glu Asp Leu Ile Val Gly Leu Gln Gly Met Asp Leu Asn Leu Glu Ala
 65                  70                  75                  80

Glu Ala Leu Ala Gly Thr Gly Leu Val Leu Asp Glu Gln Leu Asn Glu
                 85                  90                  95

Phe His Cys Leu Trp Asp Asp Ser Phe Pro Glu Gly Pro Glu Arg Leu
                100                 105                 110

His Ala Ile Lys Glu Gln Leu Ile Gln Glu Gly Leu Leu Asp Arg Cys
                115                 120                 125

Val Ser Phe Gln Ala Arg Phe Ala Glu Lys Glu Glu Leu Met Leu Val
                130                 135                 140

His Ser Leu Glu Tyr Ile Asp Leu Met Glu Thr Thr Gln Tyr Met Asn
145                 150                 155                 160

Glu Gly Glu Leu Arg Val Leu Ala Asp Thr Tyr Asp Ser Val Tyr Leu
                165                 170                 175

His Pro Asn Ser Tyr Ser Cys Ala Cys Leu Ala Ser Gly Ser Val Leu
                180                 185                 190

Arg Leu Val Asp Ala Val Leu Gly Ala Glu Ile Arg Asn Gly Met Ala
                195                 200                 205

Ile Ile Arg Pro Pro Gly His His Ala Gln His Ser Leu Met Asp Gly
                210                 215                 220

Tyr Cys Met Phe Asn His Val Ala Val Ala Ala Arg Tyr Ala Gln Gln
225                 230                 235                 240

Lys His Arg Ile Arg Arg Val Leu Ile Val Asp Trp Asp Val His His
                245                 250                 255

Gly Gln Gly Thr Gln Phe Thr Phe Asp Gln Asp Pro Ser Val Leu Tyr
                260                 265                 270

Phe Ser Ile His Arg Tyr Glu Gln Gly Arg Phe Trp Pro His Leu Lys
                275                 280                 285

Ala Ser Asn Trp Ser Thr Thr Gly Phe Gly Gln Gly Gln Gly Tyr Thr
                290                 295                 300

Ile Asn Val Pro Trp Asn Gln Val Gly Met Arg Asp Ala Asp Tyr Ile
305                 310                 315                 320

Ala Ala Phe Leu His Val Leu Leu Pro Val Ala Leu Glu Phe Gln Pro
                325                 330                 335
```

```
Gln Leu Val Leu Val Ala Ala Gly Phe Asp Ala Leu Gln Gly Asp Pro
            340                 345                 350

Lys Gly Glu Met Ala Ala Thr Pro Ala Gly Phe Ala Gln Leu Thr His
            355                 360                 365

Leu Leu Met Gly Leu Ala Gly Gly Lys Leu Ile Leu Ser Leu Glu Gly
            370                 375                 380

Gly Tyr Asn Leu Arg Ala Leu Ala Glu Gly Val Ser Ala Ser Leu His
385                 390                 395                 400

Thr Leu Leu Gly Asp Pro Cys Pro Met Leu Glu Ser Pro Gly Ala Pro
                405                 410                 415

Cys Arg Ser Ala Gln Ala Ser Val Ser Cys Ala Leu Glu Ala Leu Glu
            420                 425                 430

Pro Phe Trp Glu Val Leu Val Arg Ser Thr Glu Thr Val Glu Arg Asp
            435                 440                 445

Asn Met Glu Glu Asp Asn Val Glu Glu Ser Glu Glu Glu Gly Pro Trp
            450                 455                 460

Glu Pro Pro Val Leu Pro Ile Leu Thr Trp Pro Val Leu Gln Ser Arg
465                 470                 475                 480

Thr Gly Leu Val Tyr Asp Gln Asn Met Met Asn His Cys Asn Leu Trp
                485                 490                 495

Asp Ser His His Pro Glu Val Pro Gln Arg Ile Leu Arg Ile Met Cys
            500                 505                 510

Arg Leu Glu Glu Leu Gly Leu Ala Gly Arg Cys Leu Thr Leu Thr Pro
            515                 520                 525

Arg Pro Ala Thr Glu Ala Glu Leu Leu Thr Cys His Ser Ala Glu Tyr
            530                 535                 540

Val Gly His Leu Arg Ala Thr Glu Lys Met Lys Thr Arg Glu Leu His
545                 550                 555                 560

Arg Glu Ser Ser Asn Phe Asp Ser Ile Tyr Ile Cys Pro Ser Thr Phe
                565                 570                 575

Ala Cys Ala Gln Leu Ala Thr Gly Ala Ala Cys Arg Leu Val Glu Ala
            580                 585                 590

Val Leu Ser Gly Glu Val Leu Asn Gly Ala Ala Val Val Arg Pro Pro
            595                 600                 605

Gly His His Ala Glu Gln Asp Ala Ala Cys Gly Phe Cys Phe Phe Asn
            610                 615                 620

Ser Val Ala Val Ala Ala Arg His Ala Gln Thr Ile Ser Gly His Ala
625                 630                 635                 640

Leu Arg Ile Leu Ile Val Asp Trp Asp Val His His Gly Asn Gly Thr
                645                 650                 655

Gln His Met Phe Glu Asp Asp Pro Ser Val Leu Tyr Val Ser Leu His
            660                 665                 670

Arg Tyr Asp His Gly Thr Phe Phe Pro Met Gly Asp Glu Gly Ala Ser
            675                 680                 685

Ser Gln Ile Gly Arg Ala Ala Gly Thr Gly Phe Thr Val Asn Val Ala
            690                 695                 700

Trp Asn Gly Pro Arg Met Gly Asp Ala Asp Tyr Leu Ala Ala Trp His
705                 710                 715                 720

Arg Leu Val Leu Pro Ile Ala Tyr Glu Phe Asn Pro Glu Leu Val Leu
                725                 730                 735

Val Ser Ala Gly Phe Asp Ala Ala Arg Gly Asp Pro Leu Gly Gly Cys
            740                 745                 750
```

```
Gln Val Ser Pro Glu Gly Tyr Ala His Leu Thr His Leu Leu Met Gly
            755                 760                 765

Leu Ala Ser Gly Arg Ile Ile Leu Ile Leu Glu Gly Gly Tyr Asn Leu
770                 775                 780

Thr Ser Ile Ser Glu Ser Met Ala Ala Cys Thr Arg Ser Leu Leu Gly
785                 790                 795                 800

Asp Pro Pro Leu Leu Thr Leu Pro Arg Pro Leu Ser Gly Ala
            805                 810                 815

Leu Ala Ser Ile Thr Glu Thr Ile Gln Val His Arg Arg Tyr Trp Arg
            820                 825                 830

Ser Leu Arg Val Met Lys Val Glu Asp Arg Glu Gly Pro Ser Ser Ser
            835                 840                 845

Lys Leu Val Thr Lys Lys Ala Pro Gln Pro Ala Lys Pro Arg Leu Ala
850                 855                 860

Glu Arg Met Thr Thr Arg Glu Lys Lys Val Leu Glu Ala Gly Met Gly
865                 870                 875                 880

Lys Val Thr Ser Ala Ser Phe Gly Glu Glu Ser Thr Pro Gly Gln Thr
            885                 890                 895

Asn Ser Glu Thr Ala Val Val Ala Leu Thr Gln Asp Gln Pro Ser Glu
            900                 905                 910

Ala Ala Thr Gly Gly Ala Thr Leu Ala Gln Thr Ile Ser Glu Ala Ala
            915                 920                 925

Ile Gly Gly Ala Met Leu Gly Gln Thr Thr Ser Glu Glu Ala Val Gly
            930                 935                 940

Gly Ala Thr Pro Asp Gln Thr Thr Ser Glu Glu Thr Val Gly Gly Ala
945                 950                 955                 960

Ile Leu Asp Gln Thr Thr Ser Glu Asp Ala Val Gly Gly Ala Thr Leu
            965                 970                 975

Gly Gln Thr Thr Ser Glu Glu Ala Val Gly Gly Ala Thr Leu Ala Gln
            980                 985                 990

Thr Ile Ser Glu Ala Ala Met Glu Gly Ala Thr Leu Asp Gln Thr Thr
            995                 1000                1005

Ser Glu Glu Ala Pro Gly Gly Thr Glu Leu Ile Gln Thr Pro Leu Ala
1010                1015                1020

Ser Ser Thr Asp His Gln Thr Pro Pro Thr Ser Pro Val Gln Gly Thr
1025                1030                1035                1040

Thr Pro Gln Ile Ser Pro Ser Thr Leu Ile Gly Ser Leu Arg Thr Leu
                1045                1050                1055

Glu Leu Gly Ser Glu Ser Gln Gly Ala Ser Glu Ser Gln Ala Pro Gly
                1060                1065                1070

Glu Glu Asn Leu Leu Gly Glu Ala Ala Gly Gly Gln Asp Met Ala Asp
            1075                1080                1085

Ser Met Leu Met Gln Gly Ser Arg Gly Leu Thr Asp Gln Ala Ile Phe
1090                1095                1100

Tyr Ala Val Thr Pro Leu Pro Trp Cys Pro His Leu Ala Val Cys
1105                1110                1115                1120

Pro Ile Pro Ala Ala Gly Leu Asp Val Thr Gln Pro Cys Gly Asp Cys
            1125                1130                1135

Gly Thr Ile Gln Glu Asn Trp Val Cys Leu Ser Cys Tyr Gln Val Tyr
                1140                1145                1150

Cys Gly Arg Tyr Ile Asn Gly His Met Leu Gln His His Gly Asn Ser
            1155                1160                1165

Gly His Pro Leu Val Leu Ser Tyr Ile Asp Leu Ser Ala Trp Cys Tyr
```

```
                1170                1175              1180

Tyr Cys Gln Ala Tyr Val His His Gln Ala Leu Leu Asp Val Lys Asn
1185                1190              1195              1200

Ile Ala His Gln Asn Lys Phe Gly Glu Asp Met Pro His Pro His
                1205              1210              1215

<210> SEQ ID NO 7
<211> LENGTH: 75
<212> TYPE: PRT
<213> ORGANISM: Artificial Sequence
<220> FEATURE:
<223> OTHER INFORMATION: Description of Artificial Sequence: Consensus
      sequence
<220> FEATURE:
<221> NAME/KEY: MISC_FEATURE
<222> LOCATION: (4)..(9)
<223> OTHER INFORMATION: Variable amino acid
<220> FEATURE:
<221> NAME/KEY: MISC_FEATURE
<222> LOCATION: (11)
<223> OTHER INFORMATION: Variable amino acid
<220> FEATURE:
<221> NAME/KEY: MISC_FEATURE
<222> LOCATION: (13)
<223> OTHER INFORMATION: Variable amino acid
<220> FEATURE:
<221> NAME/KEY: MISC_FEATURE
<222> LOCATION: (16)
<223> OTHER INFORMATION: Variable amino acid
<220> FEATURE:
<221> NAME/KEY: MISC_FEATURE
<222> LOCATION: (19)..(20)
<223> OTHER INFORMATION: Variable amino acid
<220> FEATURE:
<221> NAME/KEY: MISC_FEATURE
<222> LOCATION: (22)..(24)
<223> OTHER INFORMATION: Variable amino acid
<220> FEATURE:
<221> NAME/KEY: MISC_FEATURE
<222> LOCATION: (26)..(35)
<223> OTHER INFORMATION: Variable amino acid
<220> FEATURE:
<221> NAME/KEY: MISC_FEATURE
<222> LOCATION: (42)
<223> OTHER INFORMATION: Variable amino acid
<220> FEATURE:
<221> NAME/KEY: MISC_FEATURE
<222> LOCATION: (46)
<223> OTHER INFORMATION: Variable amino acid
<220> FEATURE:
<221> NAME/KEY: MISC_FEATURE
<222> LOCATION: (50)..(51)
<223> OTHER INFORMATION: Variable amino acid
<220> FEATURE:
<221> NAME/KEY: MISC_FEATURE
<222> LOCATION: (53)..(54)
<223> OTHER INFORMATION: Variable amino acid
<220> FEATURE:
<221> NAME/KEY: MISC_FEATURE
<222> LOCATION: (61)
<223> OTHER INFORMATION: Variable amino acid
<220> FEATURE:
<221> NAME/KEY: MISC_FEATURE
<222> LOCATION: (63)
<223> OTHER INFORMATION: Variable amino acid
<220> FEATURE:
<221> NAME/KEY: MISC_FEATURE
<222> LOCATION: (67)..(68)
<223> OTHER INFORMATION: Variable amino acid
<220> FEATURE:
<221> NAME/KEY: MISC_FEATURE
<222> LOCATION: (70)
<223> OTHER INFORMATION: Variable amino acid
<220> FEATURE:
<221> NAME/KEY: MISC_FEATURE
<222> LOCATION: (72)
```

<223> OTHER INFORMATION: Variable amino acid
<220> FEATURE:
<221> NAME/KEY: MISC_FEATURE
<222> LOCATION: (74)..(75)
<223> OTHER INFORMATION: Variable amino acid

<400> SEQUENCE: 7

His His Ala Xaa Xaa Xaa Xaa Xaa Gly Xaa Cys Xaa Phe Asn Xaa
1               5                   10                  15

Val Ala Xaa Xaa Ala Xaa Xaa Gln Xaa Xaa Xaa Xaa Xaa Xaa Xaa
            20                  25                  30

Xaa Xaa Xaa Leu Ile Val Asp Trp Asp Xaa His His Gly Xaa Gly Thr
        35                  40                  45

Gln Xaa Xaa Phe Xaa Xaa Asp Pro Ser Val Leu Tyr Xaa Ser Xaa His
    50                  55                  60

Arg Tyr Xaa Xaa Gly Xaa Phe Xaa Pro Xaa Xaa
65                  70                  75

<210> SEQ ID NO 8
<211> LENGTH: 73
<212> TYPE: PRT
<213> ORGANISM: Homo sapiens

<400> SEQUENCE: 8

His His Ala Glu Glu Ser Thr Pro Met Gly Phe Cys Tyr Phe Asn Ser
1               5                   10                  15

Val Ala Val Ala Ala Lys Leu Leu Gln Gln Arg Leu Ser Val Ser Lys
            20                  25                  30

Ile Leu Ile Val Asp Trp Asp Val His His Gly Asn Gly Thr Gln Gln
        35                  40                  45

Ala Phe Tyr Ser Asp Pro Ser Val Leu Tyr Met Ser Leu His Arg Tyr
    50                  55                  60

Asp Asp Gly Asn Phe Phe Pro Gly Ser
65                  70

<210> SEQ ID NO 9
<211> LENGTH: 73
<212> TYPE: PRT
<213> ORGANISM: Homo sapiens

<400> SEQUENCE: 9

His His Ala Glu Glu Ser Thr Ala Met Gly Phe Cys Phe Phe Asn Ser
1               5                   10                  15

Val Ala Ile Thr Ala Lys Leu Leu Gln Gln Lys Leu Asn Val Gly Lys
            20                  25                  30

Val Leu Ile Val Asp Trp Asp Ile His His Gly Asn Gly Thr Gln Gln
        35                  40                  45

Ala Phe Tyr Asn Asp Pro Ser Val Leu Tyr Ile Ser Leu His Arg Tyr
    50                  55                  60

Asp Asn Gly Asn Phe Phe Pro Gly Ser
65                  70

<210> SEQ ID NO 10
<211> LENGTH: 73
<212> TYPE: PRT
<213> ORGANISM: Homo sapiens

<400> SEQUENCE: 10

His His Ala Gln His Ser Leu Met Asp Gly Tyr Cys Met Phe Asn His
1               5                   10                  15

Val Ala Val Ala Ala Arg Tyr Ala Gln Gln Lys His Arg Ile Arg Arg
            20                  25                  30

Val Leu Ile Val Asp Trp Asp Val His His Gly Gln Gly Thr Gln Phe
        35                  40                  45

Thr Phe Asp Gln Asp Pro Ser Val Leu Tyr Phe Ser Ile His Arg Tyr
    50                  55                  60

Glu Gln Gly Arg Phe Trp Pro His Leu
65                  70

<210> SEQ ID NO 11
<211> LENGTH: 3121
<212> TYPE: DNA
<213> ORGANISM: Homo sapiens

<400> SEQUENCE: 11

```
ataataccta ccttgcagga ccacgacagg attaagtgag gaaaaacccc catgagagtg     60
ttttgccatt gtcaagtgag cctgaggag gctgaggggg gatcaggctg tatcatgccc    120
ccgaggacaa actttccagt ttaccctgct ccctctctct gtccctaggc tgccccaggc    180
cctgtgcaga cacaccaggc cctcagccgc agcccatgga cctgcgggtg ggccagcggc    240
ccccagtgga gcccccacca gagcccacat tgctggccct gcagcgtccc cagcgcctgc    300
accaccacct cttcctagca ggcctgcagc agcagcgctc ggtggagccc atgaggctct    360
ccatggacac gccgatgccc gagttgcagg tgggacccca ggaacaagag ctgcggcagc    420
ttctccacaa ggacaagagc aagcgaagtg ctgtagccag cagcgtggtc aagcagaagc    480
tagcggaggt gattctgaaa aaacagcagg cggccctaga aagaacagtc catcccaaca    540
gccccggcat tccctacaga accctggagc cctggagac ggaaggagcc acccgctcca    600
tgctcagcag cttttttgcct cctgttccca gcctgcccag tgaccccca gagcacttcc    660
ctctgcgcaa acagtctct gagcccaacc tgaagctgcg ctataagccc aagaagtccc    720
tggagcggag gaagaatcca ctgctccgaa aggagagtgc gccccccagc ctccggcggc    780
ggcccgcaga gaccctcgga gactcctccc caagtagtag cagcacgccc gcatcagggt    840
gcagctcccc caatgacagc gagcacggcc ccaatcccat cctgggcgac agtgaccgca    900
ggacccatcc gactctgggc cctcgggggc aatcctggg gagcccccac actcccctct    960
tcctgcccca tggcttggag cccgaggctg ggggcaccct gccctctcgc ctgcagccca   1020
ttctcctcct ggacccctca ggctctcatg ccccgctgct gactgtgccc gggcttgggc   1080
ccttgccctt ccactttgcc cagtccttaa tgaccaccga gcggctctct gggtcaggcc   1140
tccactggcc actgagccgg actcgctcag agccctgcc ccccagtgcc accgctcccc   1200
caccgccggg cccatgcag ccccgcctgg agcagctcaa aactcacgtc caggtgatca   1260
agaggtcagc caagccgagt gagaagcccc ggctgcggca gatacccctcg gctgaagacc   1320
tggagacaga tggcggggga ccgggccagg tggtggacga tggcctggag cacagggagc   1380
tgggccatgg gcagcctgag gccagaggcc ccgctcctct ccagcagcac cctcaggtgt   1440
tgctctggga acagcagcga ctggctgggc ggctcccccg gggcagcacc ggggacactg   1500
tgctgcttcc tctggcccag ggtgggcacc ggcctctgtc ccgggctcag tcttccccag   1560
ccgcacctgc ctcactgtca gcccagagc ctgccagcca ggcccgagtc ctctccagct   1620
cagagaccct gccaggacc ctgcccttca ccacagggct gatctatgac tcggtcatgc   1680
tgaagcacca gtgctcctgc ggtgacaaca gcaggcaccc ggagcacgcc ggccgcatcc   1740
```

```
agagcatctg gtcccggctg caggagcggg ggctccggag ccagtgtgag tgtctccgag    1800
gccggaaggc ctccctggaa gagctgcagt cggtccactc tgagcggcac gtgctcctct    1860
acggcaccaa cccgctcagc cgcctcaaac tggacaacgg gaagctggca gggctcctgg    1920
cacagcggat gtttgtgatg ctgccctgtg gtggggttgg ggtggacact gacaccatct    1980
ggaatgagct tcattcctcc aatgcagccc gctgggccgc tggcagtgtc actgacctcg    2040
ccttcaaagt ggcttctcgt gagctaaaga atggtttcgc tgtggtgcgg ccccaggac     2100
accatgcaga tcattcaaca gccatgggct tctgcttctt caactcagtg ccatcgcct     2160
gccggcagct gcaacagcag agcaaggcca gcaagatcct cattgtagac tgggacgtgc    2220
accatggcaa cggcacccag caaaccttct accaagaccc cagtgtgctc tacatctccc    2280
tgcatcgcca tgacgacggc aacttcttcc cggggagtgg ggctgtggat gaggtagggg    2340
ctggcagcgg tgagggcttc aatgtcaatg tggcctgggc tggaggtctg gacccccccca   2400
tgggggatcc tgagtacctg gctgctttca ggatagtcgt gatgcccatc gcccgagagt    2460
tctctccaga cctagtcctg gtgtctgctg gatttgatgc tgctgagggt cacccggccc    2520
cactgggtgg ctaccatgtt tctgccaaat gttttggata catgacgcag caactgatga    2580
acctggcagg aggcgcagtg gtgctggcct tggagggtgg ccatgacctc acagccatct    2640
gtgacgcctc tgaggcctgt gtggctgctc ttctgggtaa cagggtggat ccccttttcag   2700
aagaaggctg gaaacagaaa cccaacctca atgccatccg ctctctggag gccgtgatcc    2760
gggtgcacag taaatactgg ggctgcatgc agcgcctggc ctcctgtcca gactcctggg    2820
tgcctagagt gccaggggct gacaaagaag aagtggaggc agtgaccgca ctggcgtccc    2880
tctctgtggg catcctggct gaagataggc cctcggagca gctggtggag gaggaagaac    2940
ctatgaatct ctaaggctct ggaaccatct gcccgcccac catgcccttg ggacctggtt    3000
ctcttctaac ccctggcaat agcccccatt cctgggtctt tagagatcct gtgggcaagt    3060
agttggaacc agagaacagc ctgcctgctt tgacagttat cccagggagc gtgagaaaat    3120
c                                                                   3121
```

<210> SEQ ID NO 12
<211> LENGTH: 912
<212> TYPE: PRT
<213> ORGANISM: Homo sapiens

<400> SEQUENCE: 12

```
Met Asp Leu Arg Val Gly Gln Arg Pro Val Glu Pro Pro Glu
  1               5                  10                  15

Pro Thr Leu Leu Ala Leu Gln Arg Pro Gln Arg Leu His His Leu
                 20                  25                  30

Phe Leu Ala Gly Leu Gln Gln Arg Ser Val Glu Pro Met Arg Leu
         35                  40                  45

Ser Met Asp Thr Pro Met Pro Glu Leu Gln Val Gly Pro Gln Glu Gln
     50                  55                  60

Glu Leu Arg Gln Leu Leu His Lys Asp Lys Ser Lys Arg Ser Ala Val
 65                  70                  75                  80

Ala Ser Ser Val Val Lys Gln Lys Leu Ala Glu Val Ile Leu Lys Lys
                 85                  90                  95

Gln Gln Ala Ala Leu Glu Arg Thr Val His Pro Asn Ser Pro Gly Ile
            100                 105                 110

Pro Tyr Arg Thr Leu Glu Pro Leu Glu Thr Glu Gly Ala Thr Arg Ser
        115                 120                 125
```

-continued

```
Met Leu Ser Ser Phe Leu Pro Pro Val Pro Ser Leu Pro Ser Asp Pro
    130                 135                 140
Pro Glu His Phe Pro Leu Arg Lys Thr Val Ser Glu Pro Asn Leu Lys
145                 150                 155                 160
Leu Arg Tyr Lys Pro Lys Lys Ser Leu Glu Arg Arg Lys Asn Pro Leu
                165                 170                 175
Leu Arg Lys Glu Ser Ala Pro Pro Ser Leu Arg Arg Pro Ala Glu
            180                 185                 190
Thr Leu Gly Asp Ser Ser Pro Ser Ser Ser Thr Pro Ala Ser Gly
        195                 200                 205
Cys Ser Ser Pro Asn Asp Ser Glu His Gly Pro Asn Pro Ile Leu Gly
    210                 215                 220
Asp Ser Asp Arg Arg Thr His Pro Thr Leu Gly Pro Arg Gly Pro Ile
225                 230                 235                 240
Leu Gly Ser Pro His Thr Pro Leu Phe Leu Pro His Gly Leu Glu Pro
                245                 250                 255
Glu Ala Gly Gly Thr Leu Pro Ser Arg Leu Gln Pro Ile Leu Leu Leu
            260                 265                 270
Asp Pro Ser Gly Ser His Ala Pro Leu Leu Thr Val Pro Gly Leu Gly
        275                 280                 285
Pro Leu Pro Phe His Phe Ala Gln Ser Leu Met Thr Thr Glu Arg Leu
    290                 295                 300
Ser Gly Ser Gly Leu His Trp Pro Leu Ser Arg Thr Arg Ser Glu Pro
305                 310                 315                 320
Leu Pro Pro Ser Ala Thr Ala Pro Pro Gly Pro Met Gln Pro
                325                 330                 335
Arg Leu Glu Gln Leu Lys Thr His Val Gln Val Ile Lys Arg Ser Ala
            340                 345                 350
Lys Pro Ser Glu Lys Pro Arg Leu Arg Gln Ile Pro Ser Ala Glu Asp
        355                 360                 365
Leu Glu Thr Asp Gly Gly Pro Gly Gln Val Val Asp Asp Gly Leu
    370                 375                 380
Glu His Arg Glu Leu Gly His Gly Gln Pro Glu Ala Arg Gly Pro Ala
385                 390                 395                 400
Pro Leu Gln Gln His Pro Gln Val Leu Leu Trp Glu Gln Gln Arg Leu
                405                 410                 415
Ala Gly Arg Leu Pro Arg Gly Ser Thr Gly Asp Thr Val Leu Leu Pro
            420                 425                 430
Leu Ala Gln Gly Gly His Arg Pro Leu Ser Arg Ala Gln Ser Ser Pro
        435                 440                 445
Ala Ala Pro Ala Ser Leu Ser Ala Pro Glu Pro Ala Ser Gln Ala Arg
    450                 455                 460
Val Leu Ser Ser Glu Thr Pro Ala Arg Thr Leu Pro Phe Thr Thr
465                 470                 475                 480
Gly Leu Ile Tyr Asp Ser Val Met Leu Lys His Gln Cys Ser Cys Gly
                485                 490                 495
Asp Asn Ser Arg His Pro Glu His Ala Gly Arg Ile Gln Ser Ile Trp
            500                 505                 510
Ser Arg Leu Gln Glu Arg Gly Leu Arg Ser Gln Cys Glu Cys Leu Arg
        515                 520                 525
Gly Arg Lys Ala Ser Leu Glu Glu Leu Gln Ser Val His Ser Glu Arg
    530                 535                 540
```

His Val Leu Leu Tyr Gly Thr Asn Pro Leu Ser Arg Leu Lys Leu Asp
545                 550                 555                 560

Asn Gly Lys Leu Ala Gly Leu Leu Ala Gln Arg Met Phe Val Met Leu
            565                 570                 575

Pro Cys Gly Gly Val Gly Val Asp Thr Asp Thr Ile Trp Asn Glu Leu
            580                 585                 590

His Ser Ser Asn Ala Ala Arg Trp Ala Ala Gly Ser Val Thr Asp Leu
            595                 600                 605

Ala Phe Lys Val Ala Ser Arg Glu Leu Lys Asn Gly Phe Ala Val Val
            610                 615                 620

Arg Pro Pro Gly His His Ala Asp His Ser Thr Ala Met Gly Phe Cys
625                 630                 635                 640

Phe Phe Asn Ser Val Ala Ile Ala Cys Arg Gln Leu Gln Gln Gln Ser
                645                 650                 655

Lys Ala Ser Lys Ile Leu Ile Val Asp Trp Asp Val His His Gly Asn
            660                 665                 670

Gly Thr Gln Gln Thr Phe Tyr Gln Asp Pro Ser Val Leu Tyr Ile Ser
            675                 680                 685

Leu His Arg His Asp Asp Gly Asn Phe Phe Pro Gly Ser Gly Ala Val
690                 695                 700

Asp Glu Val Gly Ala Gly Ser Gly Glu Gly Phe Asn Val Asn Val Ala
705                 710                 715                 720

Trp Ala Gly Gly Leu Asp Pro Pro Met Gly Asp Pro Glu Tyr Leu Ala
                725                 730                 735

Ala Phe Arg Ile Val Val Met Pro Ile Ala Arg Glu Phe Ser Pro Asp
            740                 745                 750

Leu Val Leu Val Ser Ala Gly Phe Asp Ala Ala Glu Gly His Pro Ala
            755                 760                 765

Pro Leu Gly Gly Tyr His Val Ser Ala Lys Cys Phe Gly Tyr Met Thr
            770                 775                 780

Gln Gln Leu Met Asn Leu Ala Gly Gly Ala Val Val Leu Ala Leu Glu
785                 790                 795                 800

Gly Gly His Asp Leu Thr Ala Ile Cys Asp Ala Ser Glu Ala Cys Val
                805                 810                 815

Ala Ala Leu Leu Gly Asn Arg Val Asp Pro Leu Ser Glu Glu Gly Trp
            820                 825                 830

Lys Gln Lys Pro Asn Leu Asn Ala Ile Arg Ser Leu Glu Ala Val Ile
            835                 840                 845

Arg Val His Ser Lys Tyr Trp Gly Cys Met Gln Arg Leu Ala Ser Cys
850                 855                 860

Pro Asp Ser Trp Val Pro Arg Val Pro Gly Ala Asp Lys Glu Glu Val
865                 870                 875                 880

Glu Ala Val Thr Ala Leu Ala Ser Leu Ser Val Gly Ile Leu Ala Glu
                885                 890                 895

Asp Arg Pro Ser Glu Gln Leu Val Glu Glu Glu Pro Met Asn Leu
            900                 905                 910

<210> SEQ ID NO 13
<211> LENGTH: 4178
<212> TYPE: DNA
<213> ORGANISM: Homo sapiens

<400> SEQUENCE: 13
ggggaagaga ggcacagaca cagataggag aagggcaccg gctggagcca cttgcaggac    60

```
tgagggtttt tgcaacaaaa ccctagcagc ctgaagaact ctaagccaga tggggtggct      120
ggacgagagc agctcttggc tcagcaaaga atgcacagta tgatcagctc agtggatgtg      180
aagtcagaag ttcctgtggg cctggagccc atctcacctt tagacctaag gacagacctc      240
aggatgatga tgcccgtggt ggaccctgtt gtccgtgaga agcaattgca gcaggaatta      300
cttcttatcc agcagcagca acaaatccag aagcagcttc tgatagcaga gtttcagaaa      360
cagcatgaga acttgacacg gcagcaccag gctcagcttc aggagcatat caaggaactt      420
ctagccataa aacagcaaca agaactccta gaaaaggagc agaaactgga gcagcagagg      480
caagaacagg aagtagagag gcatcgcaga gaacagcagc ttcctcctct cagaggcaaa      540
gatagaggac gagaaagggc agtggcaagt acagaagtaa agcagaagct tcaagagttc      600
ctactgagta aatcagcaac gaaagacact ccaactaatg gaaaaaatca ttccgtgagc      660
cgccatccca agctctggta cacggctgcc caccacacat cattggatca aagctctcca      720 cccttagtg aacatctcc atcctacaag tacacattac caggagcaca agatgcaaag       780
gatgatttcc cccttcgaaa aactgcctct gagcccaact tgaaggtgcg gtccaggtta      840
aaacagaaag tggcagagag gagaagcagc cccttactca ggcggaagga tggaaatgtt      900
gtcacttcat tcaagaagcg aatgtttgag gtgacagaat cctcagtcag tagcagttct      960
ccaggctctg gtcccagttc accaaacaat gggccaactg gaagtgttac tgaaaatgag     1020
acttcggttt tgcccctac ccctcatgcc gagcaaatgg tttcacagca acgcattcta      1080
attcatgaag attccatgaa cctgctaagt ctttatacct ctccttcttt gcccaacatt     1140
accttggggc ttcccgcagt gccatcccag ctcaatgctt cgaattcact caaagaaaag     1200
cagaagtgtg agacgcagac gcttaggcaa ggtgttcctc tgcctgggca gtatggaggc     1260
agccaccagg ctctcctgca gcatttatta ttgaaagaac aaatgcgaca gcaaaagctt     1320
cttgtagctg gtggagttcc cttacatcct cagtctccct tggcaacaaa agagagaatt     1380
tcacctggca ttagaggtac ccacaaattg ccccgtcaca gaccccctgaa ccgaacccag     1440 tctgcacctt tgcctcagag cacgttggct cagctggtca ttcaacagca acaccagcaa     1500
ttcttggaga agcagaagca ataccagcag cagatccaca tgaacaaaact gctttcgaaa     1560 tctattgaac aactgaagca accaggcagt caccttgagg aagcagagga agagcttcag     1620 gggaccagg cgatgcagga agacagagcg ccctctagtg gcaacagcac taggagcgac     1680
agcagtgctt gtgtggatga cacactggga caagttgggg ctgtgaaggt caaggaggaa     1740
ccagtggaca gtgatgaaga tgctcagatc caggaaatgg aatctgggga gcaggctgct     1800
tttatgcaac aggtaatagg caaagattta gctccaggat ttgtaattaa agtcattatc     1860
tgaacatgaa atgcattgca ggtttggtaa atggatatga tttcctatca gtttatattt     1920
ctctatgatt tgagttcagt gtttaaggat tctacctaat gcagatatat gtatatatct     1980
atatagaggt ctttctatat actgatctct atatagatat caatgtttca ttgaaaatcc     2040
actggtaagg aaatacctgt tatactaaaa ttatgataca taatatctga gcagttaata     2100
ggctttaaat ttatcccaaa gcctgctaca ccaattactt ctaaagaaaa caaattcact     2160
gttattttga gttatgtgt tgagatcagt gactgctgga tagtctccca gtctgatcaa      2220
tgaagcattc gattagtttt tgattttttg caacatctag aatttaattt tcacatcact     2280
gtacataatg tatcatacta tagtcttgaa cactgttaaa ggtagtctgc cccttccttc     2340
ctctctcttt ttttagttaa gtagaaatgt tctggtcacc atgccagtag tcctaggtta     2400
ttgtgtaggt tgcaattgaa catattagga atacaggtgg ttttaaatat atagatgcaa     2460
```

```
attgcagcac tactttaaat attagattat gtctcacata gcactgctca ttttactttt    2520
attttgtgta atttgatgac actgtctatc aaaaaagagc aaatgaagca gatgcaaatg    2580
ttagtgagaa gtaatgtgca gcattatggt ccaatcagat acaatattgt gtctacaatt    2640
gcaaaaaaca cagtaacagg atgaatatta tctgatatca agtcaaaatc agtttgaaaa    2700
gaaggtgtat catattttat attgtcacta gaatctctta agtataattc cataatgaca    2760
tgggcatata ccgtaacatt ctggcaaata acaattagaa aagataggtt taacaaaaaa    2820
atttacttgt atataatgca ccttcaggag gactatgtcc tttgatgcta taaaatacaa    2880
acaactttga aggcaacaga agacactgtt tattcaagtc agttctttgt caggttcctg    2940
ctgttctcct acagaaaagt gattctgtga gggtgaacag gaaatgcctt gtggaaacag    3000
gaagtccaag tgattcatgt actgaggaat gtaggaaaaa aaatctgagg atagtgcttt    3060
actctttctg tttttaaagg gcactctatg aattgattta ttgtctaaga aaataacacc    3120
acaagtaggg aaattgttac ggaagctttt cactggaaca tttccttcat attccctttt    3180
gatatgttta ccttgtttta taggtttact tttgttaagc tagttaaagg ttcgttgtat    3240
taagacccct ttaatatgga taatccaaat tgacctagaa tctttgtgag gttttttcta    3300
ttaaaatatt tatatttcta aatccgaggt atttcaaggt gtagtatcct atttcaaagg    3360
agatatagca gttttgccaa atgtagacat tgttcaactg tatgttattg gcacgtgttg    3420
tttacatttt gctgtgacat ttaaaaatat ttctttaaaa atgttactgc taaagataca    3480
ttatcctttt ttaaaaagtc tccattcaaa ttaaattaac ataactagaa gttagaaagt    3540
ttaaaagttt tccacataat gaaagtcctt ctgataattt gacaaatagc tataatagga    3600
acactcccta tcaccaacat attttggtta gtatattcct tcatattaaa atgacttttt    3660
gtcagttgtt ttgcattaaa aatatggcat gcctaagata aaattgtata tttttccat    3720 ctcataaata ttcattttct tcaaagtctt ttttcaatct cataaaaaag ggatagtgca    3780
tcttttaaaa tacattttat ttggggagga acatgtggct gagcagactt ttgtataata    3840
ttacttcaaa gatatgtaat cacaaacaaa aaaaactatt ttttataatg tcatttgaga    3900
gagtttcatc agtacagttg gtggacgtta attgtttgaa tttgatagtc tttgaattta    3960
atcaagaaac tacctggaac cagtgaaaag gaaagctgga cttaaataat cttagaatta    4020
attgataaat gtctctttta aaatctactg tatttattat aatttacacc cttgaaggtg    4080
atctcttgtt ttgtgttgta aatatattgt ttgtatgttt cccttcttgc cttctgttat    4140
aagtctcttc ctttctcaaa taagtttttt tttaaaag                           4178
```

<210> SEQ ID NO 14
<211> LENGTH: 590
<212> TYPE: PRT
<213> ORGANISM: Homo sapiens

<400> SEQUENCE: 14

Met His Ser Met Ile Ser Ser Val Asp Val Lys Ser Glu Val Pro Val
1               5                   10                  15

Gly Leu Glu Pro Ile Ser Pro Leu Asp Leu Arg Thr Asp Leu Arg Met
            20                  25                  30

Met Met Pro Val Val Asp Pro Val Val Arg Glu Lys Gln Leu Gln Gln
        35                  40                  45

Glu Leu Leu Leu Ile Gln Gln Gln Gln Ile Gln Lys Gln Leu Leu
    50                  55                  60

```
Ile Ala Glu Phe Gln Lys Gln His Glu Asn Leu Thr Arg Gln His Gln
 65                  70                  75                  80

Ala Gln Leu Gln Glu His Ile Lys Glu Leu Leu Ala Ile Lys Gln Gln
                 85                  90                  95

Gln Glu Leu Leu Glu Lys Glu Gln Lys Leu Glu Gln Gln Arg Gln Glu
            100                 105                 110

Gln Glu Val Glu Arg His Arg Arg Glu Gln Gln Leu Pro Pro Leu Arg
            115                 120                 125

Gly Lys Asp Arg Gly Arg Glu Arg Ala Val Ala Ser Thr Glu Val Lys
        130                 135                 140

Gln Lys Leu Gln Glu Phe Leu Leu Ser Lys Ser Ala Thr Lys Asp Thr
145                 150                 155                 160

Pro Thr Asn Gly Lys Asn His Ser Val Ser Arg His Pro Lys Leu Trp
                165                 170                 175

Tyr Thr Ala Ala His His Thr Ser Leu Asp Gln Ser Ser Pro Pro Leu
                180                 185                 190

Ser Gly Thr Ser Pro Ser Tyr Lys Tyr Thr Leu Pro Gly Ala Gln Asp
            195                 200                 205

Ala Lys Asp Asp Phe Pro Leu Arg Lys Thr Ala Ser Glu Pro Asn Leu
        210                 215                 220

Lys Val Arg Ser Arg Leu Lys Gln Lys Val Ala Glu Arg Arg Ser Ser
225                 230                 235                 240

Pro Leu Leu Arg Arg Lys Asp Gly Asn Val Val Thr Ser Phe Lys Lys
                245                 250                 255

Arg Met Phe Glu Val Thr Glu Ser Ser Val Ser Ser Ser Ser Pro Gly
            260                 265                 270

Ser Gly Pro Ser Ser Pro Asn Asn Gly Pro Thr Gly Ser Val Thr Glu
            275                 280                 285

Asn Glu Thr Ser Val Leu Pro Pro Thr Pro His Ala Glu Gln Met Val
        290                 295                 300

Ser Gln Gln Arg Ile Leu Ile His Glu Asp Ser Met Asn Leu Leu Ser
305                 310                 315                 320

Leu Tyr Thr Ser Pro Ser Leu Pro Asn Ile Thr Leu Gly Leu Pro Ala
                325                 330                 335

Val Pro Ser Gln Leu Asn Ala Ser Asn Ser Leu Lys Glu Lys Gln Lys
            340                 345                 350

Cys Glu Thr Gln Thr Leu Arg Gln Gly Val Pro Leu Pro Gly Gln Tyr
            355                 360                 365

Gly Gly Ser Ile Pro Ala Ser Ser Ser His Pro His Val Thr Leu Glu
        370                 375                 380

Gly Lys Pro Pro Asn Ser Ser His Gln Ala Leu Leu Gln His Leu Leu
385                 390                 395                 400

Leu Lys Glu Gln Met Arg Gln Gln Lys Leu Leu Val Ala Gly Gly Val
                405                 410                 415

Pro Leu His Pro Gln Ser Pro Leu Ala Thr Lys Glu Arg Ile Ser Pro
            420                 425                 430

Gly Ile Arg Gly Thr His Lys Leu Pro Arg His Arg Pro Leu Asn Arg
        435                 440                 445

Thr Gln Ser Ala Pro Leu Pro Gln Ser Thr Leu Ala Gln Leu Val Ile
        450                 455                 460

Gln Gln Gln His Gln Gln Phe Leu Glu Lys Gln Lys Gln Tyr Gln Gln
465                 470                 475                 480

Gln Ile His Met Asn Lys Leu Leu Ser Lys Ser Ile Glu Gln Leu Lys
```

```
                    485                 490                 495
Gln Pro Gly Ser His Leu Glu Glu Ala Glu Glu Leu Gln Gly Asp
                500                 505                 510
Gln Ala Met Gln Glu Asp Arg Ala Pro Ser Ser Gly Asn Ser Thr Arg
            515                 520                 525
Ser Asp Ser Ser Ala Cys Val Asp Asp Thr Leu Gln Val Gly Ala
530                 535                 540
Val Lys Val Lys Glu Glu Pro Val Asp Ser Asp Glu Asp Ala Gln Ile
545                 550                 555                 560
Gln Glu Met Glu Ser Gly Glu Gln Ala Ala Phe Met Gln Gln Val Ile
                565                 570                 575
Gly Lys Asp Leu Ala Pro Gly Phe Val Ile Lys Val Ile Ile
                580                 585                 590

<210> SEQ ID NO 15
<211> LENGTH: 69
<212> TYPE: PRT
<213> ORGANISM: Homo sapiens

<400> SEQUENCE: 15

His His Ala Lys Lys Ser Glu Ala Ser Gly Phe Cys Tyr Val Asn Asp
  1               5                   10                  15
Ile Val Leu Ala Ile Leu Glu Leu Leu Lys Tyr His Gln Arg Val Leu
                20                  25                  30
Tyr Ile Asp Ile Asp Ile His His Gly Asp Gly Val Glu Glu Ala Phe
            35                  40                  45
Tyr Thr Thr Asp Arg Val Met Thr Val Ser Phe His Lys Tyr Gly Glu
        50                  55                  60
Tyr Phe Pro Gly Thr
 65

<210> SEQ ID NO 16
<211> LENGTH: 75
<212> TYPE: PRT
<213> ORGANISM: Saccharomyces sp.

<400> SEQUENCE: 16

His His Ala Glu Pro Gln Ala Ala Gly Gly Phe Cys Leu Phe Ser Asn
  1               5                   10                  15
Val Ala Val Ala Ala Lys Asn Ile Leu Lys Asn Tyr Pro Glu Ser Val
                20                  25                  30
Arg Arg Ile Met Ile Leu Asp Trp Asp Ile His His Gly Asn Gly Thr
            35                  40                  45
Gln Lys Ser Phe Tyr Gln Asp Asp Gln Val Leu Tyr Val Ser Leu His
        50                  55                  60
Arg Phe Glu Met Gly Lys Tyr Tyr Pro Gly Thr
 65                  70                  75

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Consensus
      sequence
<220> FEATURE:
<221> NAME/KEY: MISC_FEATURE
<222> LOCATION: (2)..(3)
<223> OTHER INFORMATION: Any amino acid
<220> FEATURE:
```

```
<221> NAME/KEY: MISC_FEATURE
<222> LOCATION: (6)
<223> OTHER INFORMATION: Any amino acid

<400> SEQUENCE: 17

Asn Xaa Xaa Gly Gly Xaa His His Ala
 1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Consensus
      sequence

<400> SEQUENCE: 18

Arg Pro Pro Gly His His Ala
 1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Consensus
      sequence
<220> FEATURE:
<221> NAME/KEY: MISC_FEATURE
<222> LOCATION: (3)
<223> OTHER INFORMATION: Phe or Tyr
<220> FEATURE:
<221> NAME/KEY: MISC_FEATURE
<222> LOCATION: (5)..(6)
<223> OTHER INFORMATION: Any amino acid

<400> SEQUENCE: 19

Ser Gly Xaa Cys Xaa Xaa Asn
 1               5

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Consensus
      sequence
<220> FEATURE:
<221> NAME/KEY: MISC_FEATURE
<222> LOCATION: (2)
<223> OTHER INFORMATION: Hydrophobic amino acid
<220> FEATURE:
<221> NAME/KEY: MISC_FEATURE
<222> LOCATION: (4)
<223> OTHER INFORMATION: Hydrophobic amino acid
<220> FEATURE:
<221> NAME/KEY: MISC_FEATURE
<222> LOCATION: (11)
<223> OTHER INFORMATION: Gln or Glu

<400> SEQUENCE: 20

Asp Xaa Asp Xaa His His Gly Asp Gly Val Xaa
 1               5                   10

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Consensus
      sequence
```

```
<220> FEATURE:
<221> NAME/KEY: MISC_FEATURE
<222> LOCATION: (2)
<223> OTHER INFORMATION: Hydrophobic amino acid
<220> FEATURE:
<221> NAME/KEY: MISC_FEATURE
<222> LOCATION: (4)
<223> OTHER INFORMATION: Hydrophobic amino acid
<220> FEATURE:
<221> NAME/KEY: MISC_FEATURE
<222> LOCATION: (8)
<223> OTHER INFORMATION: Any amino acid

<400> SEQUENCE: 21

Asp Xaa Asp Xaa His His Gly Xaa Gly Thr Gln
  1               5                  10

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Consensus
      sequence
<220> FEATURE:
<221> NAME/KEY: MISC_FEATURE
<222> LOCATION: (2)
<223> OTHER INFORMATION: Any amino acid
<220> FEATURE:
<221> NAME/KEY: MISC_FEATURE
<222> LOCATION: (4)
<223> OTHER INFORMATION: Any amino acid

<400> SEQUENCE: 22

Val Xaa Thr Xaa Ser His
  1               5

<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence: Consensus
      sequence
<220> FEATURE:
<221> NAME/KEY: MISC_FEATURE
<222> LOCATION: (2)
<223> OTHER INFORMATION: Hydrophobic amino acid
<220> FEATURE:
<221> NAME/KEY: MISC_FEATURE
<222> LOCATION: (4)
<223> OTHER INFORMATION: Met or Leu
<220> FEATURE:
<221> NAME/KEY: MISC_FEATURE
<222> LOCATION: (5)
<223> OTHER INFORMATION: Any amino acid
<220> FEATURE:
<221> NAME/KEY: MISC_FEATURE
<222> LOCATION: (11)
<223> OTHER INFORMATION: Any amino acid
<220> FEATURE:
<221> NAME/KEY: MISC_FEATURE
<222> LOCATION: (12)
<223> OTHER INFORMATION: Ser or Thr

<400> SEQUENCE: 23

Asn Xaa Pro Xaa Xaa Asp Gly Ile Asp Asp Xaa Xaa Tyr
  1               5                  10

<210> SEQ ID NO 24
<211> LENGTH: 6
<212> TYPE: PRT
<213> ORGANISM: Artificial Sequence
```

```
<220> FEATURE:
<223> OTHER INFORMATION: Description of Artificial Sequence: Consensus
      sequence
<220> FEATURE:
<221> NAME/KEY: MISC_FEATURE
<222> LOCATION: (1)
<223> OTHER INFORMATION: Hydrophobic amino acid

<400> SEQUENCE: 24

Xaa Gly Gly Gly Gly Tyr
 1               5

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Consensus
      sequence
<220> FEATURE:
<221> NAME/KEY: MISC_FEATURE
<222> LOCATION: (2)
<223> OTHER INFORMATION: Hydrophobic amino acid

<400> SEQUENCE: 25

Asn Xaa Pro Leu Lys His Gly Cys Asp Asp Asn Tyr
 1               5                  10

<210> SEQ ID NO 26
<211> LENGTH: 6
<212> TYPE: PRT
<213> ORGANISM: Homo sapiens

<400> SEQUENCE: 26

Gly Gly Tyr Glu Asn Pro
 1               5

<210> SEQ ID NO 27
<211> LENGTH: 5
<212> TYPE: PRT
<213> ORGANISM: Homo sapiens

<400> SEQUENCE: 27

Gly Glu Asp Cys Pro
 1               5

<210> SEQ ID NO 28
<211> LENGTH: 5
<212> TYPE: PRT
<213> ORGANISM: Homo sapiens

<400> SEQUENCE: 28

Gly Glu Asp Cys Pro
 1               5

<210> SEQ ID NO 29
<211> LENGTH: 5
<212> TYPE: PRT
<213> ORGANISM: Homo sapiens

<400> SEQUENCE: 29

Gly Asp Asp Cys Pro
 1               5

<210> SEQ ID NO 30
<211> LENGTH: 5
<212> TYPE: PRT
```

```
<213> ORGANISM: Homo sapiens

<400> SEQUENCE: 30

Gly Tyr Asp Cys Pro
 1               5

<210> SEQ ID NO 31
<211> LENGTH: 6
<212> TYPE: PRT
<213> ORGANISM: Homo sapiens

<400> SEQUENCE: 31

Gly Val Asp Ser Asp Thr
 1               5

<210> SEQ ID NO 32
<211> LENGTH: 6
<212> TYPE: PRT
<213> ORGANISM: Homo sapiens

<400> SEQUENCE: 32

Gly Val Asp Ser Asp Thr
 1               5

<210> SEQ ID NO 33
<211> LENGTH: 6
<212> TYPE: PRT
<213> ORGANISM: Homo sapiens

<400> SEQUENCE: 33

Gly Val Asp Thr Asp Thr
 1               5

<210> SEQ ID NO 34
<211> LENGTH: 5
<212> TYPE: PRT
<213> ORGANISM: Homo sapiens

<400> SEQUENCE: 34

Glu Tyr Ala Phe Pro
 1               5

<210> SEQ ID NO 35
<211> LENGTH: 4
<212> TYPE: PRT
<213> ORGANISM: Homo sapiens

<400> SEQUENCE: 35

Glu Tyr Phe Pro
 1

<210> SEQ ID NO 36
<211> LENGTH: 4
<212> TYPE: PRT
<213> ORGANISM: Homo sapiens

<400> SEQUENCE: 36

Glu Tyr Phe Pro
 1

<210> SEQ ID NO 37
<211> LENGTH: 5
<212> TYPE: PRT
<213> ORGANISM: Homo sapiens
```

```
<400> SEQUENCE: 37

Asn Tyr Phe Phe Pro
 1               5

<210> SEQ ID NO 38
<211> LENGTH: 5
<212> TYPE: PRT
<213> ORGANISM: Homo sapiens

<400> SEQUENCE: 38

Pro Gly Phe Phe Pro
 1               5

<210> SEQ ID NO 39
<211> LENGTH: 6
<212> TYPE: PRT
<213> ORGANISM: Homo sapiens

<400> SEQUENCE: 39

Asp Gly Asn Phe Phe Pro
 1               5

<210> SEQ ID NO 40
<211> LENGTH: 6
<212> TYPE: PRT
<213> ORGANISM: Homo sapiens

<400> SEQUENCE: 40

Asn Gly Asn Phe Phe Pro
 1               5

<210> SEQ ID NO 41
<211> LENGTH: 6
<212> TYPE: PRT
<213> ORGANISM: Homo sapiens

<400> SEQUENCE: 41

Gln Gly Arg Phe Trp Pro
 1               5

<210> SEQ ID NO 42
<211> LENGTH: 6
<212> TYPE: PRT
<213> ORGANISM: Homo sapiens

<400> SEQUENCE: 42

His Gly Thr Phe Phe Pro
 1               5

<210> SEQ ID NO 43
<211> LENGTH: 6
<212> TYPE: PRT
<213> ORGANISM: Homo sapiens

<400> SEQUENCE: 43

Asp Gly Asn Phe Phe Pro
 1               5

<210> SEQ ID NO 44
<211> LENGTH: 8
<212> TYPE: PRT
<213> ORGANISM: Homo sapiens

<400> SEQUENCE: 44
```

```
Pro Ala Gly Gly Asn His His Ala
  1               5

<210> SEQ ID NO 45
<211> LENGTH: 8
<212> TYPE: PRT
<213> ORGANISM: Homo sapiens

<400> SEQUENCE: 45

Trp Ala Gly Gly Leu His His Ala
  1               5

<210> SEQ ID NO 46
<211> LENGTH: 8
<212> TYPE: PRT
<213> ORGANISM: Homo sapiens

<400> SEQUENCE: 46

Trp Ala Gly Gly Leu His His Ala
  1               5

<210> SEQ ID NO 47
<211> LENGTH: 8
<212> TYPE: PRT
<213> ORGANISM: Homo sapiens

<400> SEQUENCE: 47

Trp Ala Gly Gly Leu His His Ala
  1               5

<210> SEQ ID NO 48
<211> LENGTH: 8
<212> TYPE: PRT
<213> ORGANISM: Homo sapiens

<400> SEQUENCE: 48

Trp Ser Gly Gly Trp His His Ala
  1               5

<210> SEQ ID NO 49
<211> LENGTH: 7
<212> TYPE: PRT
<213> ORGANISM: Homo sapiens

<400> SEQUENCE: 49

Arg Pro Pro Gly His His Ala
  1               5

<210> SEQ ID NO 50
<211> LENGTH: 7
<212> TYPE: PRT
<213> ORGANISM: Homo sapiens

<400> SEQUENCE: 50

Arg Pro Pro Gly His His Ala
  1               5

<210> SEQ ID NO 51
<211> LENGTH: 7
<212> TYPE: PRT
<213> ORGANISM: Homo sapiens

<400> SEQUENCE: 51

Arg Pro Pro Gly His His Ala
  1               5
```

```
<210> SEQ ID NO 52
<211> LENGTH: 7
<212> TYPE: PRT
<213> ORGANISM: Homo sapiens

<400> SEQUENCE: 52

Arg Pro Pro Gly His His Ala
 1               5

<210> SEQ ID NO 53
<211> LENGTH: 7
<212> TYPE: PRT
<213> ORGANISM: Homo sapiens

<400> SEQUENCE: 53

Arg Pro Pro Gly His His Ala
 1               5

<210> SEQ ID NO 54
<211> LENGTH: 10
<212> TYPE: PRT
<213> ORGANISM: Homo sapiens

<400> SEQUENCE: 54

Tyr Ile Asp Leu Asp Ala His His Cys Asp
 1               5                  10

<210> SEQ ID NO 55
<211> LENGTH: 10
<212> TYPE: PRT
<213> ORGANISM: Homo sapiens

<400> SEQUENCE: 55

Tyr Ile Asp Ile Asp Ile His His Gly Asp
 1               5                  10

<210> SEQ ID NO 56
<211> LENGTH: 10
<212> TYPE: PRT
<213> ORGANISM: Homo sapiens

<400> SEQUENCE: 56

Tyr Ile Asp Ile Asp Ile His His Gly Asp
 1               5                  10

<210> SEQ ID NO 57
<211> LENGTH: 10
<212> TYPE: PRT
<213> ORGANISM: Homo sapiens

<400> SEQUENCE: 57

Tyr Ile Asp Ile Asp Ile His His Gly Asp
 1               5                  10

<210> SEQ ID NO 58
<211> LENGTH: 10
<212> TYPE: PRT
<213> ORGANISM: Homo sapiens

<400> SEQUENCE: 58

Tyr Val Asp Leu Asp Leu His His Gly Asp
 1               5                  10
```

<210> SEQ ID NO 59
<211> LENGTH: 10
<212> TYPE: PRT
<213> ORGANISM: Homo sapiens

<400> SEQUENCE: 59

Ile Val Asp Trp Asp Val His His Gly Asn
 1               5                  10

<210> SEQ ID NO 60
<211> LENGTH: 10
<212> TYPE: PRT
<213> ORGANISM: Homo sapiens

<400> SEQUENCE: 60

Ile Val Asp Trp Asp Ile His His Gly Asn
 1               5                  10

<210> SEQ ID NO 61
<211> LENGTH: 10
<212> TYPE: PRT
<213> ORGANISM: Homo sapiens

<400> SEQUENCE: 61

Ile Val Asp Trp Asp Val His His Gly Gln
 1               5                  10

<210> SEQ ID NO 62
<211> LENGTH: 10
<212> TYPE: PRT
<213> ORGANISM: Homo sapiens

<400> SEQUENCE: 62

Ile Val Asp Trp Asp Val His His Gly Asn
 1               5                  10

<210> SEQ ID NO 63
<211> LENGTH: 10
<212> TYPE: PRT
<213> ORGANISM: Homo sapiens

<400> SEQUENCE: 63

Ile Val Asp Trp Asp Val His His Gly Asn
 1               5                  10

<210> SEQ ID NO 64
<211> LENGTH: 4
<212> TYPE: PRT
<213> ORGANISM: Homo sapiens

<400> SEQUENCE: 64

Gly Gly Gly Tyr
 1

<210> SEQ ID NO 65
<211> LENGTH: 4
<212> TYPE: PRT
<213> ORGANISM: Homo sapiens

<400> SEQUENCE: 65

Gly Gly Gly Tyr
 1

<210> SEQ ID NO 66
<211> LENGTH: 4

```
<212> TYPE: PRT
<213> ORGANISM: Homo sapiens

<400> SEQUENCE: 66

Gly Gly Gly Tyr
1

<210> SEQ ID NO 67
<211> LENGTH: 4
<212> TYPE: PRT
<213> ORGANISM: Homo sapiens

<400> SEQUENCE: 67

Gly Gly Gly Tyr
1

<210> SEQ ID NO 68
<211> LENGTH: 4
<212> TYPE: PRT
<213> ORGANISM: Homo sapiens

<400> SEQUENCE: 68

Gly Gly Gly Tyr
1

<210> SEQ ID NO 69
<211> LENGTH: 4
<212> TYPE: PRT
<213> ORGANISM: Homo sapiens

<400> SEQUENCE: 69

Glu Gly Gly His
1

<210> SEQ ID NO 70
<211> LENGTH: 4
<212> TYPE: PRT
<213> ORGANISM: Homo sapiens

<400> SEQUENCE: 70

Glu Gly Gly His
1

<210> SEQ ID NO 71
<211> LENGTH: 4
<212> TYPE: PRT
<213> ORGANISM: Homo sapiens

<400> SEQUENCE: 71

Glu Gly Gly Tyr
1

<210> SEQ ID NO 72
<211> LENGTH: 4
<212> TYPE: PRT
<213> ORGANISM: Homo sapiens

<400> SEQUENCE: 72

Glu Gly Gly Tyr
1

<210> SEQ ID NO 73
<211> LENGTH: 4
<212> TYPE: PRT
<213> ORGANISM: Homo sapiens
```

<400> SEQUENCE: 73

Glu Gly Gly His
1